United States Patent
Angell et al.

(10) Patent No.: US 7,642,276 B2
(45) Date of Patent: Jan. 5, 2010

(54) FUSED HETEROARYL DERIVATIVES FOR USE AS P38 KINASE INHIBITORS

(75) Inventors: Richard Martyn Angell, London (GB); Ian Robert Baldwin, Stevenage (GB); Paul Bamborough, Stevenage (GB); Nigel Marc Deboeck, Stevenage (GB); Timothy Longstaff, Stevenage (GB); Stephen Swanson, Stevenage (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 289 days.

(21) Appl. No.: 10/522,955

(22) PCT Filed: Jul. 30, 2003

(86) PCT No.: PCT/GB03/03316

§ 371 (c)(1), (2), (4) Date: Nov. 14, 2005

(87) PCT Pub. No.: WO2004/010995

PCT Pub. Date: Feb. 5, 2004

(65) Prior Publication Data

US 2006/0122221 A1 Jun. 8, 2006

(30) Foreign Application Priority Data

Jul. 31, 2002 (GB) ................ 0217757.4

(51) Int. Cl.
*A61K 31/423* (2006.01)
*A61K 31/404* (2006.01)
*A61K 31/428* (2006.01)
*A61K 31/496* (2006.01)
*A61K 31/5377* (2006.01)
*A61K 31/4025* (2006.01)
*A61K 31/341* (2006.01)
*A61K 31/381* (2006.01)
*C07D 403/04* (2006.01)
*C07D 261/20* (2006.01)
*C07D 277/62* (2006.01)
*C07D 413/04* (2006.01)

(52) U.S. Cl. ............... 514/379; 514/415; 514/367; 514/252.13; 514/231.5; 514/422; 514/444; 514/461; 544/111; 544/359; 548/241; 548/518; 549/59; 549/472

(58) Field of Classification Search ............ 514/379, 514/415, 367, 231.5, 252.13, 422, 444, 461; 544/111, 359; 548/241, 469, 152, 518; 549/59, 549/472

See application file for complete search history.

(56) References Cited

U.S. PATENT DOCUMENTS

| | | | |
|---|---|---|---|
| 4,200,750 A | 4/1980 | Warner et al. | |
| 4,968,804 A | 11/1990 | Stanek et al. | |
| 5,064,832 A | 11/1991 | Stanek et al. | |
| 5,236,934 A | 8/1993 | VanAtten | |
| 5,246,943 A | 9/1993 | Blankley et al. | |
| 5,521,213 A | 5/1996 | Prasit et al. | |
| 5,534,518 A | 7/1996 | Henrie et al. | |
| 5,658,903 A | 8/1997 | Adams et al. | |
| 5,858,995 A | 1/1999 | Kawai et al. | |
| 5,877,190 A | 3/1999 | Dhainaut et al. | |
| 5,932,576 A | 8/1999 | Anantanarayan et al. | |

(Continued)

FOREIGN PATENT DOCUMENTS

EP 0 533 268 9/1992

(Continued)

OTHER PUBLICATIONS

Hijikata, et al. "Inhibition of Protein Tyrosine Kinase by 5-S-GAD, a Novel Antibacterial Substance from an Insect", Biochemical and Biophysical Research Communications, vol. 237, Issue 2, pp. 423-426 (1997).*
Schindler, et al., "p38 Pathway Kinases as Anti-inflammatory Drug Targets", Journal of Dental Research, vol. 86(9), pp. 800-811 (2007).*
U.S. Appl. No. 10/492,714, filed Apr. 15, 2004, Angell et al.
U.S. Appl. No. 10/587,790, filed Jan. 27, 2005, Bamborough, et al.
U.S. Appl. No. 11/917,534, filed Jun. 16, 2006, Chandi, et al.
Boehm et al., *Expert Opinion of Therapeutic Patents*, vol. 10 (1) pp. 25-37 (2000).
Boehm, et al, *Journal of Medicinal Chemistry*, vol. 39(20) pp. 3929-3937 (1996).

(Continued)

*Primary Examiner*—Yong Chu
(74) *Attorney, Agent, or Firm*—Dara L. Dinner; Charles M. Kinzig

(57) ABSTRACT

Compounds of formula (I): wherein A is a 5-membered heteroaryl ring are inhibitors of p38 kinase and are useful in the treatment of conditions or disease states mediated by p38 kinase activity or mediated by cytokines produced by the activity of p38, such as rheumatoid arthritis.

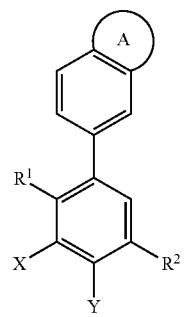

(I)

16 Claims, No Drawings

U.S. PATENT DOCUMENTS

| | | | |
|---|---|---|---|
| 5,945,418 | A | 8/1999 | Bemis et al. |
| 5,977,103 | A | 11/1999 | Adams et al. |
| 6,060,491 | A | 5/2000 | Pruitt et al. |
| 6,080,767 | A | 6/2000 | Klein et al. |
| 6,087,496 | A | 7/2000 | Anantanarayan et al. |
| 6,130,235 | A | 10/2000 | Mavunkel et al. |
| 6,147,080 | A | 11/2000 | Bemis et al. |
| 6,174,887 | B1 | 1/2001 | Haruta et al. |
| 6,251,914 | B1 | 6/2001 | Adams et al. |
| 6,277,989 | B1 | 8/2001 | Chakravarty et al. |
| 6,323,227 | B1 | 11/2001 | Klein et al. |
| 6,376,546 | B1 | 4/2002 | Shoda et al. |
| 6,392,047 | B1 | 5/2002 | Geissler et al. |
| 6,399,627 | B1 | 6/2002 | Song et al. |
| 6,420,561 | B1 | 7/2002 | Haruta et al. |
| 6,436,925 | B1 | 8/2002 | Lubisch et al. |
| 6,448,257 | B1 | 9/2002 | Mavunkel et al. |
| 6,451,794 | B1 | 9/2002 | Beswick et al. |
| 6,498,166 | B1 | 12/2002 | Campbell et al. |
| 6,509,361 | B1 | 1/2003 | Weier et al. |
| 6,509,363 | B2 | 1/2003 | Salituro et al. |
| 6,545,054 | B1 | 4/2003 | Song et al. |
| 6,576,632 | B1 | 6/2003 | Goldstein et al. |
| 6,579,872 | B1 | 6/2003 | Brown et al. |
| 6,605,625 | B2 | 8/2003 | Peukert et al. |
| 6,638,980 | B1 | 10/2003 | Su et al. |
| 6,696,464 | B2 | 2/2004 | McClure et al. |
| 6,699,994 | B1 | 3/2004 | Babu et al. |
| 6,774,127 | B2 | 8/2004 | Adams et al. |
| 6,794,377 | B2 | 9/2004 | Peukert et al. |
| 6,821,965 | B1 | 11/2004 | Brown et al. |
| 6,855,719 | B1 | 2/2005 | Thomas et al. |
| 6,867,209 | B1 | 3/2005 | Mavunkel et al. |
| 6,924,392 | B2 | 8/2005 | Peukert et al. |
| 6,936,719 | B2 | 8/2005 | Babu et al. |
| 6,956,037 | B2 | 10/2005 | Brown et al. |
| 7,125,898 | B2 | 10/2006 | Aston et al. ............... 546/268.1 |
| 7,151,118 | B2 | 12/2006 | Angell et al. .................. 514/63 |
| 7,166,623 | B2 | 1/2007 | Angell et al. ............ 514/227.8 |
| 7,183,297 | B2 | 2/2007 | Angell et al. .......... 514/217.12 |
| 7,208,629 | B2 | 4/2007 | Angell et al. ................. 544/60 |
| 7,271,289 | B2 | 9/2007 | Aston |
| 7,309,800 | B2 | 12/2007 | Angell et al. |
| 7,384,963 | B2 | 6/2008 | Angell et al. ................ 546/228 |
| 7,396,943 | B2 | 7/2008 | Benesh et al. .......... 514/217.12 |
| 2001/0011135 | A1 | 8/2001 | Riedl et al. |
| 2003/0055088 | A1 | 3/2003 | Shao et al. |
| 2003/0139605 | A1 | 7/2003 | Riedl et al. |
| 2003/0225089 | A1 | 12/2003 | Jung et al. |
| 2004/0013287 | A1 | 1/2004 | Takeuchi et al. |
| 2004/0038858 | A1 | 2/2004 | Dorsch et al. |
| 2004/0053942 | A1 | 3/2004 | Alberti et al. |
| 2004/0110802 | A1* | 6/2004 | Thorarensen et al. ....... 514/355 |
| 2004/0116479 | A1 | 6/2004 | Haviv et al. |
| 2004/0138287 | A1 | 7/2004 | Barth et al. |
| 2004/0162281 | A1 | 8/2004 | Babu et al. |
| 2004/0176446 | A1 | 9/2004 | Alonso-Alija et al. |
| 2004/0242868 | A1 | 12/2004 | Angell et al. .................. 514/63 |
| 2004/0254200 | A1 | 12/2004 | Davis et al. |
| 2005/0020590 | A1 | 1/2005 | Lang et al. |
| 2005/0065195 | A1 | 3/2005 | Angell et al. ................ 514/364 |
| 2006/0089393 | A1 | 4/2006 | Angell et al. |
| 2006/0264479 | A1 | 11/2006 | Aston et al. ............... 546/268.1 |
| 2006/0276516 | A1 | 12/2006 | Aston et al. ............... 546/268.1 |
| 2007/0054942 | A1 | 3/2007 | Patel et al. |
| 2007/0105850 | A1 | 5/2007 | Aston |
| 2007/0112046 | A1 | 5/2007 | Angell et al. |
| 2007/0129354 | A1 | 6/2007 | Aston et al. |
| 2007/0142372 | A1 | 6/2007 | Campos et al. |
| 2007/0142476 | A1 | 6/2007 | Angell et al. |
| 2007/0161673 | A1 | 7/2007 | Barker et al. |
| 2007/0161684 | A1 | 7/2007 | Walker |
| 2008/0051416 | A1 | 2/2008 | Boehm et al. |

FOREIGN PATENT DOCUMENTS

| | | |
|---|---|---|
| EP | 0 346 841 | 6/2003 |
| EP | 0 430 033 | 4/2004 |
| GB | 2 276 161 | 3/1993 |
| GB | 2 273 930 | 12/1993 |
| GB | 2 295 387 | 5/1996 |
| JP | 11218884 | 8/1999 |
| WO | WO 94/15920 | 7/1994 |
| WO | WO 95/06644 | 3/1995 |
| WO | WO 95/11243 | 4/1995 |
| WO | WO 95/15954 | 6/1995 |
| WO | WO 95/17401 | 6/1995 |
| WO | WO 95/29907 | 11/1995 |
| WO | WO 95/30675 | 11/1995 |
| WO | WO 96/31508 | 10/1996 |
| WO | WO 96/31509 | 10/1996 |
| WO | WO 97/03034 | 1/1997 |
| WO | WO 98/57934 | 12/1998 |
| WO | WO 99/32463 | 7/1999 |
| WO | WO 00/12074 | 3/2000 |
| WO | WO 00/12497 | 3/2000 |
| WO | WO 00/56738 | 9/2000 |
| WO | WO 00/71493 | 11/2000 |
| WO | WO 00/71509 | 11/2000 |
| WO | WO 00/71510 | 11/2000 |
| WO | WO 00/71511 | 11/2000 |
| WO | WO 01/27089 | 4/2001 |
| WO | WO 01/70695 | 9/2001 |
| WO | WO 02/40486 | 5/2002 |
| WO | WO-03/097610 | * 11/2003 |

OTHER PUBLICATIONS

Ceccarelli et al., *European Journal of Medicinal Chemistry*, vol. 33 (12) pp. 943-955 (1998).
Courtney, S. et al., *Bioorganic & Medicinal Chemistry Letters*, vol. 14 pp. 3269-3273 (2004).
Foster, et al., *Drug News Perspect.*, vol. 13(8) pp. 488-497 (2000).
Gabriele et al., *European Journal of Organic Chemistry*, vol. 2001 (24) pp. 4607-4613 (2001).
Han et al., *Biohemica et Biophysica Acta—Molecular Cell Research*, vol. 1265 (2-3) pp. 224-227 (1995.
Hanson, *Expert Opinion on Therapeutic Patents*, vol. 7(7) pp. 729-733 (1997).
Henry et al., *Drugs of the Future*, vol. 24 (12) pp. 1345-1354 (1999).
Henry, et al., *Bioorganic & Medicinal Chemistry Letters*, vol. 8 pp. 3335-3340 (1998).
Herlaar, et al., Molecular Medicine Today, vol. 5 pp. 439-447 (1999).
Jiang et al, *Journal of Biological Chemistry*, vol. 271 (30) pp. 17920-17926 (1996).
Li et al., *Biochemical and Biophysical Research Communications*, vol. 228 (2) pp. 334-340 (1996).
Liebeskind et al., *Organic Letters*, vol. 4 (6) pp. 979-981 (2002).
Marin, et al., *Blood*, vol. 98(3) pp. 667-673 (2001).
Moreland et al., *Annals of Internal Medicine*, vol. 130 (6) pp. 478-486 (1999).
Murali Dhar et al., *Bioorganic and Medicinal Chemistry Letters*, vol. 12 (21) pp. 3125-3128 (2002).
Rankin et al., *British Journal of Rheumatology*, vol. 34 pp. 334-342 (1995).
Salituro et al., *Current Medicinal Chemistry*, vol. 6 pp. 807-823 (1999).
Underwood, et al., *Journal of Pharmacology and Experimental Therapeutics*, vol. 293 (1) pp. 281-288 (2000).
Wadsworth, et al., Journal of Pharmacology and Experimental Therapeutics, vol. 291(2) pp. 680-687 (1999).
Wang et al., *Journal of Biological Chemistry*, vol. 272 (38) pp. 23668-23674 (1997).

* cited by examiner

FUSED HETEROARYL DERIVATIVES FOR USE AS P38 KINASE INHIBITORS

This application is the §371 national stage entry of PCT/GB2003/003316 application, filed 30 Jul. 2003.

This invention relates to novel compounds and their use as pharmaceuticals, particularly as p38 kinase inhibitors, for the treatment of conditions or disease states mediated by p38 kinase activity or mediated by cytokines produced by the activity of p38 kinase.

We have now found a group of novel compounds that are inhibitors of p38 kinase.

According to the invention there is provided a compound of formula (I):

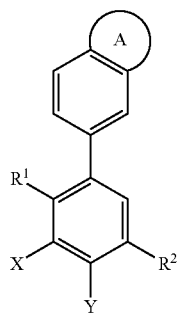

(I)

wherein

A is a fused 5-membered heteroaryl ring optionally substituted by up to two substituents independently selected from $C_{1-6}$alkyl, —$(CH_2)_m$—$C_{3-7}$cycloalkyl, halogen, cyano, trifluoromethyl, —$(CH_2)_m OR^3$, —$(CH_2)_m CO_2 R^3$, —$(CH_2)_m NR^3 R^4$, —$(CH_2)_m CONR^3 R^4$, —$(CH_2)_m NHCOR^3$, —$(CH_2)_m SO_2 NR^3 R^4$, —$(CH_2)_m NHSO_2 R^3$, —$(CH_2)_m SO_2 (CH_2)_n R^5$, a 5- or 6-membered heterocyclyl ring containing nitrogen optionally substituted by $C_{1-2}$alkyl or —$(CH_2)_m CO_2 R^3$, and a 5-membered heteroaryl ring optionally substituted by $C_{1-2}$alkyl;

$R^1$ is selected from methyl and chloro;

$R^2$ is selected from —NH—CO—$R^6$ and —CO—NH—$(CH_2)_q$—$R^7$;

$R^3$ is selected from hydrogen, $C_{1-6}$alkyl optionally substituted by up to two OH groups, —$(CH_2)_m$—$C_{3-7}$cycloalkyl, —$(CH_2)_m$phenyl optionally substituted by $R^8$ and/or $R^9$ and —$(CH_2)_m$heteroaryl optionally substituted by $R^8$ and/or $R^9$, $R^4$ is selected from hydrogen and $C_{1-6}$alkyl, or $R^3$ and $R^4$, together with the nitrogen atom to which they are bound, form a 5- or 6-membered heterocyclic ring optionally containing one additional heteroatom selected from oxygen, sulfur and N—$R^{10}$;

$R^5$ is selected from $C_{1-6}$alkyl optionally substituted by up to three halogen atoms, $C_{2-6}$alkenyl optionally substituted by phenyl, $C_{3-7}$cycloalkyl, heteroaryl optionally substituted by up to three $R^8$ and/or $R^9$ groups, and phenyl optionally substituted by $R^8$ and/or $R^9$;

$R^6$ is selected from hydrogen, $C_{1-6}$alkyl, —$(CH_2)_q$—$C_{3-7}$cycloalkyl, trifluoromethyl, —$(CH_2)_r$heteroaryl optionally substituted by $R^{11}$ and/or $R^{12}$, and —$(CH_2)_r$phenyl optionally substituted by $R^{11}$ and/or $R^{12}$;

$R^7$ is selected from hydrogen, $C_{1-6}$alkyl, $C_{3-7}$cycloalkyl, —$CONHR^{13}$, phenyl optionally substituted by $R^{11}$ and/or $R^{12}$, and heteroaryl optionally substituted by $R^{11}$ and/or $R^{12}$;

$R^8$ and $R^9$ are each independently selected from halogen, cyano, trifluoromethyl, nitro, $C_{1-6}$alkyl, $C_{1-6}$alkoxy, —$CONR^{13}R^{14}$, —$COR^{15}$, —$CO_2R^{15}$, and heteroaryl, or $R^8$ and $R^9$ are linked to form a fused 5-membered heterocyclyl ring containing one heteroatom selected from oxygen, sulphur and N—$R^{10}$, or a fused heteroaryl ring;

$R^{10}$ is selected from hydrogen and methyl;

$R^{11}$ is selected from $C_{1-6}$alkyl, $C_{1-6}$alkoxy, —$(CH_2)_q$—$C_{3-7}$cycloalkyl, —$CONR^{13}R^{14}$, —$NHCOR^{14}$, halogen, CN, —$(CH_2)_s NR^{16}R^{17}$, trifluoromethyl, phenyl optionally substituted by one or more $R^{12}$ groups, and heteroaryl optionally substituted by one or more $R^{12}$ groups;

$R^{12}$ is selected from $C_{1-6}$alkyl, $C_{1-6}$alkoxy, halogen, trifluoromethyl, and —$(CH_2)_s NR^{16}R^{17}$;

$R^{13}$ and $R^{14}$ are each independently selected from hydrogen and $C_{1-6}$alkyl, or $R^{13}$ and $R^{14}$, together with the nitrogen atom to which they are bound, form a 5- or 6-membered heterocyclic ring optionally containing one additional heteroatom selected from oxygen, sulfur and N—$R^{10}$, wherein the ring may be substituted by up to two $C_{1-6}$alkyl groups;

$R^{15}$ is $C_{1-6}$alkyl;

$R^{16}$ is selected from hydrogen, $C_{1-6}$alkyl and —$(CH_2)_q$—$C_{3-7}$cycloalkyl optionally substituted by $C_{1-6}$alkyl, $R^{17}$ is selected from hydrogen and $C_{1-6}$alkyl, or $R^{16}$ and $R^{17}$, together with the nitrogen atom to which they are bound, form a 5- or 6-membered heterocyclic ring optionally containing one additional heteroatom selected from oxygen, sulfur and N—$R^{10}$;

X and Y are each independently selected from hydrogen, methyl and halogen;

m is selected from 0, 1, 2 and 3;

n is selected from 0, 1, 2 and 3;

q is selected from 0, 1 and 2;

r is selected from 0 and 1; and s is selected from 0, 1, 2 and 3.

According to a further embodiment of the invention there is provided a compound of formula (IA):

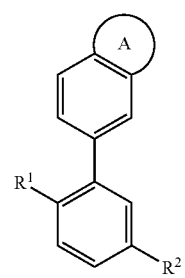

(IA)

wherein

A is a fused 5-membered heteroaryl ring optionally substituted by up to two substituents independently selected from $C_{1-6}$alkyl, —$(CH_2)_m$—$C_{3-7}$cycloalkyl, halogen, cyano, trifluoromethyl, —$(CH_2)_m OR^3$, —$(CH_2)_m NR^3 R^4$, —$(CH_2)_m CONR^3 R^4$, —$(CH_2)_m NHCOR^3$, $X(CH_2)_m So2NR^3R^4$, —$(CH_2)_m NHSO_2 R^3$, —$(CH_2)_m SO_2 (CH_2)_n R^5$, a 5- or 6-membered heterocyclyl ring containing nitrogen optionally substituted by $C_{1-2}$alkyl and a 5-membered heteroaryl ring optionally substituted by $C_{1-2}$alkyl;

$R^1$ is selected from methyl and chloro;

$R^2$ is selected from —NH—CO—$R^6$ and —CO—NH—$(CH_2)_q$—$R^7$;

$R^3$ is selected from hydrogen, $C_{1-6}$alkyl optionally substituted by up to two OH groups, —$(CH_2)_m$—$C_{3-7}$cycloalkyl, —(CH$_2$)$_m$phenyl optionally substituted by R$^8$ and/or R$^9$ and —(CH$_2$)$_m$heteroaryl optionally substituted by R$^8$ and/or R$^9$ R$^4$ is selected from hydrogen and C$_{1-6}$alkyl, or R$^3$ and R$^4$, together with the nitrogen atom to which they are bound, form a 5-or 6-membered heterocyclic ring optionally containing one additional heteroatom selected from oxygen, sulfur and N—R$^{10}$;

R$^5$ is selected from C$_{1-6}$alkyl, C$_{3-7}$cycloalkyl, heteroaryl optionally substituted by R$^8$ and/or R$^9$, and phenyl optionally substituted by R$^8$ and/or R$^9$;

R$^6$ is selected from hydrogen, C$_{1-6}$alkyl, —(CH$_2$)$_q$—C$_{3-7}$cycloalkyl, trifluoromethyl, —(CH$_2$)$_r$heteroaryl optionally substituted by R$^{11}$ and/or R$^{12}$, and —(CH$_2$)$_r$phenyl optionally substituted by R$^{11}$ and/or R$^{12}$;

R$^7$ is selected from hydrogen, C$_{1-6}$alkyl, C$_{3-7}$cycloalkyl, CONHR$^{13}$, phenyl optionally substituted by R$^{11}$ and/or R$^{12}$, and heteroaryl optionally substituted by R$^{11}$ and/or R$^{12}$;

R$^8$ and R$^9$ are each independently selected from halogen, cyano, trifluoromethyl, C$_{1-6}$alkyl, C$_{1-6}$alkoxy, COR$^{15}$, CO$_2$R$^{15}$, and heteroaryl, or R$^8$ and R$^9$ are linked to form a fused 5-membered heterocyclyl ring containing one heteroatom selected from oxygen, sulphur and N—R$^{10}$;

R$^{10}$ is selected from hydrogen and methyl;

R$^{11}$ is selected from C$_{1-6}$alkyl, C$_{1-6}$alkoxy, —(CH$_2$)$_q$—C$_{3-7}$cycloalkyl, —CONR$^{13}$R$^{14}$, —NHCOR$^{14}$, halogen, CN, —(CH$_s$NR$^{16}$R$^{17}$$_3$, trifluoromethyl, phenyl optionally substituted by one or more R$^{12}$ groups, and heteroaryl optionally substituted by one or more R$^{12}$ groups;

R$^{12}$ is selected from C$_{1-6}$alkyl, C$_{1-6}$alkoxy, halogen, trifluoromethyl, and —(CH$_2$)$_s$NR$^{16}$R$^{17}$;

R$^{13}$ and R$^{14}$ are each independently selected from hydrogen and C$_{1-6}$alkyl, or R$^{13}$ and R$^{14}$, together with the nitrogen atom to which they are bound, form a 5- or 6-membered heterocyclic ring optionally containing one additional heteroatom selected from oxygen, sulfur and N—R$^{10}$, wherein the ring may be substituted by up to two C$_{1-6}$alkyl groups;

R$^{15}$ is C$_{1-6}$alkyl;

R$^{16}$ is selected from hydrogen, C$_{1-6}$alkyl and —(CH$_2$)$_q$—C$_{3-7}$cycloalkyl optionally substituted by C$_{1-6}$alkyl, R$^{17}$ is selected from hydrogen and C$_{1-6}$alkyl, or R$^{16}$ and R$^{17}$, together with the nitrogen atom to which they are bound, form a 5- or 6-membered heterocyclic ring optionally containing one additional heteroatom selected from oxygen, sulfur and N—R$^{10}$;

m is selected from 0, 1, 2 and 3;

n is selected from 0, 1, 2 and 3;

q is selected from 0, 1 and 2;

r is selected from 0 and 1; and s is selected from 0, 1, 2 and 3.

Representative examples of A include fused 5-membered heteroaryl rings containing up to two heteroatoms independently selected from oxygen, nitrogen and sulfur. Preferred fused 5-membered heteroaryl rings include rings containing up to two heteroatoms independently selected from oxygen and nitrogen, in particular rings containing two heteroatoms selected from oxygen and nitrogen such as rings containing a nitrogen atom and one additional heteroatom selected from oxygen and nitrogen. In one embodiment, A is selected from fused pyrazolyl and isoxazolyl rings such as those shown below:

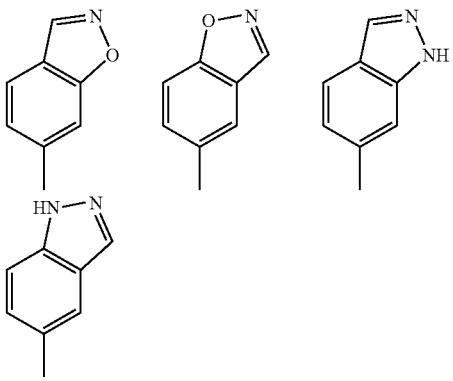

In a further embodiment, A is selected from fused pyrrolyl and thiazolyl rings such as those shown below:

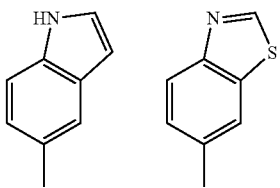

Ring A may be optionally substituted by up to two substituents, located on any position on the ring. Preferably ring A is substituted by one substituent.

In one embodiment, A is optionally substituted by up to two substituents independently selected from C$_{1-6}$alkyl, —(CH$_2$)$_m$—C$_{3-7}$cycloalkyl, halogen, cyano, trifluoromethyl, —(CH$_2$)$_m$OR$^3$, —(CH$_2$)$_m$NR$^3$R$^4$, —(CH$_2$)$_m$CONR$^3$R$^4$, —(CH$_2$)$_m$NHCOR$^3$, —(CH$_2$)$_m$SO$_2$NR$^3$R$^4$, —(CH$_2$)$_m$NHSO$_2$R$^3$, —(CH$_2$)$_m$SO$_2$(CH$_2$)$_n$R$^5$, a 5- or 6-membered heterocyclyl ring containing nitrogen optionally substituted by C$_{1-2}$alkyl, and a 5-membered heteroaryl ring optionally substituted by C$_{1-2}$alkyl.

Representative examples of substituents for A include C$_{1-4}$alkyl, in particular methyl; —(CH$_2$)$_m$—C$_{3-7}$cycloalkyl, in particular —(CH$_2$)$_m$-cyclopropyl; —(CH$_2$)$_m$CO$_2$R$^3$; —(CH$_2$)$_m$NR$^3$R$^4$; —(CH$_2$)$_m$CONR$^3$R$^4$; —(CH$_2$)$_m$NHCOR$^3$; —(CH$_2$)$_m$SO$_2$(CH$_2$)$_n$R$^5$; and a 5- or 6-membered heterocyclyl ring containing nitrogen, in particular 4-piperidinyl, optionally substituted by C$_{1-2}$alkyl or —(CH$_2$)$_m$CO$_2$R$^3$.

Typical substituents for A include C$_{1-4}$alkyl, in particular methyl, —(CH$_2$)$_m$OR$^3$, —(CH$_2$)$_m$NR$^3$R$^4$, —(CH$_2$)$_m$SO$_2$(CH$_2$)$_n$R$^5$, and a 5- or 6-membered heterocyclyl ring containing nitrogen, in particular piperazinyl and piperidinyl such as 4-piperidinyl.

A representative example of R$^1$ is methyl.

In one embodiment, R$^2$ is —CO—NH—(CH$_2$)$_q$—R$^7$.

Representative examples of R$^3$ include hydrogen; C$_{1-6}$alkyl optionally substituted by up to two OH groups, in particular methyl, ethyl, n-propyl, isopropyl, t-butyl or 2,2-dimethylpropyl optionally subsituted by up to two OH groups; —(CH$_2$)$_m$—C$_{3-7}$cycloalkyl, in particular —(CH$_2$)$_m$-cyclopropyl; —(CH$_2$)$_m$phenyl optionally substituted by R$^8$ and/or R$^9$; and —(CH$_2$)$_m$heteroaryl, in particular thiazolyl, optionally substituted by R$^8$ and/or R$^9$.

Further representative examples of R$^3$ include hydrogen and C$_{1-4}$alkyl substituted by up to two OH groups, in particular 1,3-dihydroxyprop-2-yl.

Respresentative examples of $R^4$ include hydrogen and $C_{1-4}$alkyl such as methyl. In particular, a representative example of $R^4$ is hydrogen.

In one embodiment, $R^3$ and $R^4$, together with the nitrogen atom to which they are bound, form a 5- or 6-membered heterocyclic ring optionally containing one additional heteroatom selected from oxygen, sulfur and N—$R^{10}$, in particular a pyrrolidinyl, piperidinyl, piperazinyl or 4-methylpiperazinyl, or morpholinyl ring.

In one embodiment, $R^5$ is selected from $C_{1-6}$alkyl, $C_{3-7}$cycloalkyl, heteroaryl optionally substituted by $R^8$ and/or $R^9$, and phenyl optionally substituted by $R^8$ and/or $R^9$.

Representative examples of $R^5$ include $C_{1-6}$alkyl optionally substituted by up to three halogen atoms, in particular methyl, ethyl, n-propyl, isopropyl, n-butyl and n-hexyl optionally substituted by up to three halogen atoms; $C_{2-6}$alkenyl optionally substituted by phenyl, in particular ethenyl optionally substituted by phenyl; $C_{3-7}$cycloalkyl, in particular cyclopropyl; heteroaryl optionally substituted by $R^8$ and/or $R^9$, in particular a 5-membered heteroaryl ring containing at least one heteroatom selected from oxyen, nitrogen and sulphur such as furyl, thienyl, isoxazolyl, imidazolyl or pyrazolyl optionally substituted by up to three $R^8$ and/or $R^9$ groups; and phenyl optionally substituted by $R^8$ and/or $R^9$.

Further representative examples of $R^5$ include $C_{1-4}$alkyl, in particular methyl, phenyl optionally substituted by $R^8$ and/or $R^9$, and a 5-membered heteroaryl ring containing at least one heteroatom selected from oxygen, nitrogen and sulphur optionally substituted by $R^8$ and/or $R^9$, in particular thienyl optionally substituted by $R^8$ and/or $R^9$.

Representative examples of $R^6$ include —$(CH_2)_r$heteroaryl optionally substituted by $R^{11}$ and/or $R^{12}$, in particular in a 5- or 6-membered heteroaryl containing at least one heteroatom selected from oxygen, nitrogen and sulfur, for example, pyridinyl optionally substituted by —$(CH_2)_s$NR$^{16}$R$^{17}$, furyl or thienyl.

Representative examples of $R^7$ include $C_{3-7}$cycloalkyl, phenyl optionally substituted by $R^{11}$ and/or $R^{12}$, and heteroaryl optionally substituted by $R^{11}$ and/or $R^{12}$. In one embodiment, $R^7$ is selected from $C_{3-6}$cycloalkyl such as cyclopropyl, cyclobutyl, cyclopentyl or cyclohexyl, in particular cyclopropyl; phenyl optionally substituted by $C_{1-4}$alkoxy, in particular methoxy, or —$(CH_2)_s$NR$^{16}$R$^{17}$; and heteroaryl optionally substituted by $R^{11}$ and/or $R^{12}$, in particular a 5- or 6-membered heteroaryl containing at least one heteroatom selected from oxygen, nitrogen and sulfur, for example, pyridinyl, thiazolyl or thiadiazolyl. In a further embodiment, $R^7$ is $C_{3-6}$cycloalkyl, in particular cyclopropyl.

In one embodiment, $R^8$ and $R^9$ are each independently selected from halogen, cyano, trifluoromethyl, $C_{1-6}$alkyl, $C_{1-6}$alkoxy, —COR$^{15}$, —CO$_2$R$^{15}$, and heteroaryl.

Representative examples of $R^8$ and $R^9$ include halogen, in particular chlorine or fluorine; cyano; trifluoromethyl; nitro; $C_{1-4}$alkyl, in particular methyl, ethyl, n-propyl, isopropyl or n-butyl; $C_{1-4}$alkoxy, in particular methoxy; —CONR$^{13}$R$^{14}$; —COR$^{15}$; —CO$_2$R$^{15}$; and heteroaryl, in particular a 5-membered heteroaryl ring containing up to two heteroatoms independently selected from nitrogen and oxygen, for example isoxazolyl.

Further representative examples of $R^8$ and $R^9$ include halogen, in particular fluorine, cyano, trifluoromethyl, $C_{1-4}$alkoxy, in particular methoxy, COR$^{15}$, CO$_2$R$^{15}$, and heteroaryl, in particular a 5-membered heteroaryl ring containing up to two heteroatoms independently selected from nitrogen and oxygen, for example isoxazolyl.

In another embodiment, $R^8$ and $R^9$ are linked to form a fused 5-membered heterocyclyl ring containing one heteroatom selected from oxygen, sulphur and N—$R^{10}$.

Representative examples include $R^8$ and $R^9$ being linked to form a fused 5-membered heterocyclyl ring containing oxygen or a fused 5-membered heteroaryl ring containing up to three heteroatoms selected from oxygen and nitrogen.

A further representative example is $R^8$ and $R^9$ being linked to form a fused 5-membered heterocyclyl ring containing oxygen.

Representative examples of $R^{11}$ and $R^{12}$ include $C_{1-4}$alkoxy, in particular methoxy, and —$(CH_2)_s$NR$^{16}$R$^{17}$.

Representative examples of $R^{13}$ and $R^{14}$ include hydrogen and $C_{1-4}$alkyl, in particular hydrogen and methyl.

Representative examples of $R^{15}$ include $C_{1-4}$alkyl, in particular methyl.

In one embodiment $R^{16}$ and $R^{17}$, together with the nitrogen atom to which they are bound, form a 5- or 6-membered heterocyclic ring optionally further containing one additional oxygen atom, in particular pyrrolidinyl or morpholino.

In one embodiment, X and Y are each independently selected from hydrogen, chlorine and fluorine. Representative examples of X include hydrogen and fluorine. A representative example of Y is hydrogen. In a further embodiment, X and Y are each hydrogen.

In one embodiment, m is selected from 0, 1 and 2, in particular 0 and 1.

Representative examples of n include 0, 1 and 2. Further representative examples of n include 0 and 1.

Representative examples of q include 0 and 1, in particular 0.

A representative example of r is 0.

A representative example of s is 0.

It is to be understood that the present invention covers all combinations of particular and preferred groups described hereinabove. It is also to be understood that the present invention encompasses compounds of formula (I) in which a particular group or parameter, for example $R^{10}$, $R^{12}$, $R^{13}$, $R^{14}$, $R^{16}$, $R^{17}$, m, q or s, may occur more than once. In such compounds it will be appreciated that each group or parameter is independently selected from the values listed.

Particular compounds according to the invention include those mentioned in the Examples. Specific examples which may be mentioned include:

N-[4-methyl-3-(3-piperidin-4-yl-1,2-benzisoxazol-6-yl) phenyl]-2-pyrrolidin-1-ylisonicotinamide;

N-cyclopropyl-4methyl-3-[1-(phenylsulfonyl)-1H-indazol-5-yl]benzamide;

N-cyclopropyl-3-{1-[(3-fluorophenyl)sulfonyl]-1H-indazol-5-yl}-4-methylbenzamide;

N-cyclopropyl-4-methyl-3-[1-(methylsulfonyl)-1H-indazol-5-yl]benzamide;

N-cyclopropyl-3-{1-[(4-fluorophenyl)sulfonyl]-1H-indazol-5-yl)}-4-methyl benzamide;

N-cyclopropyl-4-methyl-3-[3-(4-morpholinyl)-1,2-benzisoxazol-6-yl]benzamide;

N-cyclopropyl-4-methyl-3-{3-[2-oxo-2-(1,3-thiazol-2-ylamino)ethyl]-1,2-benzisoxazol-6-yl}benzamide;

N-cyclopropylmethyl-3-[3-(4-morpholinylmethyl)-1,2-benzisoxazol-6-yl]benzamide;

N-cyclopropylmethyl-3-[3-(1-pyrrolidinylmethyl)-1,2-benzisoxazol-6-yl]benzamide;

N-cyclopropyl-4-methyl-3-{1-[(1-methylethyl)sulfonyl]-1H-indazol-5-yl}benzamide);

N-cyclopropyl-3-[1-(ethylsulfonyl)-1H-indazol-5-yl]-4-methylbenzamide;

N-cyclopropyl-3-[1-(cyclopropylsulfonyl)-1H-indazol-5-yl]-4-methylbenzamide;
N-cyclopropyl-4-methyl-3-[1-(2-thienylsulfonyl)-1H-indazol-5-yl]benzamide;
3-{1-[(2-cyanophenyl)sulfonyl]-1H-indazol-5-yl}-N-cyclopropyl-4-methylbenzamide;
N-cyclopropyl-3-fluoro-4-methyl-5-[1-(2-thienylsulfonyl)-1H-indazol-5-yl]benzamide;
N-cyclopropyl-3-fluoro-4-methyl-5-[1-(3-thienylsulfonyl)-1H-indazol-5-yl]benzamide;
N-cyclopropyl-3-fluoro-4-methyl-5-{1-[(1-methylethyl)sulfonyl]-1H-indazol-5-yl}benzamide;
N-cyclopropyl-3-fluoro-4-methyl-5-[1-(propylsulfonyl)-1H-indazol-5-yl]benzamide;
N-cyclopropyl-3-fluoro-4-methyl-5-[1-(methylsulfonyl)-1H-indazol-5-yl]benzamide;
3-[1-(butylsulfonyl)-1H-indazol-5-yl]-N-cyclopropyl-5-fluoro-4-methylbenzamide;
N-cyclopropyl-3-[1-(cyclopropylsulfonyl)-1H-indazol-5-yl]-5-fluoro-4-methylbenzamide;
3-{1-[(5-chloro-2-thienyl)sulfonyl]-1H-indazol-5-yl}-N-cyclopropyl-5-fluoro-4-methylbenzamide;
N-cyclopropyl-3-{1-[(3,5-dimethyl-4-isoxazolyl)sulfonyl]-1H-indazol-5-yl}-5-fluoro-4-methylbenzamide;
N-cyclopropyl-3-[1-(ethylsulfonyl)-1H-indazol-5-yl]-5-fluoro-4-methylbenzamide;
3-{1-[(2-chlorophenyl)sulfonyl]-1H-indazol-5-yl}-N-cyclopropyl-5-fluoro-4-methyl benzamide;
N-cyclopropyl-3-fluoro-4-methyl-5-{1-[(2-methylphenyl)sulfonyl]-1H-indazol-5-yl}benzamide;
N-cyclopropyl-3-fluoro-4-methyl-5-[1-(phenylsulfonyl)-1H-indazol-5-yl]benzamide;
N-cyclopropyl-3-{1-[(2,5-difluorophenyl)sulfonyl]-1H-indazol-5-yl}-5-fluoro-4-methylbenzamide;
N-cyclopropyl-3-fluoro-5-{1-[(2-fluorophenyl)sulfonyl]-1H-indazol-5-yl}-4-methylbenzamide;
N-cyclopropyl-3-[1-(cyclopropylmethyl)-1H-indazol-5-yl]-4-methylbenzamide; and
N-cyclopropyl-3-fluoro-4-methyl-5-[3-methyl-1-(2-thienylsulfonyl)-1H-indazol-5-yl]benzamide.

As used herein, the term "alkyl" refers to straight or branched hydrocarbon chains containing the specified number of carbon atoms. For example, $C_{1-6}$alkyl means a straight or branched alkyl containing at least 1, and at most 6, carbon atoms. Examples of "alkyl" as used herein include, but are not limited to, methyl, ethyl, n-propyl n-butyl, n-pentyl, isobutyl, isopropyl and t-butyl. A $C_{1-4}$alkyl group is preferred, for example methyl, ethyl, isopropyl or t-butyl. The said alkyl groups may be optionally substituted with one or more fluorine atoms for example, trifluoromethyl.

As used herein, the term "alkenyl" refers to straight or branched hydrocarbon chains containing the specified number of carbon atoms and containing at least one double bond. For example, $C_{2-6}$alkenyl means a straight or branched alkenyl containing at least 2, and at most 6, carbon atoms and containing at least one double bond. Examples of "alkenyl" as used herein include, but are not limited to ethenyl, 2-propenyl, 3-butenyl, 2-butenyl, 2-pentenyl, 3-pentenyl, 3-methyl-2-butenyl, 3-methylbut-2-enyl, 3-hexenyl and 1,1-dimethylbut-2-enyl.

As used herein, the term "alkoxy" refers to a straight or branched chain alkoxy group, for example, methoxy, ethoxy, propoxy, prop-2-oxy, butoxy, but-2-oxy, 2-methylprop-1-oxy, 2-methylprop-2-oxy, pentoxy, or hexyloxy. A $C_{1-4}$alkoxy group is preferred, for example methoxy or ethoxy.

As used herein, the term "cycloalkyl" refers to a non-aromatic hydrocarbon ring containing the specified number of carbon atoms which may optionally contain up to one double bond. For example, $C_{3-7}$cycloalkyl means a non-aromatic ring containing at least three, and at most seven, ring carbon atoms. Examples of "cycloalkyl" as used herein include, but are not limited to, cyclopropyl, cyclobutyl, cyclopentyl, cyclohexyl and cycloheptyl. A $C_{3-6}$cycloalkyl group is preferred, for example, cyclopropyl, cyclopentyl or cyclohexyl.

As used herein, the terms "heteroaryl ring" and "heteroaryl", unless otherwise defined, refer to a monocyclic 5- to 7-membered unsaturated hydrocarbon ring containing at least one heteroatom independently selected from oxygen, nitrogen and sulfur. Preferably, the heteroaryl ring has five or six ring atoms. Examples of heteroaryl rings include, but are not limited to, furyl, thienyl, pyrrolyl, oxazolyl, thiazolyl, isoxazolyl, isothiazolyl, imidazolyl, pyrazolyl, oxadiazolyl, triazolyl, tetrazolyl, thiadiazolyl, pyridyl, pyridazinyl, pyrimidinyl, pyrazinyl and triazinyl. The said ring may be optionally substituted by one or more substituents independently selected from $C_{1-6}$alkyl and oxy.

As used herein, the terms "heterocyclic ring" or "heterocyclyl", unless otherwise defined refer to a monocyclic 3- to 7-membered saturated hydrocarbon ring containing at least one heteroatom independently selected from oxygen, nitrogen and sulfur. Preferably, the heterocyclyl ring has five or six ring atoms. Examples of heterocyclyl groups include, but are not limited to, pyrrolidinyl, imidazolidinyl, pyrazolidinyl, piperidyl, piperazinyl, morpholino, tetrahydropyranyl, tetrahydrofuranyl, and thiomorpholino. The said ring may be optionally substituted by one or more substituents independently selected from $C_{1-6}$alkyl and oxy.

As used herein, the terms "halogen" or "halo" refer to the elements fluorine, chlorine, bromine and iodine. Preferred halogens are fluorine, chlorine and bromine. A particularly preferred halogen is fluorine or chlorine.

As used herein, the term "solvate" refers to a complex of variable stoichiometry formed by a solute (in this invention, a compound of formula (I) or a salt thereof) and a solvent. Such solvents for the purpose of the invention may not interfere with the biological activity of the solute. Examples of suitable solvents include water, methanol, ethanol and acetic acid. Preferably the solvent used is a pharmaceutically acceptable solvent. Examples of suitable pharmaceutically acceptable solvents include water, ethanol and acetic acid. All such solvates are included within the scope of the present invention.

Certain compounds of formula (I) may exist in stereoisomeric forms (e.g. they may contain one or more asymmetric carbon atoms or may exhibit cis-trans isomerism). The individual stereoisomers (enantiomers and diastereomers) and mixtures of these are included within the scope of the present invention. The present invention also covers the individual isomers of the compounds represented by formula (I) as mixtures with isomers thereof in which one or more chiral centres are inverted. Likewise, it is understood that compounds of formula (I) may exist in tautomeric forms other than that shown in the formula and these are also included within the scope of the present invention.

Salts of the compounds of the present invention are also encompassed within the scope of the invention and may, for example, comprise acid addition salts resulting from reaction of an acid with a basic nitrogen atom present in a compound of formula (I).

Salts encompassed within the term "pharmaceutically acceptable salts" refer to non-toxic salts of the compounds of this invention. Representative salts include the following salts: Acetate, Benzenesulfonate, Benzoate, Bicarbonate, Bisulphate, Bitartrate, Borate, Bromide, Calcium Edetate, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isethionate, Lactate, Lactobionate, Laurate, Malate, Maleate, Mandelate, Mesylate, Methylbromide, Methylnitrate, Methylsulphate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Triethiodide, Trimethylammonium and Valerate. Other salts which are not pharmaceutically acceptable may be useful in the preparation of compounds of this invention and these form a further aspect of the invention.

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the working Examples.

A compound of formula (I) may be prepared by reacting a compound of formula (II)

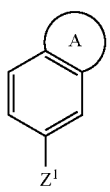

(II)

in which A is as hereinbefore defined and $Z^1$ is halogen, in particular bromine, with a compound of formula (IIIA) or (IIIB)

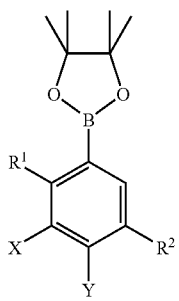

(IIIA)

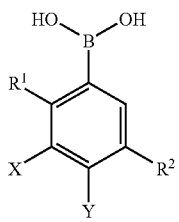

(IIIB)

in which $R^1$, $R^2$, X and Y are as hereinbefore defined, in the presence of a catalyst, for example tetrakis(triphenylphosphine)palladium.

A compound of formula (IIA) may be prepared by, for example, reacting a compound of formula (IV)

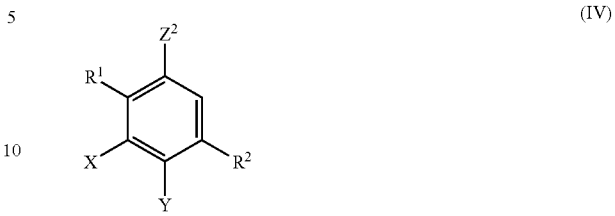

(IV)

in which $R^1$, $R^2$, X and Y are as hereinbefore defined and $Z^2$ is halogen, in particular iodine, with bis(pinnacolato)diboron, [1,1'-bis(diphenylphosphino)ferrocene] dichloropalladium (II) complex ($PdCl_2(ppdf)$) and potassium acetate in a solvent such as DMF.

A compound of formula (IIIB) may be prepared by, for example, reacting a compound of formula (IV) as hereinbefore defined, with n-butyl lithium and triisopropyl borate in a solvent such as TBF.

When $R^2$ is —NH—CO—$R^6$, a compound of formula (IV) may be prepared by reacting an amine of formula (V)

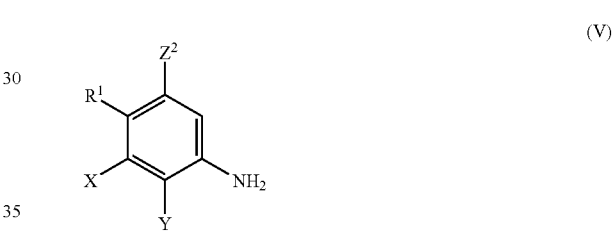

(V)

in which $R^1$, X, Y and $Z^2$ are as hereinbefore defined, with an acid compound of formula (VI)

$R^6CO_2H$ (VI)

in which $R^6$ is as hereinbefore defined, under amide forming conditions.

Suitable amide forming conditions are well known in the art and include adding a base such as DIPEA to a mixture of the amine of formula (V), the acid of formula (VI), and HATU in a solvent such as DMF.

Alternatively, when $R^2$ is —CO—NH—$(CH_2)_q$—$R^7$, a compound of formula (IV) may readily be prepared from a corresponding acid compound of formula (VII)

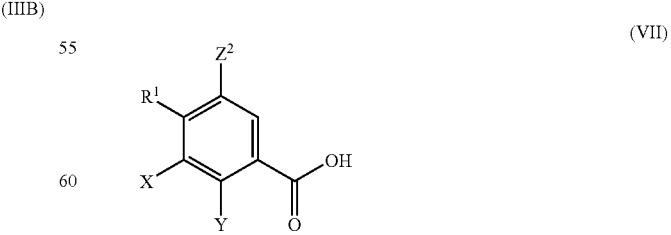

(VII)

in which $R^1$, X, Y and $Z^2$ are as hereinbefore defined, by converting the acid to an activated form of the acid, for example the acid chloride, by treatment with, for example, thionyl chloride, and then reacting the activated acid thus formed with an amine compound of formula (VIII)

R⁷—(CH₂)_q—NH₂    (VIII)

in which R⁷ is as hereinbefore defined, under amide forming conditions.

Suitable amide forming conditions are well known in the art and include treating a solution of the acid of formula (VII), or the activated form thereof, in for example DMF, with an amine of formula (VIII) in the presence of a base such as triethylamine.

For example, one general method for preparing the compounds of formula (I) comprises the reaction set out in Scheme 1 below.

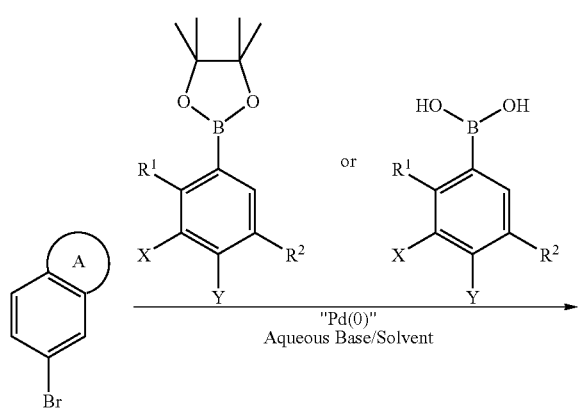

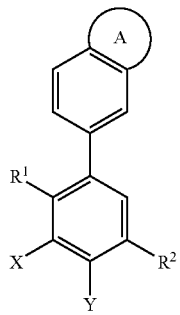

Alternatively, a further general method comprises final stage modification of one compound of formula (I) into another compound of formula (I). Suitable functional group transformations for converting one compound of formula (I) into another compound of formula (I) are well known in the art and are described in, for instance, *Comprehensive Heterocyclic Chemistry II,* eds. A. R. Katritzky, C. W. Rees and E. F. V. Scriven (Pergamon Press, 1996), *Comprehensive Organic Functional Group Transformations,* eds. A. R. Katritzky, O. Meth-Cohn and C. W. Rees (Elsevier Science Ltd., Oxford, 1995), *Comprehensive Organic Chemistry,* eds. D. Barton and W. D. Ollis (Pergamon Press, Oxford, 1979), and *Comprehensive Organic Transformations,* R. C. Larock (VCH Publishers Inc., New York, 1989).

For example, one method for preparing the compounds of formula (I) comprises the reactions set out in Scheme 2 below.

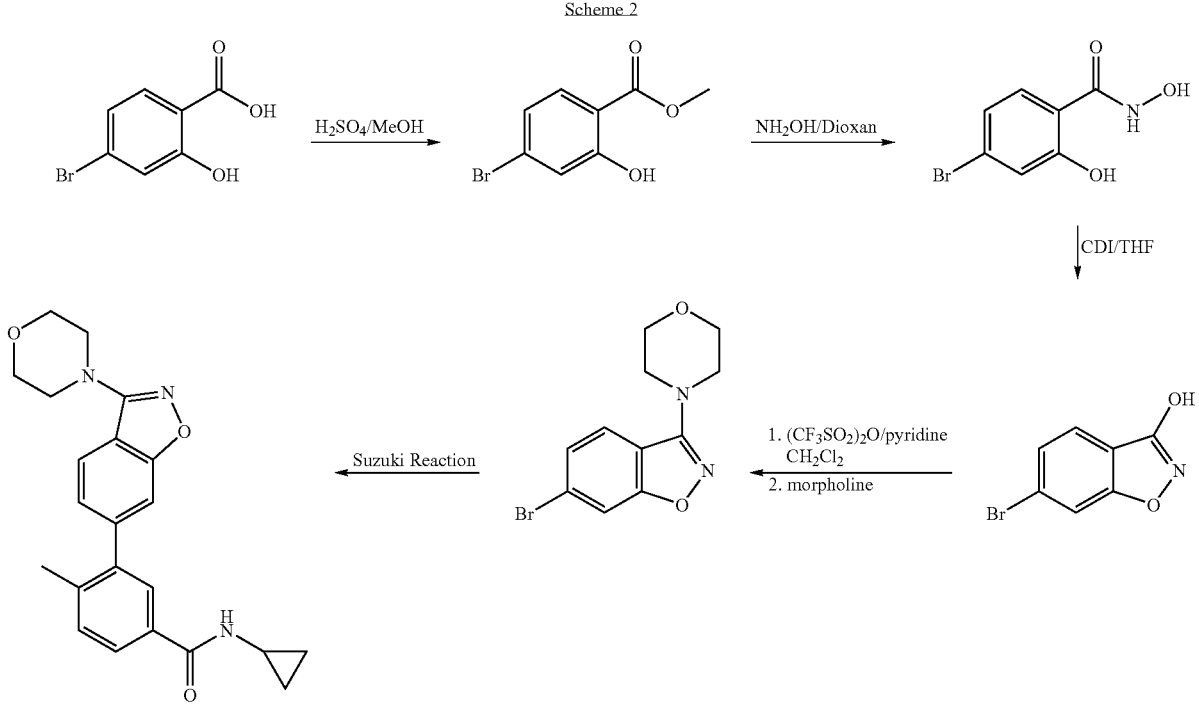

For example, another method for preparing the compounds of formula (I) comprises the reactions set out in Scheme 3 below.

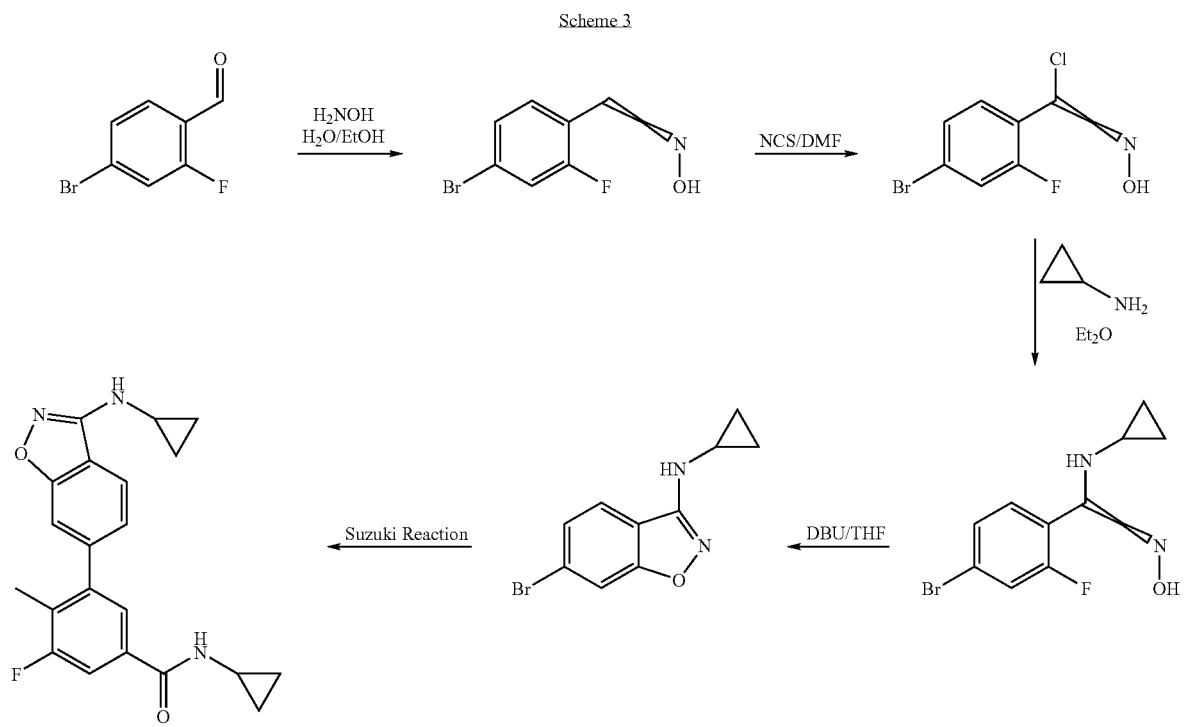

Scheme 3

For example, another method for preparing the compounds of formula (I) comprises the reactions set out in Scheme 4 below.

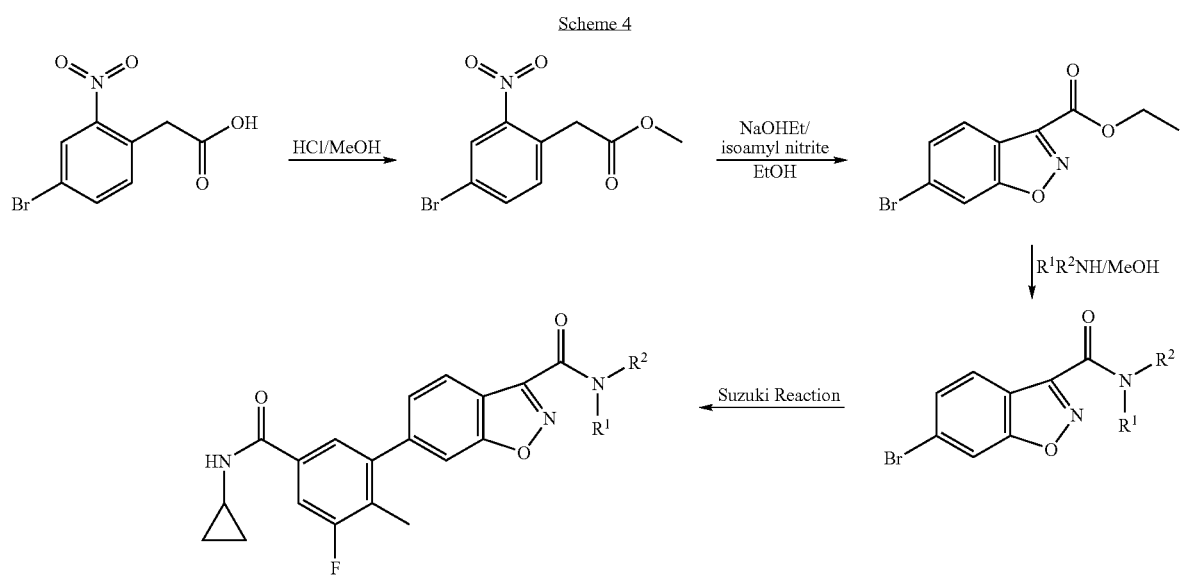

Scheme 4

For example, another method for preparing the compounds of formula (I) comprises the reactions set out in Scheme 5 below.

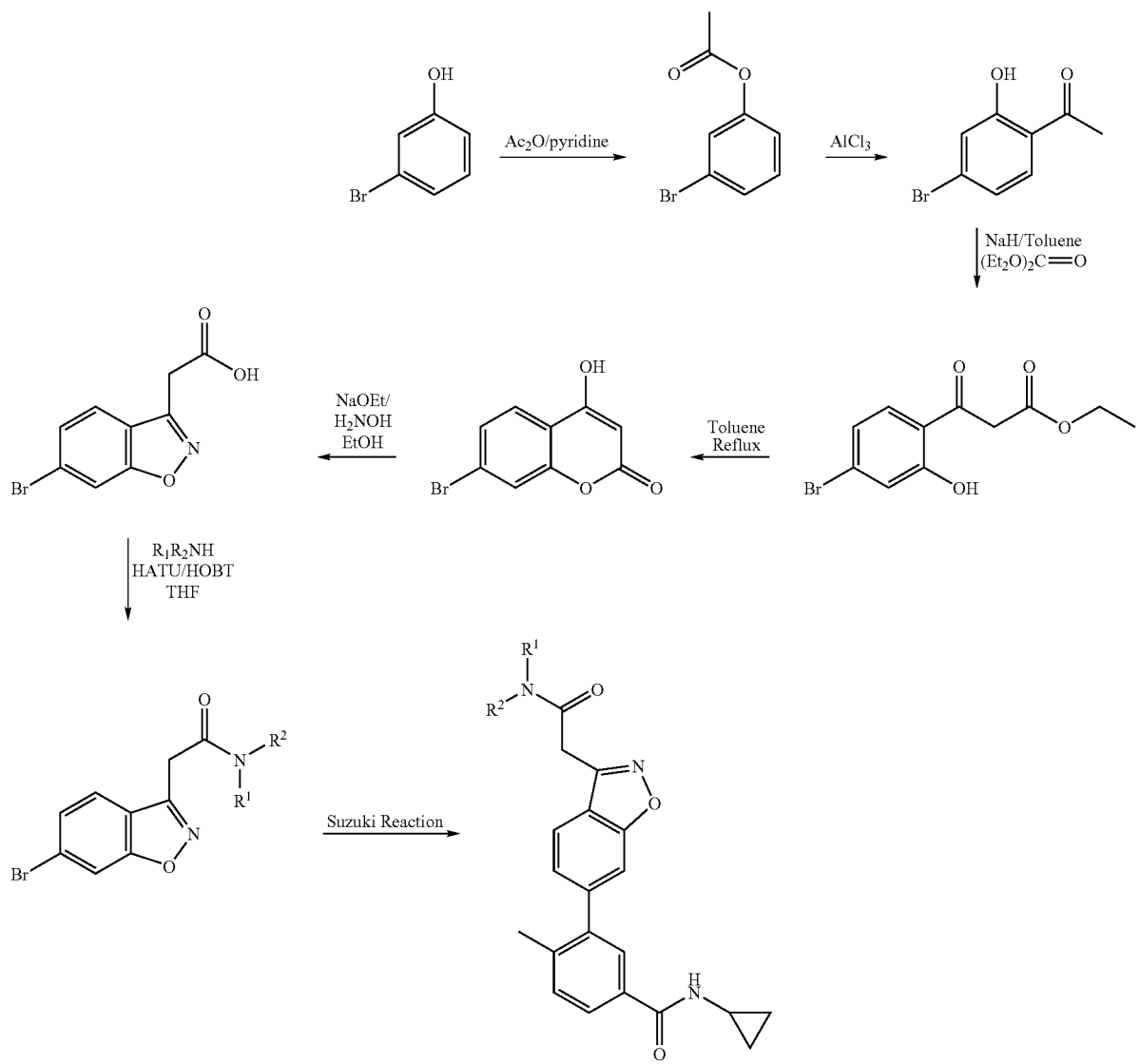
For example, another method for preparing the compounds of formula (I) comprises the reactions set out in Scheme 6 below.
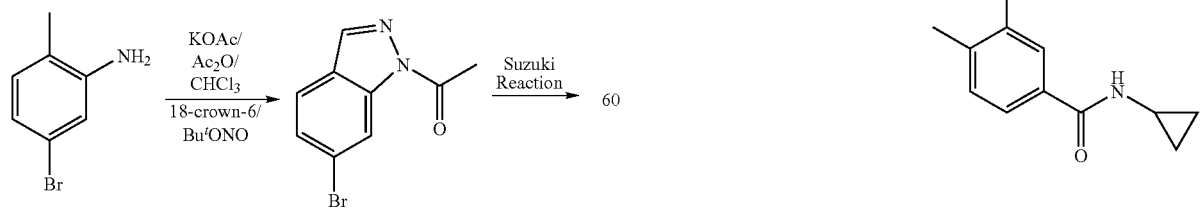
For example, another method for preparing the compounds of formula (I) comprises the reactions set out in Scheme 7 below.

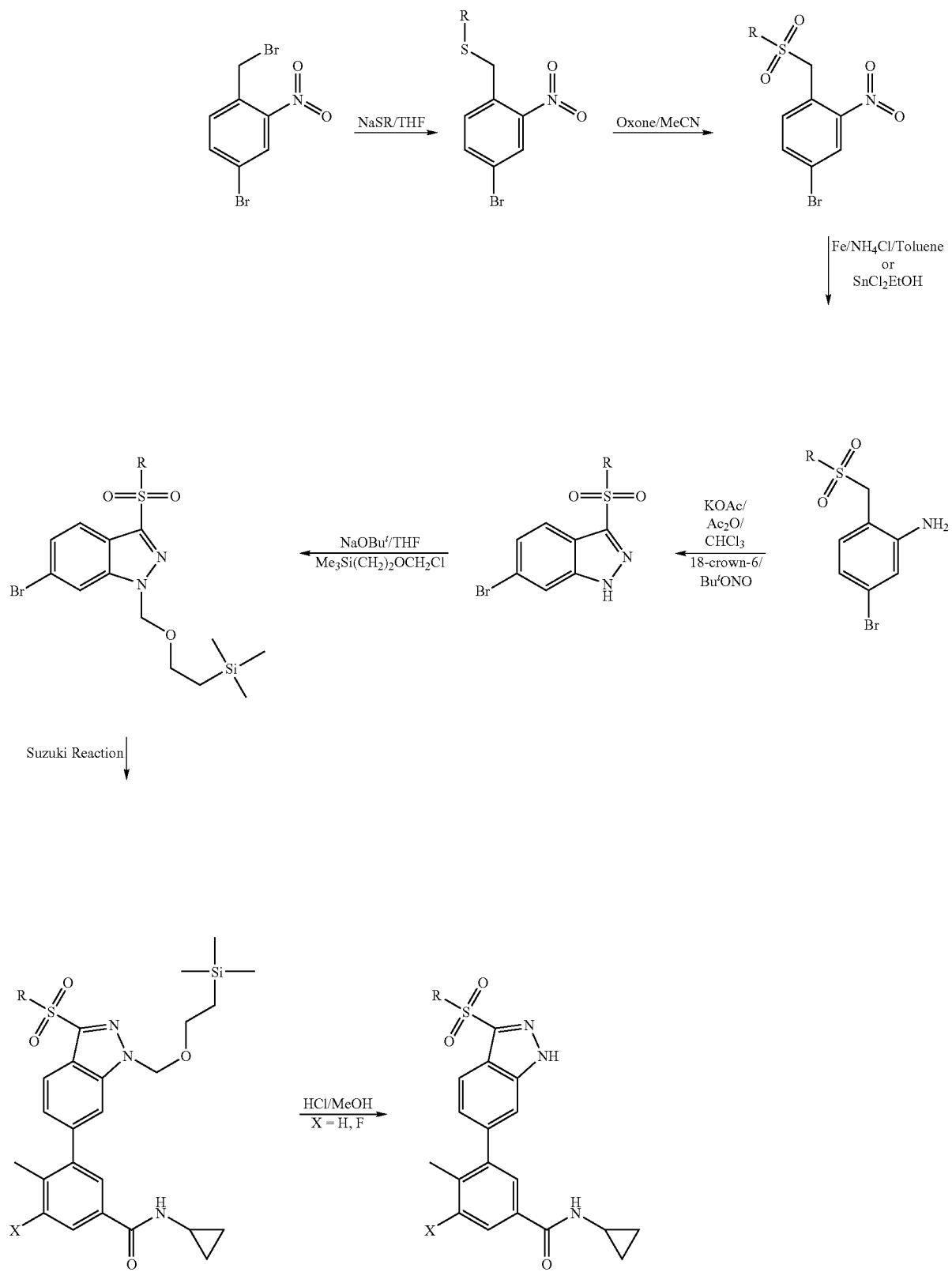

For example, another method for preparing the compounds of formula (I) comprises the reactions set out in Scheme 8 below.

Scheme 8

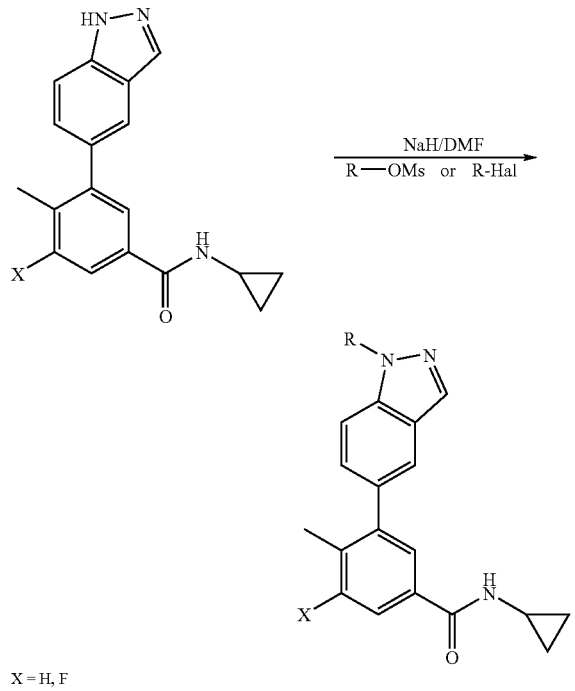

X = H, F

Those skilled in the art will appreciate that in the preparation of the compounds of the invention it may be necessary and/or desirable to protect one or more sensitive groups in the molecule to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P. J. Kocienski (Georg Thieme Verlag 1994). Examples of suitable amino protecting groups include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenyl-methoxycarbonyl (Fmoc), t-butyloxycarbonyl (Boc), isopropyloxycarbonyl, cyclohexyloxycarbonyl) and alkyl type protecting groups (e.g. benzyl, trityl, chlorotrityl). Examples of suitable oxygen protecting groups may include for example alky silyl groups, such as trimethylsilyl or tert-butyldimethylsilyl; alkyl ethers such as tetrahydropyranyl or tert-butyl; or esters such as acetate.

Whilst it is possible for the compounds of the present invention to be administered as the new chemical, the compounds of formula (I) are conveniently administered in the form of pharmaceutical compositions. Thus, in another aspect of the invention, we provide a pharmaceutical composition comprising a compound of formula (I), in admixture with one or more pharmaceutically acceptable carriers, diluents or excipients.

The compounds of formula (I) may be formulated for administration in any suitable manner. They may, for example, be formulated for topical administration or administration by inhalation or, more preferably, for oral, transdermal or parenteral administration. The pharmaceutical composition may be in a form such that it can effect controlled release of the compounds of formula (I). A particularly preferred method of administration, and corresponding formulation, is oral administration.

For oral administration, the pharmaceutical composition may take the form of, and be administered as, for example, tablets (including sub-lingual tablets) and capsules (each including timed release and sustained release formulations), pills, powders, granules, elixirs, tinctures, emulsions, solutions, syrups or suspensions prepared by conventional means with acceptable excipients.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules can be made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the present invention can also be administered in the form of liposome emulsion delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

The present invention includes pharmaceutical compositions containing 0.1 to 99.5%, more particularly, 0.5 to 90% of a compound of the formula (I) in combination with a pharmaceutically acceptable carrier.

Likewise, the composition may also be administered in nasal, ophthalmic, otic, rectal, topical, intravenous (both bolus and infusion), intraperitoneal, intraarticular, subcutaneous or intramuscular, inhalation or insufflation form, all using forms well known to those of ordinary skill in the pharmaceutical arts.

For transdermal administration, the pharmaceutical composition may be given in the form of a transdermal patch, such as a transdermal iontophoretic patch.

For parenteral administration, the pharmaceutical composition may be given as an injection or a continuous infusion (e.g. intravenously, intravascularly or subcutaneously). The compositions may take such forms as suspensions, solutions or emulsions in oily or aqueous vehicles and may contain formulatory agents such as suspending, stabilizing and/or dispersing agents. For administration by injection these may take the form of a unit dose presentation or as a multidose presentation preferably with an added preservative. Alternatively for parenteral administration the active ingredient may be in powder form for reconstitution with a suitable vehicle.

The compounds of the invention may also be formulated as a depot preparation. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

Alternatively the composition may be formulated for topical application, for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration by inhalation the compounds according to the invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, tetrafluoroethane, heptafluoropropane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

The pharmaceutical compositions generally are administered in an amount effective for treatment or prophylaxis of a specific condition or conditions. Initial dosing in human is accompanied by clinical monitoring of symptoms, such symptoms for the selected condition. In general, the compositions are administered in an amount of active agent of at least about 100 µg/kg body weight. In most cases they will be administered in one or more doses in an amount not in excess of about 20 mg/kg body weight per day. Preferably, in most cases, dose is from about 100 µg/kg to about 5 mg/kg body weight, daily. For administration particularly to mammals, and particularly humans, it is expected that the daily dosage level of the active agent will be from 0.1 mg/kg to 10 mg/kg and typically around 1 mg/kg. It will be appreciated that optimum dosage will be determined by standard methods for each treatment modality and indication, taking into account the indication, its severity, route of administration, complicating conditions and the like. The physician in any event will determine the actual dosage which will be most suitable for an individual and will vary with the age, weight and response of the particular individual. The effectiveness of a selected actual dose can readily be determined, for example, by measuring clinical symptoms or standard anti-inflammatory indicia after administration of the selected dose. The above dosages are exemplary of the average case. There can, of course, be individual instances where higher or lower dosage ranges are merited, and such are within the scope of this invention. For conditions or disease states as are treated by the present invention, maintaining consistent daily levels in a subject over an extended period of time, e.g., in a maintenance regime, can be particularly beneficial.

In another aspect, the present invention provides a compound of formula (I) for use in therapy.

The compounds of the present invention are generally inhibitors of the serine/threonine kinase p38 and are therefore also inhibitors of cytokine production which is mediated by p38 kinase. Within the meaning of the term "inhibitors of the serine/threonine kinase p38" are included those compounds that interfere with the ability of p38 to transfer a phosphate group from ATP to a protein substrate according to the assay described below.

It will be appreciated that the compounds of the invention may be selective for one or more of the isoforms of p38, for example p38α, p38β, p38γ and/or p38δ. In one embodiment, the compounds of the invention selectively inhibit the p38α isoform.

In another embodiment, the compounds of the invention selectively inhibit the p38β isoform. In a further embodiment, the compounds of the invention selectively inhibit the p38α and p38β isoforms. Assays for determining the selectivity of compounds for the $p3^8$ isoforms are described in, for example, WO 99/61426, WO 00/71535 and WO 02/46158.

It is known that p38 kinase activity can be elevated (locally or throughout the body), p38 kinase can be incorrectly temporally active or expressed, p38 kinase can be expressed or active in an inappropriate location, p38 kinase can be constitutively expressed, or p38 kinase expression can be erratic; similarly, cytokine production mediated by p38 kinase activity can be occurring at inappropriate times, inappropriate locations, or it can occur at detrimentally high levels.

Accordingly, the present invention provides a method for the treatment of a condition or disease state mediated by p38 kinase activity, or mediated by cytokines produced by the activity of p38 kinase, in a subject which comprises administering to said subject a therapeutically effective amount of a compound of formula (I). The compound may be administered as a single or polymorphic crystalline form or forms, an amorphous form, a single enantiomer, a racemic mixture, a single stereoisomer, a mixture of stereoisomers, a single diastereoisomer or a mixture of diastereoisomers.

The present invention also provides a method of inhibiting cytokine production which is mediated by p38 kinase activity in a subject, e.g. a human, which comprises administering to said subject in need of cytokine production inhibition a therapeutic, or cytokine-inhibiting, amount of a compound of the present invention.

The compound may be administered as a single or polymorphic crystalline form or forms, an amorphous form, a single enantiomer, a racemic mixture, a single stereoisomer, a mixture of stereoisomers, a single diastereoisomer or a mixture of diastereoisomers.

The present invention treats these conditions by providing a therapeutically effective amount of a compound of this invention. By "therapeutically effective amount" is meant a symptom-alleviating or symptom-reducing amount, a cytokine-reducing amount, a cytokine-inhibiting amount, a kinase-regulating amount and/or a kinase-inhibiting amount of a compound. Such amounts can be readily determined by standard methods, such as by measuring cytokine levels or observing alleviation of clinical symptoms. For example, the clinician can monitor accepted measurement scores for anti-inflammatory treatments.

The compounds of the present invention can be administered to any subject in need of inhibition or regulation of p38 kinase or in need of inhibition or regulation of p38 mediated cytokine production. In particular, the compounds may be administered to mammals. Such mammals can include, for example, horses, cows, sheep, pigs, mice, dogs, cats, primates such as chimpanzees, gorillas, rhesus monkeys, and, most preferably, humans.

Thus, the present invention provides methods of treating or reducing symptoms in a human or animal subject suffering from, for example, rheumatoid arthritis, osteoarthritis, asthma, psoriasis, eczema, allergic rhinitis, allergic conjunctivitis, adult respiratory distress syndrome, chronic pulmonary inflammation, chronic obstructive pulmonary disease, chronic heart failure, silicosis, endotoxemia, toxic shock syndrome, inflammatory bowel disease, tuberculosis, atherosclerosis, neurodegenerative disease, Alzheimer's disease, Parkinson's disease, Huntington's disease, amyotrophic lateral sclerosis, epilepsy, multiple sclerosis, aneurism, stroke, irritable bowel syndrome, muscle degeneration, bone resorption diseases, osteoporosis, diabetes, reperfusion injury, graft vs. host reaction, allograft rejections, sepsis, systemic cachexia, cachexia secondary to infection or malignancy, cachexia secondary to aquired immune deficiency syndrome (AIDS), malaria, leprosy, infectious arthritis, leishmaniasis, Lyme disease, glomerulonephritis, gout, psoriatic arthritis, Reiter's syndrome, traumatic arthritis, rubella arthritis, Crohn's disease, ulcerative colitis, acute synovitis, gouty arthritis, spondylitis, and non articular inflammatory conditions, for example, herniated/ruptured/prolapsed intervertebral disk syndrome, bursitis, tendonitis, tenosynovitis, fibromyalgic syndrome and other inflammatory conditions associated with ligamentous sprain and regional musculoskeletal strain, pain, for example that associated with inflammation and/or trauma, osteopetrosis, restenosis, thrombosis, angiogenesis, cancer including breast cancer, colon cancer, lung cancer or prostatic cancer, which comprises administering to said subject a therapeutically effective amount of a compound of formula (I).

A further aspect of the invention provides a method of treatment of a human or animal subject suffering from rheumatoid arthritis, asthma, psoriasis, chronic pulmonary inflammation, chronic obstructive pulmonary disease, chronic heart failure, systemic cachexia, glomerulonephritis, Crohn's disease, neurodegenerative disease, Alzheimer's disease, Parkinson's disease, epilepsy and cancer including breast cancer, colon cancer, lung cancer and prostatic cancer, which comprises administering to said subject a therapeutically effective amount of a compound of formula (I).

A further aspect of the invention provides a method of treatment of a human or animal subject suffering from rheumatoid arthritis, asthma, psoriasis, chronic pulmonary inflammation, chronic obstructive pulmonary disease, chronic heart failure, systemic cachexia, glomerulonephritis, Crohn's disease and cancer including breast cancer, colon cancer, lung cancer and prostatic cancer, which comprises administering to said subject a therapeutically effective amount of a compound of formula (I).

A further aspect of the invention provides a method of treatment of a human or animal subject suffering from rheumatoid arthritis, asthma, chronic pulmonary inflammation, chronic obstructive pulmonary disease, neurodegenerative disease, Alzheimer's disease, Parkinson's disease and epilepsy which comprises administering to said subject a therapeutically effective amount of a compound of formula (I).

A further aspect of the invention provides a method of treatment of a human or animal subject suffering from any type of pain including chronic pain, rapid onset of analgesis, neuromuscular pain, headache, cancer pain, acute and chronic inflammatory pain associated with osteoarthritis and rheumatoid arthritis, post operative inflammatory pain, neuropathic pain, diabetic neuropathy, trigeminal neuralgia, post-hepatic neuralgia, inflammatory neuropathies and migraine pain which comprises administering to said subject a therapeutically effective amount of a compound of formula (I) or a pharmaceutically acceptable salt or solvate thereof.

The compounds of formula (I) may be employed alone or in combination with other therapeutic agents for the treatment of the above-mentioned conditions. In particular, in rheumatoid arthritis therapy, combination with other chemotherapeutic or antibody agents is envisaged. Combination therapies according to the present invention thus comprise the administration of at least one compound of formula (I) and at least one other pharmaceutically active agent. The compound(s) of formula (I) and the other pharmaceutically active agent(s) may be administered together or separately and, when administered separately, this may occur separately or sequentially in any order. The amounts of the compound(s) of formula (I) and the other pharmaceutically active agent(s) and the relative timings of administration will be selected in order to achieve the desired combined therapeutic effect. Examples of other pharmaceutically active agents which may be employed in combination with compounds of formula (I) for rheumatoid arthritis therapy include:

immunosuppresants such as amtolmetin guacil, mizoribine and rimexolone; anti-TNFα agents such as etanercept, infliximab, diacerein; tyrosine kinase inhibitors such as leflunomide; kallikrein antagonists such as subreum; interleukin 11 agonists such as oprelvekin; interferon beta 1 agonists; hyaluronic acid agonists such as NRD-101 (Aventis); interleukin 1 receptor antagonists such as anakinra; CD8 antagonists such as amiprilose hydrochloride; beta amyloid precursor protein antagonists such as reumacon; matrix metalloprotease inhibitors such as cipemastat and other disease modifying anti-rheumatic drugs (DMARDs) such as methotrexate, sulphasalazine, cyclosporin A, hydroxychoroquine, auranofin, aurothioglucose, gold sodium thiomalate and penicillamine.

EXAMPLES

The following Examples are illustrative embodiments of the invention, not limiting the scope of the invention in any way. Reagents are commercially available or are prepared according to procedures in the literature.

LCMS was conducted on a column (3.3 cm×4.6 mm ID, 3 um ABZ+PLUS), at a Flow Rate of 3 ml/min, Injection Volume of 5 µl, at room temperature and UV Detection Range at 215 to 330 nm.

2-Chloroisonicotinic acid, 3-cyanobenzenesulfonyl chloride, 3,4-difluorobenzenesulfonyl chloride, 2,3-dihydro-1-benzofuran-5-sulfonyl chloride and 5-isoxazol-3-ylthiophene-2-sulfonyl chloride may be purchased from Maybridge Chemicals.

3-Iodo-4-methylaniline, 3-fluorobenzenesulfonyl chloride and 4-(trifluoromethyl)benzenesulfonyl chloride may be purchased from Avocado.

3-Methoxyphenylsulfonyl chloride may be purchased from Lancaster.

4-Acetylphenylsulfonyl chloride may be purchased from Acros.

5-Bromoindazole may be prepared by the procedure described in Chem Ber, 1922, 55, 1141.

6-Bromo-3-piperidin-4-yl-1,2-benzisoxazole may be prepared by the procedure described in WO97/49698.

6-Bromo-3-methyl-1,2-benzisoxazole and 5-bromo-3-methyl-1,2-benzisoxazole may be prepared according to the procedures described in Indian J Chem Sect B, 1977, 15B, 1058-1063.

Methyl 4-[(chlorosulfonyl)methyl]benzoate may be prepared by the procedure described in Rec Trav Chim Pays-Bas, 1957, 76, 129.

Intermediate 1

6-Bromo-3-bromomethyl-1,2-benzisoxazole

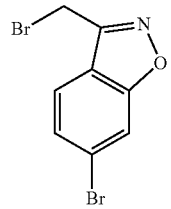

A mixture of 6-bromo-3-methyl-1,2-benzisoxazole (675 mg), N-bromosuccinimide (642 mg) and 1,1'-azobis(cyclohexanecarbonitrile) (90 mg) in carbon tetrachloride (7 ml) was irradiated using a 300W lamp at reflux under nitrogen for 40 h. On cooling the precipitate was removed by filtration, the solvent was evaporated and the residue was purified by flash chromatography on a silica column (4 cm diam) eluting with a cyclohexane-ethyl acetate gradient (49:1 to 24:1) to give the title compound as a pale yellow solid (350 mg).

LC-MS: Rt 3.67 min.

Intermediate 2

2-[(6-Bromo-1,2-benzisoxazol-3-yl)methyl]amino-1, 3-propanediol

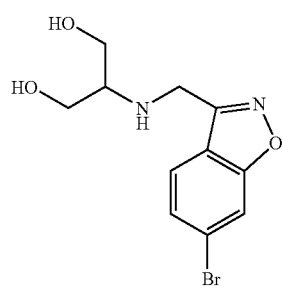

A solution of 6-bromo-3-bromomethyl-1,2-benzisoxazole (Intermediate 1, 130 mg), serinol (50 mg) and DIPEA (0.05 ml) in DMF (0.2 ml) was stirred at 60° under nitrogen for 3 h. The mixture was partitioned between water and ethyl acetate and the organic layer was washed with water and brine, dried through a hydrophobic filter and concentrated. The residue was purified on a Varian Bond Elut SPE cartridge (silica, 2 g) eluting with dichloromethane followed by dichloromethane-methanol (9:1) to give the title compound as a yellow gum (33 mg).

LC-MS: Rt 1.75 min, MH+ 301,303.

Intermediate 3 tert-Butyl 5-bromo-1H-indazole-1-carboxylate

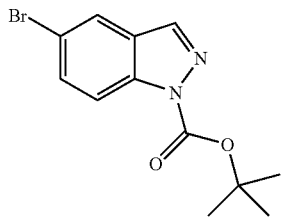

A stirred ice-cold suspension of 5-bromoindazole (2 g, 10.2 mmol), 4-(dimethylamino)pyridine (250 mg, 2.0 mmol) and triethylamine (1.55 ml, 11.2 mmol) in acetonitrile (50 ml) was treated with a solution of di-tert-butyl dicarbonate (2.8 ml, 12.2 mmol) in acetonitrile (20 ml) over 15 min such that the temperature remained under 5°. The reaction mixture was warmed to room temp then stirred for 18 h. The solvent was evaporated and the residue was purified by column chromatography on silica (100 g ) eluting with cyclohexane:ethyl acetate (15:1) to give the title compound (2.27 g, 7.7 mmol).

NMR: δH[CDCl$_3$] 8.10 (1H, s), 8.07 (1H, d), 7.86 (1H, d), 7.60 (1H, dd), 1.71 (9H, s).

LCMS: Rt 3.55 min.

Intermediate 4

4-Methyl-3-(4,4,5,5-tetramethyl-[1,3,2]dioxaborolan-2-yl)benzoic acid

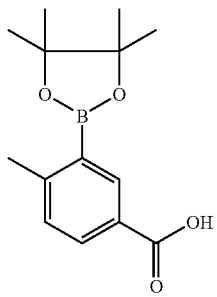

3-Iodo-4-methylbenzoic acid (10 g, 38.16 mmol), bis(pinnacolato)diboron (14.5 g, 57.24 mmol), potassium acetate (18.73 g, 190.8 mmol) and PdCl$_2$dppf (3.12 g, 3.8 mmol) in DMF (200 ml) were heated at 80° C. for 21 hrs. The solvent was evaporated from the cooled reaction under vacuum, the residue dissolved in ethyl acetate (300 ml) and hydrochloric acid (2N, 300 ml) and filtered through celite. The organic phase was separated and the aqueous extracted with ethyl acetate (2×300ml). The combined organic extracts were washed with brine (500 ml) and dried (magnesium sulphate). The solvent was evaporated under vacuum and the residue was absorbed onto silica and applied to a silica column. This was eluted with cyclohexane/ethyl acetate (5:1). to give the title compound.

NMR: δH [d6-DMSO] 12.83, (1H, b), 8.23, (1H, d), 7.89, (1H, dd), 7.29, (1H, d), 2.51, (3H, s), 1.30, (12H, s).

LCMS: Rt 3.65 min.

Intermediate 5

N-Cyclopropyl-4-methyl-3-(4,4,5,5-tetramethyl-1,3,2-dioxaborolan-2-yl)benzamide

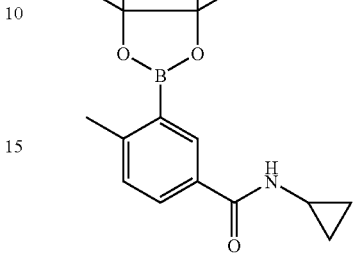

Intermediate 4 (10 g) was dissolved in DMF (100 ml). To this was added cyclopropylamine (2.2 g) DIPEA (15 ml) and HATU (14 g). The mixture was stirred for 3 hours at room temp. The solvent was removed under vacuum and the residue was partitioned between ethyl acetate (400 ml) and saturated sodium bicarbonate solution (400 ml). The organic layer was dried over magnesium sulphate, filtered and concentrated under vacuum to give a pink solid. The product was purified using Biotage chromatography on silica eluting with 50:50 ethylacetate/cyclohexane to give the title compound as a white solid.

NMR: δH [d6-DMSO] 8.42 (1H, d), 8.06 (1H, d), 7.77 (1H, dd), 7.23 (1H, d), 2.85 (1H, m), 2.47 (3H, s), 1.32 (12H, s), 0.67 (2H, m), 0.56 (2H, m).

LCMS: Rt 3.29 min, MH$^+$ 302.

Intermediate 6

3-Iodo-4-methylbenzoyl chloride

Thionyl chloride (8.2 ml) was added to a mixture of 3-ioso-4-methylbenzoic acid (18.5 g) in chloroform (100 ml) and heated at 61° C. for 16 hours. The solvent was removed under vacuum and excess thionyl chloride removed by azeotroping with toluene (3×30 ml). The title compound was formed as a beige solid (19.5 g) and used in subsequent reactions without further purification.

NMR: δH [d6-DMSO] 8.31 (1H, d), 7.87 (1H, dd), 7.46 (1H, d), 2.43 (3H, s).

Intermediate 7

4-(3-Nitrophenyl)morpholine

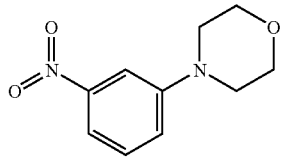

3-Fluoronitrobenzene (10 g) was added to a solution of morpholine (34 ml) in DMSO (120 ml) and heated at 110° C. for 60 h. The reaction mixture was cooled and poured onto water (800 ml). The precipitate was collected by filtration and the orange solid was dried under vacuum and used in subsequent reactions without further purification (13.7 g).

NMR: δH [d6-DMSO] 7.68 (1H, dd), 7.62 (1H, dd), 7.49 (1H, t), 7.42 (1H, dd), 3.76 (4H, dd), 3.24 (4H, dd).

Intermediate 8

3-(4-Morpholinyl)benzenamine

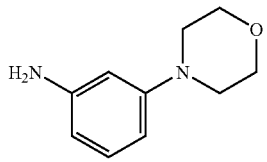

A flask containing 5% palladium on carbon (1.95 g) was evacuated and refilled with hydrogen. 4-(3-Nitrophenyl)morpholine (intermediate 7) (19.5 g) was introduced into the flask as a solution in ethanol and DMF (100 ml, 4:1 v/v). The reaction was stirred at room temp until further uptake of hydrogen ceased (after approximately 7 L). The reaction was then filtered through celite and solvent was removed under vacuum to give the title compound (12.6 g) as a beige solid.

NMR: δH [d6-DMSO] 6.85 (1H, t), 6.12 (2H, m), 6.06 (1H, dd), 4.88 (2H, brs), 3.70 (4H, apparent t), 2.98 (4H, apparent t).

LCMS: Rt 1.08 min MH$^+$179.

Intermediate 9

3-Iodo-4-methyl-N-[3-(4-morpholinyl)phenyl]benzamide

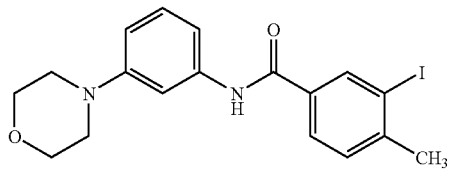

3-Iodo-4-methylbenzoyl chloride (Intermediate 6) (19.5 g) was added portion-wise to a mixture of triethylamine (48 ml) and 3-(4-morpholinyl)benzenamine (Intermediate 8) (12.6 g) in DMF (150 ml) and the mixture was heated at 80° C. for 16 h. The solvent was removed under vacuum and the residue was dissolved in chloroform (200 ml). The organic layer was washed with water (2×100 ml), 2M sodium hydroxide solution (100 ml) and brine (100 ml), dried over magnesium sulphate, filtered and concentrated under vacuum The resulting yellow solid was triturated with diethyl ether and collected by filtration to yield the title compound as an off-white solid (20.0 g). The product was used in subsequent reactions without further purification.

NMR: δH [d6-DMSO] 10.10 (1H, s), 8.39 (1H, d), 7.90 (1H, dd), 7.49 (1H, d), 7.38 (1H, t), 7.28 (1H, brd), 7.19 (1H, t), 6.71 (1H, dd), 3.75 (4H, apparent t), 3.10 (4H, apparent t), 2.44 (3H, s).

LCMS: Rt 3.52 min MH$^+$423.

Intermediate 10

4-Methyl-N-[3-(4-morpholinyl)phenyl]-3-(4,4,5,5-tetramethyl-[b 1,3,2]-dioxaborolan-2-yl)benzamide

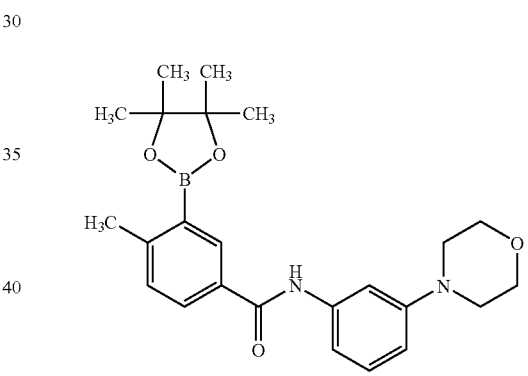

3-Iodo-4-methyl-N-[3-(4-morpholinyl)phenyl]benzamide (Intermediate 9) (8.00 g) triethylamine (7.9 ml) and bis(pinacolato)diboron (4.13 ml) were added to a solution of PdCl$_2$dppf (770 mg) in dioxane (100 ml) and the mixture was heated at 80° under nitrogen for 3 h. The reaction was cooled, the solvent was removed under vacuum and the residue was dissolved in dichloromethane (150 ml). The solution was washed with water (100 ml×3) and brine (100 ml) dried (magnesium sulphate) and the solvent was removed under vacuum. The residue was purified by column chromatography on silica eluting with 30% ethyl acetate/cyclohexane to 50% ethyl acetate/cyclohexane to give the title compound as a white solid (4.05 g).

NMR: δH [d6-DMSO] 10.11 (1H, s), 8.19 (11, d), 7.93 (1H, dd), 7.40 (1H, brs), 7.33 (1H, d), 7.28 (1H, brd), 7.19 (1H, t), 6.70 (1H, dd), 3.75 (4H, apparent t), 3.09 (4H, apparent t), 2.54 (3H, s), 1.33 (12H, s).

LCMS: Rt 3.65 min MH$^+$423.

Intermediate 11

2-Chloro-N-(3-iodo-4-methylphenyl)-isonicotinamide

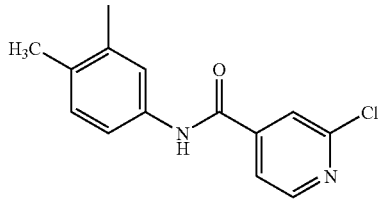

2-Chloroisonicotinic acid (3.3 g) HATU (8.75 g) DIPEA (10.9 ml) and 3-iodo-4-methylaniline (5.00 g) in DMF (50 ml) were heated under nitrogen for 16 h. The reaction was cooled, the solvent was removed under vacuum and the residue was dissolved in dichloromethane (150 ml). The solution was washed with water (3×100 ml) and brine (100 ml) dried (magnesium sulphate) and the solvent was removed under vacuum. The residue was purified by column chromatography on silica eluting with ethyl acetate/cyclohexane (40:60) to give the title compound as a white solid (7.00 g).

NMR: δH [d6-DMSO] 10.52 (1H, s), 8.62 (1H, d), 8.29 (1H, d), 7.99 (1H, b), 7.87 (1H, dd), 7.70 (1H, dd), 7.34 (1H, d), 2.36 (3H, s).

LCMS: Rt 3.59 min MH+373.

Intermediate 12

N-(3-Iodo-4-methylphenyl)-2-pyrrolidin-1-yl-isonicotinamide

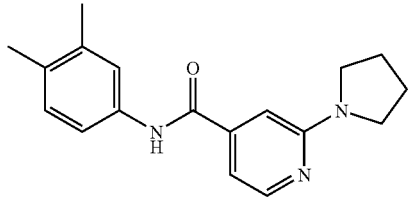

A solution of N-(3-iodomethylphenyl)-2-chloro-isonicotinamide (Intermediate 11) (7.00 g) in pyrrolidine (20 ml) was heated at 80° C. under nitrogen for 16 h. Excess pyrrolidine was removed under vacuum and the residue was triturated with diethyl ether (20 ml). The resulting solid was collected by filtration and dried under vacuum to give the title compound as a pale yellow solid (7.73 g).

NMR: δH [d6-DMSO] 10.29 (1H, s), 8.29 (1H, d), 8.20 (1H, d), 7.71 (1H, dd), 7.72 (1H, dd), 6.97 (1H, brd), 6.88 (1H, b), 3.45 (2H, apparent t), 3.09 (2H, m), 2.35 (3H, s), 1.98 (2H, m), 1.82 (2H, m).

LCMS: Rt 2.77 min MH+408.

Intermediate 13

N-[4-Methyl-3-(4,4,5,5-tetramethyl-[1,3,2]-dioxaborolan-2-yl)phenyl]-2-(1-pyrrolidinyl)-4-pyridinecarboxamide

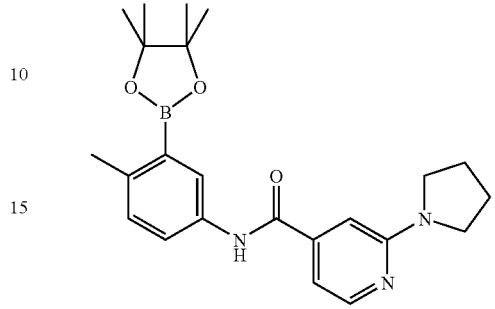

Bis(pinacolato)diborane (7.24 g) was added to a mixture of N-(3-iodo-4-methylphenyl)-2-pyrrolidin-1-yl-isonicotinamide (Intermediate 12) (7.73 g) potassium acetate (9.32 g, 95 mmol) and PdCl₂dppf (770 mg) in DMF (100 ml and the reaction was heated at 80° under nitrogen for 16 h. The reaction was cooled and the solvent was removed under vacuum. The residue was dissolved in chloroform (150 ml), washed with water (3×100 ml) and brine (100 ml), dried (magnesium sulphate) and the solvent was removed under vacuum. The residue was purified by column chromatography on silica eluting with ethyl acetate:cyclohexane (1:4) to (1:1) to give the title compound as a white solid (1.5 g).

NMR: δH (CDCl₃) 8.27 (1H, d), 7.99 (1H, dd), 7.76 (1H, b), 7.65 (1H, d), 6.20 (1H, d), 6.82 (1H, b), 6.77 (1H, b), 3.52 (4H, apparent t), 2.52 (3H, s), 2.25 (4H, m), 1.35 (12H, s).

LCMS: Rt 2.90 min MH+408.

Intermediate 14

N-(3-Iodo-4-methylphenyl)thiophene-3-amide

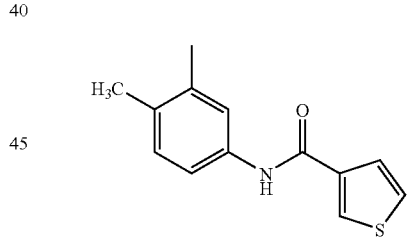

Thiophene-3-carboxylic acid (2.75 g) and HATU (8.15 g) in DMF (25 ml) were stirred at room temp for 15 min. HOBT (2.9 g), 3-iodomethylaniline (5.0 g) and DIPEA (11.2 ml, 64.35 mmol) were added and the reaction was stirred at room temp for 16 h. The solvent was evaporated under vacuum and the residue was partitioned between ethyl acetate (100 ml) and aqueous sodium carbonate (10%, 100 ml). The aqueous layer was extracted with ethyl acetate (50 ml) and the combined organic phases washed with hydrochloric acid (2N, 75 ml), water (75 ml) and brine (75 ml). The organic phase was dried (magnesium sulphate) and absorbed onto silica. The silica was applied to a silica column and eluted with cyclohexane/ethyl acetate (4:1). The solvent was evaporated from the product fractions under vacuum to the tide compound.

NMR: δH [d6-DMSO] 10.06, (1H, b), 8.34, (1H, m), 8.29, (1H, d), 7.70, (1H, dd), 7.66, (1H, dd), 7.62, (1H, dd), 7.30, (1H, dd), 2.34, (3H, s).

LCMS: Rt 3.69 min, MH+ 344.

Intermediate 15

N-[4-Methyl-3-(4,4,5,5-tetramethyl-[1,3,2]dioxaborolan-2-yl)-phenyl]thiophene-3-amide

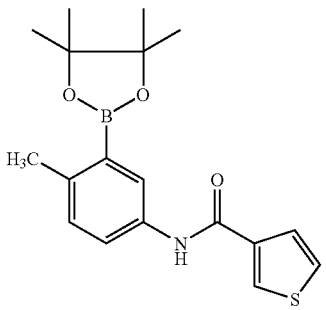

N-(3-Iodo-4-methylphenyl)thiophene-3-amide (Intermediate 14) (2.64 g) bis(pinnacolato)diboron (2.13 g), potassium acetate (825 mg) and PdCl$_2$dppf (312 mg) in DMF (20 ml) were heated at 80° C. for 20 h. The cooled reaction was absorbed onto silica and applied to a Varian Bond-Elut SPE cartridge (silica, 10 g) and eluted with a cyclohexane/ethyl acetate gradient. The product fractions were concentrated under vacuum to give the title compound.

NMR: δH [d6-DMSO] 9.99, (1H, b), 8.35, (1H, s), 7.90, (1H, d), 7.85, (1H, dd), 7.63, (2H, m), 7.14, (1H, d), 2.42, (3H, s), 1.30, (12H, s).

LCMS: Rt 3.65 min, MH$^+$344.

Intermediate 16

N-(3-Iodo-4-methylphenyl)-3-furamide

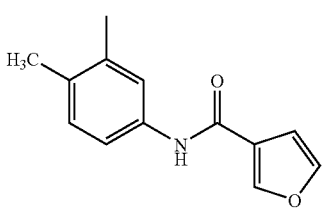

3-Furoic acid (2.4 g) and HATU (8.15 g) in DMF (25 ml) were stirred at room temperature for 15 min. HOBT (2.9 g), 3-iodomethylaniline (5.0 g) and DIPEA (11.2 ml) were added and the mixture was stirred at room temp for 16 h. The solvent was evaporated under vacuum and the residue was partitioned between ethyl acetate (100 ml) and aqueous sodium carbonate (10%, 100 ml). The aqueous layer was extracted with ethyl acetate (50 ml) and the combined organic phases were washed with hydrochloric acid (2N, 75 ml), water (75 ml) and brine (75 ml). The organic phase was dried (magnesium sulphate) and absorbed onto silica. The silica was applied to a silica column and eluted with cyclohexane/ethyl acetate (3:1) to give the title compound.

NMR: δH [d6-DMSO] 9.92, (1H, b), 8.36, (1H, d), 8.23, (1H, d), 7.80, (1H, t), 7.66, (1H, dd), 7.29, (1H, d), 6.98, (1H, d), 2.33, (3H, s).

LCMS: Rt 3.52 min, MH$^+$ 328.

Intermediate 17

N-[4-Methyl-3-(4,4,5,5-tetramethyl-[1,3,2]dioxaborolan-2-yl)-phenyl]-3-furamide

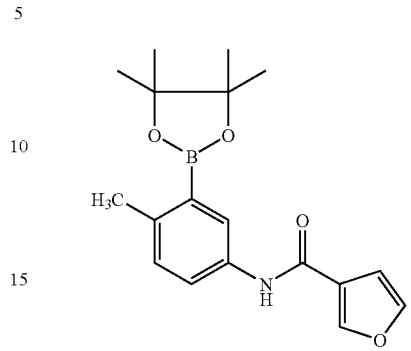

N-(3-Iodo-4-methylphenyl)-3-furamide (Intermediate 16) (2.5 g) bis(pinnacolato)diboron (2.13 g) potassium acetate (825 mg) and PdCl$_2$dppf (312 mg) in DMF (20 ml) were heated at 80° for 20 h. The cooled reaction was absorbed onto silica and applied to a Varian Bond-Elut SPE cartridge (silica, 10 g) and eluted with a cyclohexane/ethyl acetate gradient. The product fractions were concentrated under vacuum to give the title compound.

NMR: δH [d6-DMSO] 9.86, (1H, b), 8.36, (1H, m), 7.86-7.82, (2H, m), 7.77, (1H, t), 7.14, (1H, d), 6.99, (1H, m), 2.41, (3H, s), 1.30, (12H, s).

LCMS: Rt 3.55 min, MH$^+$ 328.

Intermediate 18

4-Methyl-3-(4,4,5,5-tetramethyl-[1,3,2]dioxaborolan-2yl)-N-(thiazol-2-yl)-benzamide

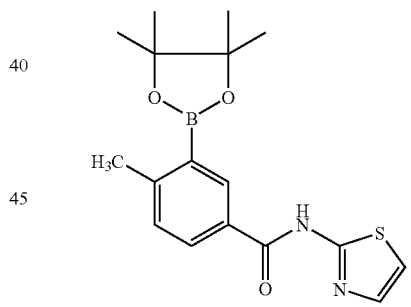

4-Methyl-3-(4,4,5,5-tetramethyl-[1,3,2]dioxaborolan-2-yl)-benzoic acid (Intermediate 4) (2.0 g) DIPEA (4-ml) and HATU (3.05 g) were dissolved in DMF (20 ml) and stirred at room temp for 15 min. 2-Aminothiazole (801 mg) was added and the mixture was stirred at room temp for 18 h. The solvent was evaporated under vacuum and the residue was partitioned between ethyl acetate (250 ml) and water (50 ml). The organic phase was washed with hydrochloric acid (2N, 50 ml) and aqueous sodium bicarbonate (1M, 50 ml) dried (magnesium sulphate) concentrated under vacuum. The residue was absorbed onto silica and purified by flash column chromatography eluting with cyclohexanelethyl acetate (4: 1) to give the title compound (1.72 g).

NMR: δH [d6-DMSO] 12.65, (1H, b), 8.32, (1H, d), 8.08, (1H, dd), 7.56, (1H, d), 7.35, (1h, d), 7.28, (1H, d), 2.54, (3H, s), 1.34, (12H, s).

LCMS: Rt 3.66 min, MH$^+$ 345.

Intermediate 19

N-(3-Methoxy-phenyl)-4-methyl-3-(4,4,5,5-tetramethyl-[1,3,2]dioxaborolan-2-yl)-benzamide

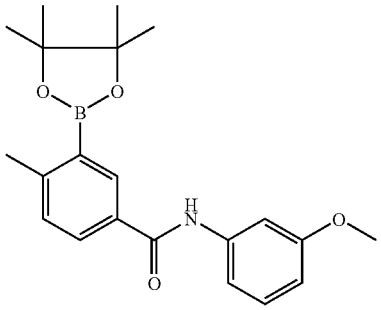

4-Methyl-3-(4,4,5,5-tetramethyl-[1,3,2]dioxaborolan-2-yl)-benzoic acid (Intermediate 4) (2 g) was dissolved in DMF (20 ml). To this was added 3-methoxyaniline (0.985 g), DIPEA (4 ml) and HATU (3.05 g). The mixture was stirred for 18 h at room temp. The solvent was removed under vacuum and the residue was partitioned between ethyl acetate (250 ml) and water (50 ml). The organic layer was dried (magnesium sulphate) concentrated under vacuum and purified using a silica Biotage cartridge (90 g) eluting with 1:4 ethyl acetate/cyclohexane to give the title compound as a white solid (2.06 g).

NMR: δH [d6-DMSO] 10.20, (1H, s), 8.17, (1H, s), 7.94-7.91, (1H, dd), 7.45, (1H, s), 7.36-7.32, (2H, t), 7.25-7.21, (1H, t), 6.68-6.65, (1H, dd), 3.74, (3H, s), 2.53, (3H, s), 1.32, (12H, s).

LCMS: Rt 3.80 min, MH+ 368.

Intermediate 20

4-Methyl-3-(4,4,5,5-tetramethyl-[1,3,2]dioxaborolan-2-yl)-N-([1,3,4]thiadiazol-2-yl)-benzamide

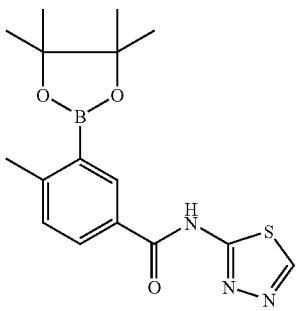

4-Methyl-3-(4,4,5,5-tetramethyl-[1,3,2]dioxaborolan-2-yl)-benzoic acid (Intermediate 4) (2.0 g), DIPEA (4 ml) and HATU (3.05 g) were dissolved in DMF (20 ml) and stirred at room temp for 15 min. 2-Aminothiadiazole (810 mg) was added and the mixture was stirred at room temp for 18 h. The solvent was evaporated under vacuum and the residue was partitioned between ethyl acetate (250 ml) and hydrochloric acid (2N, 150 ml). The aqueous phase was extracted with ethyl acetate (2×250 ml). The combined organic extracts were dried (magnesium sulphate) and the solvent was removed under vacuum. The residue was absorbed onto silica and purified by flash column chromatography eluting with cyclohexane/ethyl acetate (4:1 then 1:1) to give the title compound (0.95 g).

NMR: δH [d6-DMSO] 13.08, (1H, b), 9.22, (1H, s), 8.35, (1H, d), 8.11, (1H, dd), 7.38, (1H, d), 2.55, (3H, s), 1.34, (12H, s).

LCMS: Rt 3.34 min, MH+ 346.

Intermediate 21

N-Cyclopropylmethyl-4-methyl-3-(4,4,5,5-tetramethyl-[1,3,2]dioxaborolan-2-yl)-benzamide

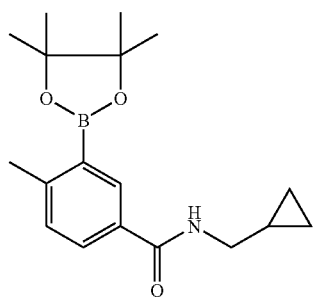

4-Methyl-3-(4,4,5,5-tetramethyl-[1,3,2]dioxaborolan-2-yl)-benzoic acid (Intermediate 4) (2.0 g) DIPEA (4-ml) and HATU (3.05 g) were dissolved in DMF (20 ml) and stirred at room temp for 15 min. Cyclopropylmethylamine (568 mg) was added and the mixture was stirred at room temp for 18 h. The solvent was removed under vacuum and the residue was partitioned between ethyl acetate (250 ml) and water (50 ml). The organic phase was washed with hydrochloric acid (2N, 50 ml) and aqueous sodium bicarbonate (1M, 50 ml) dried (magnesium sulphate) and concentrated under vacuum. The residue was absorbed onto silica and purified by flash column chromatography eluting with cyclohexane/ethyl acetate (4:1) to give the title compound (1.73 g).

NMR: δH [d6-DMSO] 8.54, (1H, t), 8.11, (1H, d), 7.82, (1H, dd), 7.26, (1H, d), 3.12, (2H, t), 1.32, (12H, s), 1.03, (1H, m), 0.42, (2H, m), 0.22, (2H, m).

LCMS: Rt 3.47 min, MH+ 316.

Intermediate 22

Methyl 4-bromo-2-hydroxybenzoate

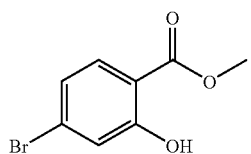

A solution of 4-bromo-2-hydroxybenzoic acid (1.0 g) in methanol (10 ml) was treated cautiously with conc. sulphuric acid (0.5 ml) then stirred at 75° under nitrogen for 7 h. The mixture was concentrated under vacuum and the residue was partitioned between ethyl acetate (30 ml) and water (30 ml). The aqueous layer was re-extracted with ethyl acetate (30 ml) and the combined organic extracts were washed with saturated aqueous sodium bicarbonate (2×50 ml) and water (50 ml). The dried (MgSO4) extracts were concentrated under vacuum to give the title compound as a beige solid (0.7 g).

LCMS: Rt 3.42 min.

Intermediate 23

4-Bromo-N,2-dihydroxybenzamide

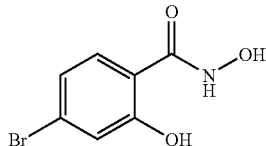

A solution of methyl 4-bromo-2-hydroxybenzoate (Intermediate 22) (0.7 g) in dioxan (5 ml) was added dropwise to a solution of hydroxylamine hydrochloride (0.32 g) and sodium hydroxide (0.42 g) in water (10 ml) then stirred at room temp. for 18 h. The dioxan was removed under vacuum and the residue was stirred with 2N hydrochloric acid to give a precipitate which was collected by filtration, washed with water and dried to give the title compound as an off-white solid (0.63 g).

LCMS: Rt 2.64 min.

Intermediate 24

6-Bromo-1,2-benzisoxazol-3 (2H)-one

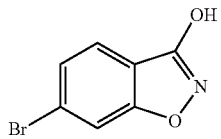

A solution of carbonyldiimidazole (0.75 g) in dry tetrahydrofuran (15 ml) was added to a refluxing solution of 4-bromo-N,2-dihydroxybenzamide (Intermediate 23) (0.56 g) in dry tetrahydrofuran (10 ml) then stirred for 2 h. The solvent was removed under vacuum, the residue was suspended in water and 2N hydrochloric acid (10 ml) was added. The resulting precipitate was collected by filtration, washed with water then cyclohexane and dried to give the title compound as a cream solid (0.37 g).

LCMS: Rt 3.30 min.

Intermediate 25

1,1-Dimethylethyl 4-(6-bromo-1,2-benzisoxazol-3-yl)-1-piperazinecarboxylate

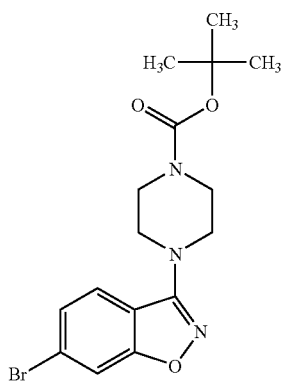

An ice-bath cooled solution of 6-bromo-1,2-benzisoxazol-3 (2H)-one (Intermediate 24) (0.05 g) and dry pyridine (0.05 ml) in dry dichloromethane (4 ml) was stirred under nitrogen and treated with triflic anhydride (60 µL). The solution was stirred at room temp. for 4 h, diluted with cyclohexane then applied to a Varian Bond-Elut SPE cartridge (silica, 1 g) and eluted with dichloromethane to give a yellow oil. The oil was dissolved in acetonitrile (2 ml) treated with 1,1-dimethylethyl 1-piperazinecarboxylate (0.04 g) and diisopropylethylamine (0.05 ml) then stirred at 70° under nitrogen for 20 h. The cooled reaction mixture was purified on a Varian Bond-Elut SPE cartridge (silica, 5 g) using dichloromethane:methanol to give the title compound as a white solid (0.016 g).

LCMS: Rt 3.62 min.

Intermediate 26

1,1-Dimethylethyl 4-(6-{5-[(cyclopropylamino)carbonyl]-2-methylphenyl}-1,2-benzisoxazol-3-yl)-1-piperazinecarboxylate

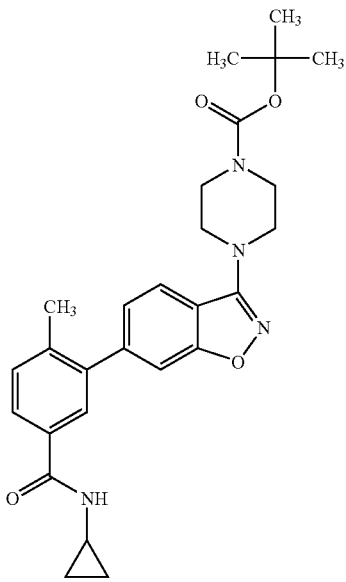

A mixture of 1,1-dimethylethyl 4-(6-bromo-1,2-benzisoxazol-3-yl)-1-piperazinecarboxylate (Intermediate 25) (0.04 g), N-Cyclopropyl-4-methyl-3-(4,4,5,5-tetramethyl-1,3,2-dioxaborolan-2-yl)benzamide (Intermediate 5) (0.035 g), 2N aqueous sodium carbonate (2 ml) and tetrakis(triphenylphosphine)palladium(0) (1 mg) in isopropanol (6 ml) was stirred at reflux under nitrogen for 16 h. The residue was absorbed onto silica Merck 7734) and applied to a Varian Bond-Elut SPE cartridge (silica, 5 g). Elution with dichloromethane:methanol (98:2) gave the title compound as a cream solid (0.03 g).

LCMS: Rt 3.50 min.

Intermediate 27

6-Bromo-3-(4-morpholinyl)-1,2-benzisoxazole

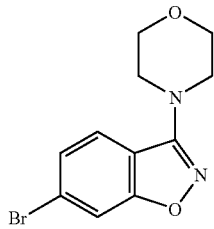

An ice-bath cooled solution of 6-bromo-1,2-benzisoxazol-3(2H)-one (Intermediate 24) (0.15 g) and dry pyridine (0.15 ml) in dry dichloromethane (12 ml) was stirred under nitrogen and treated with triflic anhydride (180 μL). The solution was stirred at room temp. for 90 min, diluted with cyclohexane then applied to a Varian Bond-Elut SPE cartridge (silica, 5 g) and eluted with cyclohexane and dichloromethane to give a colourless oil. The oil was dissolved in acetonitrile (4 ml) treated with morpholine (61 μL) and diisopropylethylamine (0.15 ml) then stirred at 70° under nitrogen for 16 h. The cooled reaction mixture was purified on a Varian Bond-Elut SPE cartridge (silica, 5 g) using dichloromethane:ethanol:0.88 ammonia to give the title compound as a white solid (0.03 g).

LCMS: Rt 3.01 min.

Intermediate 28

3-Bromophenyl acetate

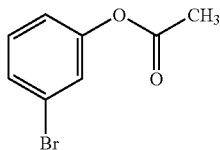

Acetic anhydride was added dropwise to an ice-cold solution of 3-bromophenol (25.5 g) in pyridine (25 ml) and the solution was then stirred at room temp. for 4 h. 2N Hydrochloric acid (160 ml) was added and the mixture was extracted with ether (×2). The combined organic extracts were washed with water and brine, dried (MgSO$_4$) and concentrated under vacuum to give the title compound as a brown liquid (30.8 g).

LCMS: Rt 3.0 min.

Intermediate 29

1-(4-Bromo-2-hydroxyphenyl)ethanone

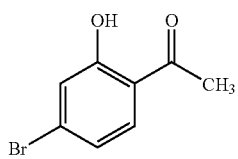

3-Bromophenyl acetate (intermediate 28) (30.6 g) was added portionwise to powdered aluminium chloride 15.5 g) with stirring. The resulting liquid was stirred at 170° under nitrogen for 1 h then at 70° for 2 h. 2N Hydrochloric acid (150 ml) was added and the mixture was allowed to cool to room temp. The mixture was extracted with ethyl acetate (×2) and the solvent was evaporated to leave a dark oil which was purified on silica (500 g) eluting with cyclohexane:ethyl acetate (4: 1) to give the title compound as a slightly coloured a semi-solid (26.8 g).

LCMS: Rt 3.2 min.

Intermediate 30

Ethyl 3-(4-bromo-2-hydroxyphenyl)-3-oxoproyanoate

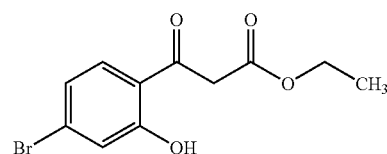

A solution of ethyl 3-(4-bromo-2-hydroxyphenyl)-3-oxopropanoate (Intermediate 29) (3.0 g) in dry toluene (10 ml) was added dropwise to a stirred suspension of sodium hydride (60% oil dispersion, 1.54 g) in dry toluene (15 ml) at reflux under nitrogen. After the addition stirring was continued for a further 10 min then diethylcarbonate (3.39 ml) was added over 30 min. The mixture was then stirred at reflux for 18 h. On cooling, ice-cold 2N hydrochloric (150 ml) added and the mixture was extracted with ethyl acetate (2×100 ml). The combined extracts were washed with water and brine, dried (MgSO$_4$) and concentrated under vacuum. The residue was purified by column chromatography on silica (100 g) eluting with cyclohexane:ethylacetate (10:1) to give the title compound as a cream solid (2.87 g).

LCMS: Rt 3.25 min.

Intermediate 31

7-Bromo-4-hydroxy-2H-chromen-2-one

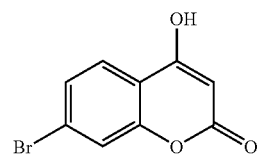

A solution of ethyl 3-(4-bromo-2-hydroxyphenyl)-3-oxopropanoate (Intermediate 30) (2.0 g) in dry toluene (20 ml) was stirred at reflux under nitrogen for 24 h. On cooling the resulting precipitate was collected by filtration, washed with ether and dried to give the title compound as a white solid (1.32 g).

LCMS: Rt 3.47 min.

Intermediate 32

(6-Bromo-1,2-benzisoxazol-3-yl)acetic acid

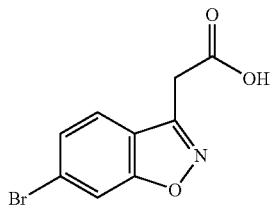

Sodium metal (0.36 g) was dissolved in dry ethanol (30 ml) then treated with hydroxylamine hydrochloride (1.12 g). A solution of 7-bromo-4-hydroxy-2H-chromen-2-one (Intermediate 31) (1.3 g) in dry ethanol (30 ml) was added and the mixture was stirred at reflux under nitrogen for 3.5 h. On cooling the mixture was added to 2M aqueous sodium bicarbonate (100 ml). Water (100 ml) and dichloromethane (100 ml) were added, the phases were separated and the aqueous layer was washed with more dichloromethane (75 ml). The aqueous layer was acidified by the cautious addition of 2N hydrochloric acid to yield a precipitate which was collected by filtration and dried to give the title compound as a white solid (1.06 g).

LCMS: Rt 2.99 min.

Intermediate 33

1,1-Dimethylethyl 4-[(6-bromo-1,2-benzisoxazol-3-yl)acetyl]-1-piperazinecarboxylate

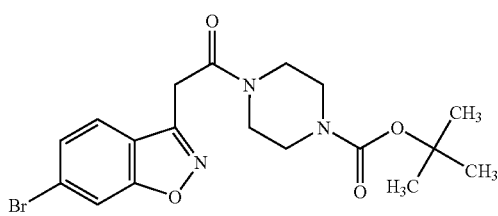

A suspension of (6-bromo-1,2-benzisoxazol-3-yl)acetic acid (Intermediate 32) (0.06 g) and HATU (0.09 g) in dry tetrahydrofuran (2 ml) was stirred at room temp. for 5 min. 1-Hydroxybenzotriazole (0.03 g) and 1,1-dimethylethyl 1-piperazinecarboxylate (0.04 g) were added and the reaction mixture was stirred for a further 18 h. The solvent was removed under vacuum and the residue was partitioned between dichloromethane and 2N aqueous sodium carbonate. The layers were separated and the organic layer was applied to a Varian Bond-Elut SPE cartridge (silica, 5 g ) eluting sequentially with dichloromethane, chloroform, ether and ethyl acetate to give the title compound as a white solid (0.09 g).

LCMS: Rt 3.21 min.

Intermediate 34

1,1-Dimethylethyl 4-[(6-{5-[(cyclopropylamino)carbonyl]-2-methylphenyl}-1,2-benzisoxazol-3-yl)acetyl]-1-piperazinecarboxylate

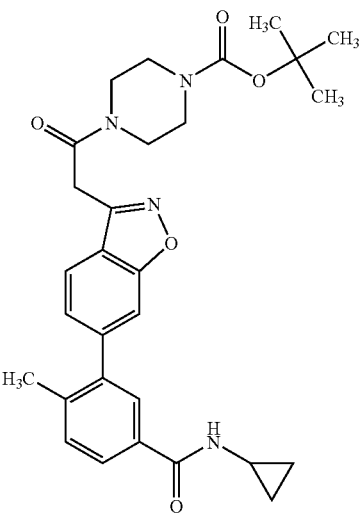

A mixture of 1,1-dimethylethyl 4-[(6-bromo-1,2-benzisoxazol-3-yl)acetyl]-1-piperazinecarboxylate (Intermediate 33) (0.045 g) N-cyclopropyl-4-methyl-3-(4,4,5,5-tetramethyl-1,3,2-dioxaborolan-2-yl)benzamide (Intermediate 5) (0.03 g) and 2M aqueous sodium carbonate (0.65 ml) in isopropanol (2.5 ml) under nitrogen was treated with tetrakis(triphenylphosphine)palladium(0) (1 mg) then stirred at reflux for 18 h. On cooling the mixture was absorbed onto silica (Merck 7734) and applied to a Varian Bond-Elut SPE cartridge (silica, 5 g). Sequential elution with dichloromethane, chloroform, ether, ethyl acetate, acetonitrile and acetone yielded the title compound as a white solid (0.03 g).

LCMS: Rt 3.16 min.

Intermediate 35

2-(6-Bromo-1,2-benzisoxazol-3-yl)-N-(2-hydroxyethyl)acetamide

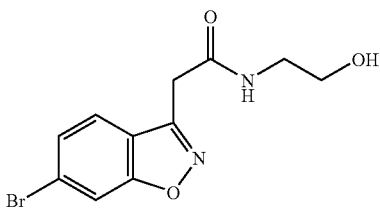

A suspension of (6-bromo-1,2-benzisoxazol-3-yl)acetic acid (Intermediate 32) (0.10 g) and HATU (0.18 g) in tetrahydrofuran (5 ml) was stirred at room temp. for 10 min then treated with 1-hydroxybenzotriazole (0.05 g) 2-aminoethanol (0.03 ml) and diisopropylethylamine (0.2 ml). The mixture was stirred for a further 18 h then concentrated under vacuum. The residue was partitioned between dichloromethane (5 ml) and 2M aqueous sodium carbonate (5 ml). The organic layer was dried using a hydrophobic filter tube then applied to a Varian Bond-Elut SPE cartridge. Sequential elution with dichloromethane, ether, ethyl acetate, acetonitrile and acetone yieldded the title compound as a white solid (0.08 g).
LCMS: Rt 2.42 min.

Intermediate 36

6-Bromo-3-[2-oxo-2-(1-piperidinyl)ethyl]-1,2-benzisoxazole

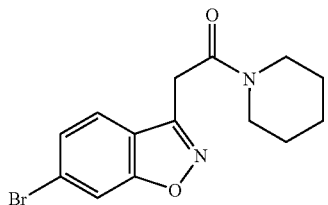

The procedure for Intermediate 35 was followed using piperidine (0.05 ml) in place of 2-aminoethanol to give the title compound as a white solid (0.10 g).
LCMS: Rt 3.09 min.

Intermediate 37

2-(6-Bromo-1,2-benzisoxazol-3-yl)-N-methylacetamide

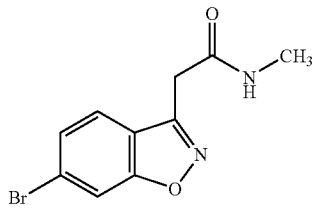

The procedure for Intermediate 35 was followed using a solution of methylamine in tetrahydrofuran (2M, 0.235 ml) in place of 2-aminoethanol to give the title compound as a white solid (0.10 g).
LCMS: Rt 2.59 min.

Intermediate 38

2-(6-Bromo-1,2-benzisoxazol-3-yl)-N-(3-hydroxypropyl)acetamide

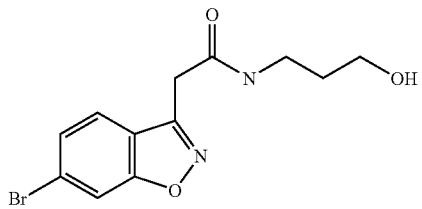

The procedure for Intermediate 35 was followed using 3-aminopropanol (0.04 ml) in place of 2-aminoethanol to give the title compound as a white solid (0.09 g).
LCMS: Rt 2.48 min.

Intermediate 39

2-(6-Bromo-1,2-benzisoxazol-3-yl)-N-(cyclopropylmethyl)acetamide

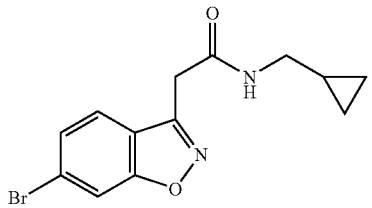

The procedure for Intermediate 35 was followed using cyclopropylmethylamine (0.04 ml) in place of 2-aminoethanol to give the title compound as a white solid (0.11 g).
LCMS: Rt 2.99 min.

Intermediate 40

6-Bromo-3-[2-oxo-2-(1-pyrrolidinyl)ethyl]-1,2-benzisoxazole

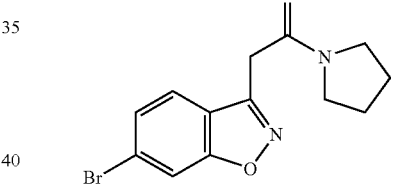

The procedure for Intermediate 35 was followed using pyrrolidine (0.04 ml) in place of 2-aminoethanol to give the title compound as a white solid (0.10 g).
LCMS: Rt 2.87 min.

Intermediate 41

2-(6-Bromo-1,2-benzisoxazol-3-yl)-N-ethylacetamide

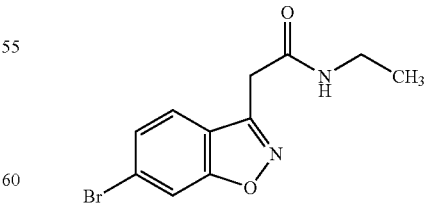

The procedure for Intermediate 35 was followed using a solution of ethylamine in tetrahydrofuran (0.235 ml) in place of 2-aminoethanol to give the title compound as a white solid (0.09 g).
LCMS: Rt 2.74 min.

Intermediate 42

2-(6-Bromo-1,2-benzisoxazol-3-yl)-N-cyclopropylacetamide

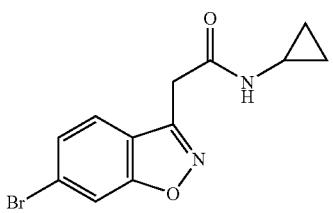

The procedure for Intermediate 35 was followed cyclopropylamine (0.03 ml) in place of 2-aminoethanol to give the title compound as a white solid (0.08 g).

LCMS: Rt 2.78 min.

Intermediate 43

6-Bromo-3-[2-(4-morpholinyl)-2-oxoethyl]-1,2-benzisoxazole

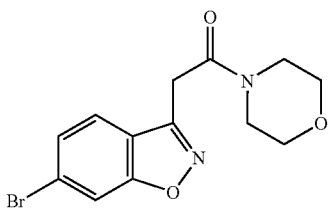

The procedure for Intermediate 35 was followed morpholine (0.04 ml) in place of 2-aminoethanol to give the title compound as a white solid (0.10 g).

LCMS: Rt 2.69 min.

Intermediate 44

2-(6-Bromo-1,2-benzisoxazol-3-yl)-N-{[3-(methyloxy)phenyl]methyl}acetamide

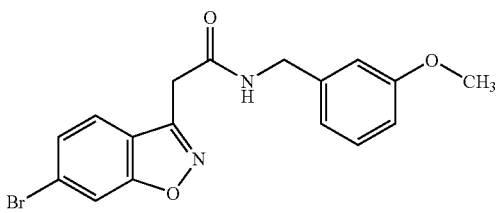

The procedure for Intermediate 35 was followed 3-methoxybenzylamine (0.06 ml) in place of 2-aminoethanol to give the title compound as a white solid (0.10 g).

LCMS: Rt 3.20 min.

Intermediate 45

2-(6-Bromo-1,2-benzisoxazol-3-yl)-N-1,3-thiazol-2-ylacetamide

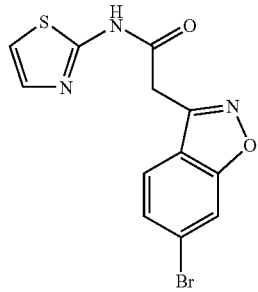

The procedure for Intermediate 35 was followed 2-amino-1,3-thiazole (0.05 ml) in place of 2-aminoethanol to give the title compound as a white solid (0.06 g).

LCMS: Rt 3.11 min.

Intermediate 46

6-Bromo-3-[(4-methyl-1-piperazinyl)methyl]-1,2-benzisoxazole

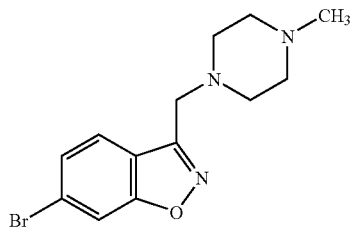

A solution of Intermediate 1 (0.06 g), 1-methylpiperazine (0.05 ml) and diisopropylethylamine (0.1 ml) in DMF (0.5 ml) was stirred at 65° for 4 h. The reaction mixture was partitioned between ethyl acetate and saturated aqueous sodium hydrogen carbonate, the phases were separated and the aqueous layer was re-extracted with ethyl acetate. The organic extracts were washed with water (×2) and brine, dried using a hydrophobic filter tube and concentrated under a stream of nitrogen. The residue was purified on a Varian Bond-Elut SPE cartridge (silica, 2 g) eluting with dichloromethane:methanol:ethylamine (100:0:1 to 95:5:1) to give the title compound as a pale yellow solid (0.04 g).

LCMS: Rt 2.07 min.

Intermediate 47

6-Bromo-3-(1-piperidinylmethyl)-1,2-benzisoxazole

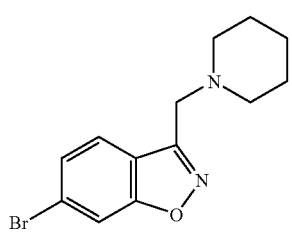

The procedure for Intermediate 46 was followed using piperidine (0.05 ml) in place of 1-methylpiperazine. Elution of the SPE cartridge with cyclohexane:ethyl acetate:triethylamine (100:0:1 to 80:20:1) gave the title compound as a pale yellow solid (0.03 g).

LCMS: Rt 2.00 min.

Intermediate 48

6-Bromo-3-(4-morpholinylmethyl)-1,2-benzisoxazole

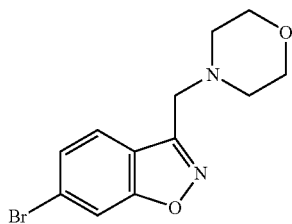

The procedure for Intermediate 46 was followed using morpholine (0.05 ml) in place of 1-methylpiperazine. Elution of the SPE cartridge with cyclohexane:ethyl acetate:triethylamine (100:0:1 to 66:33:1) gave the title compound as a pale yellow solid (0.04 g).

LCMS: Rt 2.46 min.

Intermediate 49

6-Bromo-3-(1-pyrrolidinylmethyl)-1,2-benzisoxazole

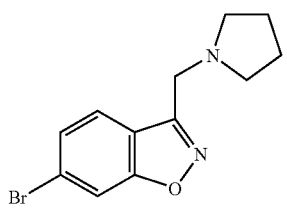

The procedure for Intermediate 46 was followed using pyrrolidine (0.05 ml) in place of 1-methylpiperazine. Elution of the SPE cartridge with cyclohexane:ethyl acetate:triethylamine (100:0:1 to 80:20:1) gave the title compound as a pale yellow solid (0.03 g).

LCMS: Rt 1.88 min.

Intermediate 50

4-Bromo-2-fluorobenzaldehyde oxime

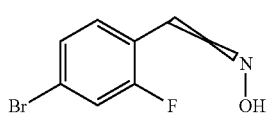

A solution of hydroxylamine in water (50%, 5 ml) was added to a solution of 4-bromo-2-fluorobenzaldehyde (1.0 g) in ethanol (5 ml) and the mixture was stirred at room temp. for 66 h. The ethanol was removed under vacuum and the aqueous residue as extracted with ethyl acetate (×2). The organic extracts were washed with water and brine, dried (MgSO$_4$) and concentrated under vacuum. The residue was purified on a Varian Bond-Elut SPE cartridge (silica, 20 g) eluting with cyclohexane:ethyl acetate (100:0 to 50:50) to give the title compound as a white solid (0.94 g).

LCMS: Rt 3.15 min.

Intermediate 51

4-Bromo-2-fluoro-N-hydroxybenzenecarboximidoyl chloride

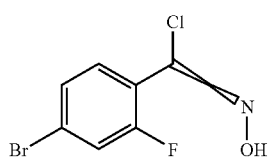

N-Chlorosuccinimide (0.075 g) was added to a solution of 4-bromo-2-fluorobenzaldehyde oxime (Intermediate 50) (0.44 g) in DMF (1 ml) then heated for several minutes at 55°. The mixture was allowed to cool to <50° then more N-chlorosuccinimide (0.22 g) was added. After a few minutes the mixture was allowed to cool to room temp. then partitioned between water and ether. The layers were separated, the aqueous layer was re-extracted with ether (×2) and the combined organic extracts were washed with water and brine, dried (MgSO$_4$) and concentrated under vacuum to give a white solid (0.46 g).

LCMS: Rt 3.11.

Intermediate 52

4-Bromo-N-cyclopropyl-2-fluoro-N'-hydroxybenzenecarboximidamide

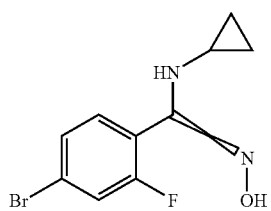

Cyclopropylamine (1.6 ml) was added dropwise to an ice-old solution of 4-bromo-2-fluoro-N-hydroxybenzenecarboximidoyl chloride (Intermediate 51) (0.59 g) in dry ether (25 ml) under nitrogen. After the addition the mixture was allowed to warm to room temp. then stirred for 18 h. The resulting precipitate was collected by filtration then purified by column chromatography on silica eluting with cyclohexane:ethyl acetate (3:2) to give the title compound as a white solid (0.435 g).

LCMS: Rt 2.69 min.

Intermediate 53

6-Bromo-N-cyclopropyl-1,2-benzisoxazol-3-amine

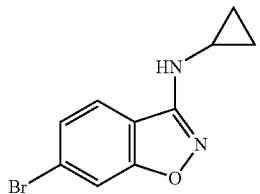

1,8-Diazabicyclo[5.4.0]undec-7-ene (0.12 ml) was added to 4-bromo-N-cyclopropyl-2-fluoro-N'-hydroxybenzenecarboximidamide (Intermediate 52) (0.2 g) in tetrahydrofuran (2 ml) then heated at 150° in a microwave for 70 min. The mixture was applied to a Varian Bond-Elut SPE cartridge (silica, 20 g) then eluted with cyclohexane:ethyl acetate (100:0 to 80:20) to give the title compound as a white solid (0.13 g).
LCMS: Rt 3.16 min.

Intermediate 54

Methyl (4-bromo-2-nitrophenyl)acetate

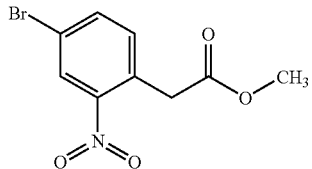

Conc. hydrochloric acid (1 ml) was added to a solution of (4-bromo-2-nitrophenyl)acetic acid (7.07 g) and the solution was stirred under reflux for 5 h. The solvent was evaporated to leave the title compound as a crystalline brown solid (7.39 g).
LCMS: Rt 3.13 min.

Intermediate 55

Ethyl 6-bromo-1,2-benzisoxazole-3-carboxylate

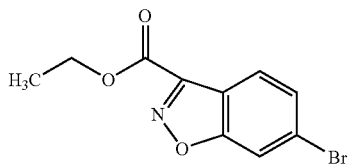

Sodium metal (0.09 g) was dissolved in absolute ethanol (2 ml) under nitrogen. A solution of methyl (4-bromo-2-nitrophenyl)acetate (Intermediate 54) (1.0 g) in ethanol (8 ml) was treated with isoamyl nitrite (0.6 ml) followed by the solution of sodium ethoxide, yielding a black mixture. The mixture was stirred at 60° for 90 min then left at room temp. for 18 h. 2N Hydrochloric acid (20 ml) was added and the mixture was extracted with ethyl acetate (2×20 ml). The combined organic extracts were washed with water (×2) and brine, dried using a hydrophobic filter tube and concentrated under vacuum. The residue was purified on a Varian Bond-Elut SPE cartridge eluting with cyclohexane:ethyl acetate (100:0 to 97:3) to give the title compound as a cream coloured solid (577 mg).
LCMS: Rt 3.40 min.

Intermediate 56

6-Bromo-N-(cyclopropylmethyl)-1,2-benzisoxazole-3-carboxamide

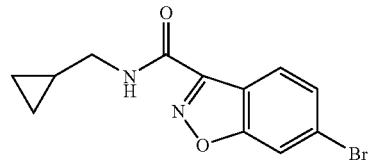

A solution of ethyl 6-bromo-1,2-benzisoxazole-3-carboxylate (Intermediate 55) (0.05 g) and cyclopropylamine (0.03 ml) in methanol (1 ml) was stirred at reflux for 6 h. The solvent was evaporated and the residue was triturated with ether to give the title compound as a white solid (0.04 g).

Intermediate 57

6-Bromo-N-propyl-1,2-benzisoxazole-3-carboxamide

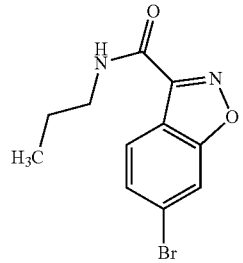

The procedure for Intermediate 56 was followed using propylamine (0.025 ml) in place of cyclopropylmethylamine to give the title compound as a white solid (0.04 g).
LCMS: Rt 3.30 min.

Intermediate 58

6-Bromo-N-methyl-1,2-benzisoxazole-3-carboxamide

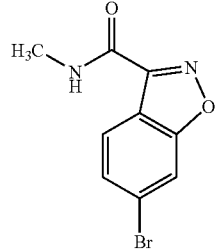

The procedure for Intermediate 56 was followed using a solution of methylamine in methanol (2M, 0.45 ml)) in place of cyclopropylmethylamine to give the title compound as a white solid (0.03 g).
LCMS: Rt 2.92 min.

Intermediate 59

6-Bromo-N,N-dimethyl-1,2-benzisoxazole-3-carboxamide

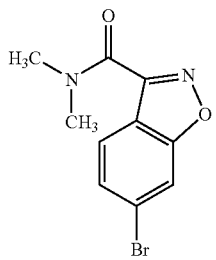

The procedure for Intermediate 56 was followed using a solution of dimethylamine in methanol (2M, 0.13 ml)) in place of cyclopropylmethylamine to give the title compound as a white solid (0.02 g).
LCMS: Rt 2.88 min.

Intermediate 60

6-Bromo-N-cyclopropyl-1,2-benzisoxazole-3-carboxamide

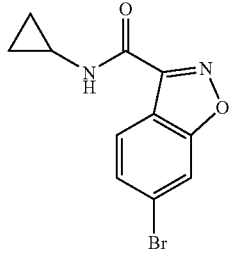

The procedure for Intermediate 56 was followed using cyclopropylamine (0.025 ml) in place of cyclopropylmethylamine to give the title compound as a white solid (0.05 g).
LCMS: Rt 3.30 min.

Intermediate 61

3-Bromo-N-cyclopropyl-5-fluoro-4-methylbenzamide

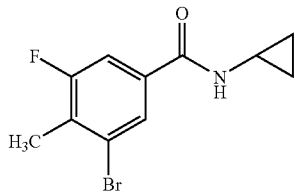

3-Fluoro-4-methylbenzoic acid (0.46 g) was added to a stirred mixture of bromine (2.31 ml) and iron powder (0.25 g) under nitrogen. The reaction was stirred at 20° C. for 4 h and then left to stand for 16 h. Sodium thiosulphate solution (200 ml) was added and the product was extracted into ethyl acetate (3×150 ml). Ethyl acetate extracts were combined and concentrated under vacuum. The crude product was dissolved in DMF (7 ml) and cyclopropylamine (0.28 ml) 1-hydroxybenzotriazole (0.405 g) 1-(3-dimethylaminopropyl)-3-ethylcarbodiimide hydrochloride (0.575 g) and diisopropylethylamine (0.52 ml) were added. The mixture was stirred for 5 h at 20° C. The solvent was removed under vacuum and the residue was partitioned between ethyl acetate and water. The combined organic extracts were washed with aqueous sodium hydrogen carbonate and hydrochloric acid (0.5M) dried (MgSO$_4$) and concentrated under vacuum. The residue was purified by column chromatography on silica eluting with cyclohexane:ethyl acetate (6:1) to give the title compound (359 mg).
LCMS: MH$^+$ 272.

Intermediate 62

N-Cyclopropyl-3-fluoro-4-methyl-5-(4,4,5,5-tetramethyl-1,3,2-dioxaborolan-2-yl)benzamide

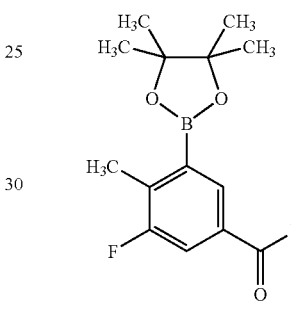

3-Bromo-N-cyclopropyl-5-fluoromethylbenzamide (Intermediate 61) (900 mg), bispinnacolatodiboron (4.5 g), potassium acetate (2.1 g) and PdCl$_2$dppf (75 mg) were mixed in DMF (40 ml) and heated at 100° C. for 18 h. The cooled reaction was absorbed onto silica and applied to a Varian Bond Elut SPE cartridge (silica, 2×10 g) and eluted with an cyclohexane:ethyl acetate (100:0 to 94:6). The solvent was under vacuum and the residue was recrystallised from cyclohexane to give the title compound (260 mg).
LCMS: Rt 3.39 mins.

Intermediate 63

N-Cyclopropyl-3-fluoro-5-iodo-4-methylbenzamide

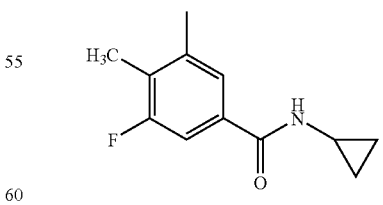

N-Iodosuccinimide (22.5 g) was added in portions to a solution of 3-fluoro-4-methylbenzoic acid (15.4 g) in trifluoromethanesulphonic acid (100 ml) at 0° C. over 3 h and the mixture was allowed to warm to room temp overnight. The reaction mixture was poured into ice/water (400 ml) and the precipitate was collected by filtration and washed with water.

The solid was dissolved in ethyl acetate, washed with aqueous sodium thiosulphate (×2) and brine, dried (MgSO$_4$) and the solvent was removed under vacuum. The residue was treated with thionyl chloride (30 ml) and heated at 100° C. for 2.5 h. Excess thionyl chloride was removed under vacuum and the residue was dissolved in dichloromethane (100 ml). Sodium carbonate (25 g ) and cyclopropylamine (13 ml) were added to the solution and the mixture was stirred at room temp. for 72 h. The mixture was filtered and the residue was washed with dichloromethane and ethyl acetate. The combined filtrate and washings were concentrated under vacuum. The residue was purified by column chromatography on silica eluting with cyclohexane:ethyl acetate (78:22 to 72:28) to give the title compound.

LCMS: Rt 3.16 min.

Intermediate 64

{5-[(Cyclopropylamino)carbonyl]-3-fluoro-2-methylphenyl}boronic acid

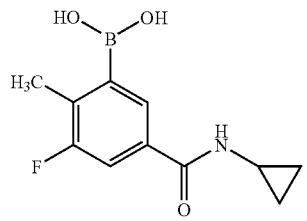

N-Cyclopropyl-5-fluoro-3-iodo-4-methylbenzamide (Intermediate 63) (5 g) in tetrahydrofuran (75 ml) was cooled to 0° C. then treated with sodium hydride (60% oil dispersion, 1.23 g) portionwise over 10 minutes. Once effervescence had ceased the reaction was cooled to –75° C. and n-butyl lithium (1.6M in hexanes, 20 ml) was added over 25 min maintaining a temperature of <–70° C. Triisopropyl borate (8 ml) was added over 10 min and the mixture was stirred at –70° C. for 4 h. Water (20 ml) was added and the mixture was allowed to warm to 5° C. The solvent was removed under vacuum and the residue was partitioned between saturated aqueous ammonium chloride and ethyl acetate. The organic phase was washed with saturated aqueous ammonium chloride and brine, dried (Na$_2$SO$_4$) and concentrated under vacuum. The residue was dissolved in dichloromethane/ethyl acetate and purified by column chromatography on silica eluting with dichloromethane:ethyl acetate (95:5 to 0:100) then methanol to give the title compound.

LCMS: Rt 2.19 min.

Intermediate 65

1-Acetyl-6-bromo-1H-indazole

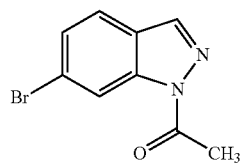

A solution of 4-bromo-2-methylaniline (10.0 g) in chloroform (100 ml) was treated with acetic anhydride (11.5 g) and potassium acetate (5.8 g) then stirred at 55° for 5 h to give a thick suspension. t-Butyl nitrite (19.2 ml) and 18-crown-6 (28.4 g) were added to give a solution which was stirred at 55° for a further 21 h. The solvent was evaporated and the oily residue which was eluted through a pad of silica (150 g) using cyclohexane-ethyl acetate (4:1). The solvent was evaporated and the residue was purified by column chromatography on silica eluting with cyclohexane:ethyl acetate (20:1 to 8:1) to give the title compound (5.08 g).

LCMS: Rt 3.20 min.

Intermediate 66

(4-Bromo-2-nitrophenyl)methyl 4-fluorophenyl sulfide

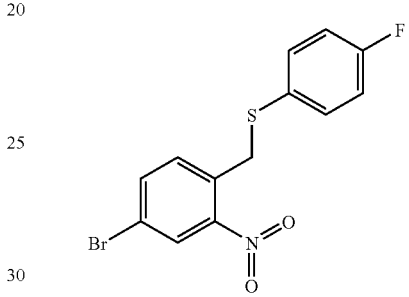

To a solution of 4-bromo-1-(bromomethyl)-2-nitrobenzene (0.60 g) in tetrahydrofuran (10 ml) was added 4-fluorothiophenol (1.2 ml) and diisopropylethylamine (0.45 ml). After stirring for 2 h the mixture was concentrated under vacuum and purified by column chromatography on silica, eluting with petroleum ether (40-60°):dichloromethane (9:1 to 8:1) to give the title compound (0.52 g).

LCMS: Rt 3.73 min.

Intermediate 67

(4-Bromo-2-nitrophenyl)methyl 4-fluorophenyl sulfone

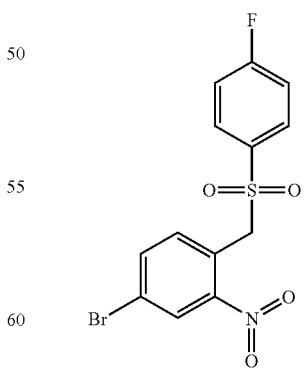

A suspension of oxone (3.55 g) in water (8 ml) was added to a solution of (4-bromo-2-nitrophenyl)methyl 4-fluorophenyl sulfide (Intermediate 66) (0.52 g) in acetonitrile (10 ml). The mixture was stirred for 5 h filtered and the residue was washed with ethyl acetate. The biphasic filtrate was separated, the aqueous layer was re-extracted with ethyl acetate (2×50 ml) and the combined organic extracts were washed with aqueous sodium metabisulphite (5%, 100 ml) and brine. The dried (MgSO₄) extracts were concentrated under vacuum to give the title compound (0.56 g).
LCMS: Rt 3.33 min.

Intermediate 68

(5-Bromo-2-{[(4-fluorophenyl)sulfonyl]methyl}phenyl)amine

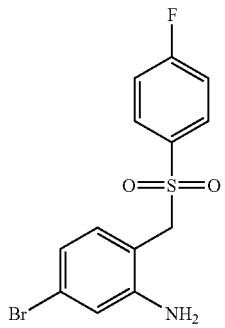

Saturated ammonium chloride (2.2 ml) and iron powder (0.25 g) was added to a suspension of (5-bromo-2-{[(4-fluorophenyl)sulfonyl]methyl}phenyl)amine (Intermediate 67) (0.56 g) in toluene (10 ml) then stirred for 18 h at reflux. The mixture was cooled and evaporated to give a white solid which was partitioned between ethyl acetate (3×20 ml) and saturated aqueous sodium bicarbonate (15 ml). The dried (MgSO₄) organic extracts were concentrated under vacuum to give the title compound (0.42 g).
LCMS: Rt 3.16 min.

Intermediate 69

6-Bromo-3-[(4-fluorophenyl)sulfonyl]-1H-indazole

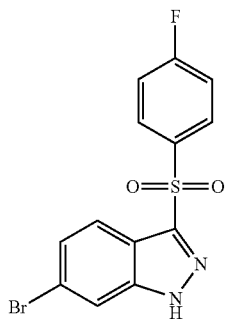

To a suspension of (5-bromo-2-{[(4-fluorophenyl)sulfonyl]methyl}phenyl)amine (Intermediate 68) (0.42 g) in chloroform (10 ml) was added potassium acetate (0.135 g) and acetic anhydride (0.24 ml). The mixture was heated under nitrogen at reflux for 18 h. 18-Crown-6 (0.64 g) and tert-butylnitrite (0.435 ml) were added and the mixture was stirred at reflux for a further 42 h. The mixture was concentrated under vacuum and the residue was purified by column chromatography on silica eluting with cyclohexane:ethylacetate (4:1) to give the title compound (0.16 g).
LCMS: Rt 3.43 min.

Intermediate 70

6-Bromo-3-[(4-fluorophenyl)sulfonyl]-1-({[2-(trimethylsilyl)ethyl]oxy}methyl)-1H-indazole

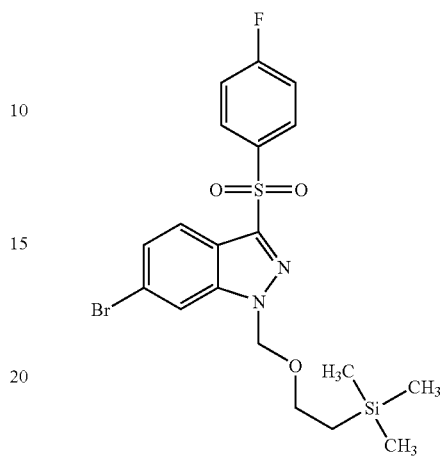

Sodium tert-butoxide (0.035 g) was added to an ice-cold solution of 6-bromo-3-[(4-fluorophenyl)sulfonyl]-1H-indazole (Intermediate 69) (0.11 g) in tetrahydrofuran (1.5 ml). 2-(Trimethylsilyl)ethoxymethyl chloride (0.06 ml) was then added and the mixture was warmed to room temp. over 1 h. The reaction was quenched using 2M aqueous ammonia (1 ml) and methanol (1 ml) the solvent was evaporated and the residue was purified on a Varian Bond-Elut SPE cartridge, eluting with cyclohexane:dichloromethane (100:0 to 0: 100) to give the title compound (0.67 g).
LCMS: Rt 4.09 min.

Intermediate 71

N-Cyclopropyl-3-[3-[(4-fluorophenyl)sulfonyl]-1-({[2-(trimethylsilyl)ethyl]oxy}methyl)-1H-indazol-6-yl]-4-methylbenzamide

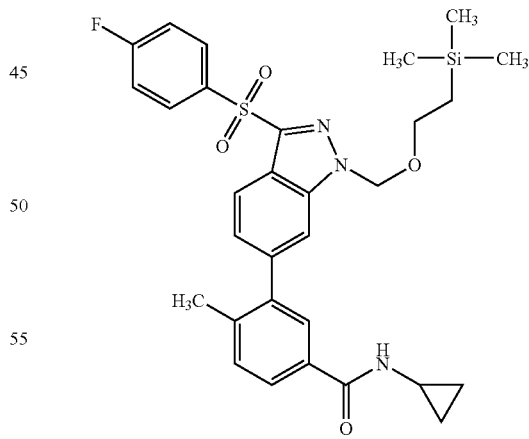

A mixture of 6-bromo-3-[(4-fluorophenyl)sulfonyl]-1-({[2-(trimethylsilyl)ethyl]oxy}methyl)-1H-indazole (Intermediate 70) (0.06 g) N-cyclopropyl-4-methyl-3-(4,4,5,5-tetramethyl-1,3,2-dioxaborolan-2-yl)benzamide (Intermediate 5) (0.04 g) aqueous sodium carbonate (1M, 0.66 ml) and tetrakis(triphenylphosphine)palladium(0) (0.015 g) in 1,2-dimethoxyethane (4 ml) was stirred at reflux under nitrogen for 18 h. The mixture was concentrated under vacuum and the residue was purified on a Varian Bond-Elut SPE cartridge, eluting with cyclohexane:ethyl acetate (100:0 to 50:50) to give the title compound (0.05 g).

LCMS: Rt 3.91 min.

Intermediate 72

(4-Bromo-2-nitrophenyl)methyl sulfide

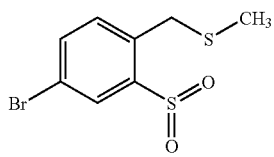

A suspension of 4-bromo-1-(bromomethyl)-2-nitrobenzene (1.0 g) and sodium methanethiolate (0.285 g) in tetrahydrofuran (20 ml) was stirred under nitrogen for 60 h. The solvent was evaporated, chloroform (50 ml) was added and the rsidual solid was removed by filtration. The filtrate was comncentrated under vacuum to give the title compound (0.89 g).

LCMS: Rt 3.35 min.

Intermediate 73: (4-Bromo-2-nitrophenyl)methyl sulfone

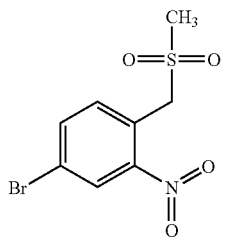

A suspension of oxone (7.94 g) in water (16 ml) was added to a solution of (4-bromo-2-nitrophenyl)methyl methyl sulfide (Intermediate 72) (0.52 g) in acetonitrile (20 ml). The mixture was stirred for 5 h filtered and the residue was washed with ethyl acetate. The biphasic filtrate was separated, the aqueous layer was re-extracted with ethyl acetate (2×50 ml) and the combined organic extracts were washed with aqueous sodium metabisulphite (5%, 100 ml) water and brine. The solution was dried using a hydrophobic filter tube then concentrated under vacuum to give the title compound (0.35 g).

LCMS: Rt 2.72 min.

Intermediate 74

{5-Bromo-2-[(methylsulfonyl)methyl]phenyl}amine

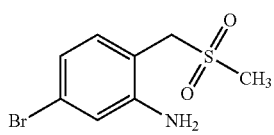

Tin(II) chloride dihydrate (1.34 g) was added to a stirred suspension of (4-bromo-2-nitrophenyl)methyl sulfone (Intermediate 73) in dry ethanol (10 ml) and the mixture was stirred at 50° under nitrogen for 2.5 h. The solvent was evaporated and the residue was partitioned between aqueous sodium hydroxide (2M, 30 ml) and dicloromethane (200 ml). The organic phase was dried using a hydrophobic filter tube and concentrated under vacuum to give the title compound (0.26 g).

LCMS: Rt 2.42 min.

Intermediate 75

6-Bromo-3-(methylsulfonyl)-1H-indazole

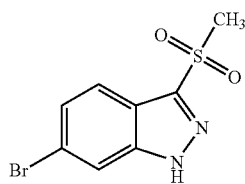

To a suspension of {5-bromo-2-[(methylsulfonyl)methyl]phenyl}amine (Intermediate 74) (0.26 g) in chloroform (8 ml) was added potassium acetate (0.11 g) and acetic anhydride (0.195 ml). The mixture was heated under nitrogen at reflux for 18 h. 18-Crown-6 (0.26 g) and tert-butylnitrite (0.35 ml) were added and the mixture was stirred at reflux for a further 88 h. The mixture was concentrated under vacuum and the residue was purified by column chromatography on silica eluting with cyclohexane:ethylacetate (4:1 to 1:1) to give the title compound (0.14 g).

LCMS: Rt 2.85 min.

Intermediate 76

6-Bromo-3-(methylsulfonyl)-1-({[2-(trimethylsilyl)ethyl]oxy}methyl)-1H-indazole

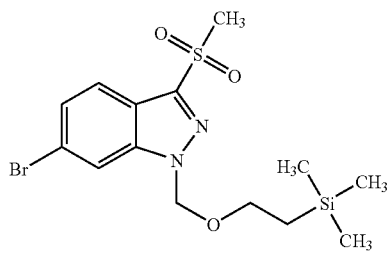

Sodium tert-butoxide (0.057 g) was added to an ice-cold solution of 6-bromo-3-(methylsulfonyl)-1H-indazole (Intermediate 75) (0.14 g) in tetrahydrofuran (1.5 ml). 2-(Trimethylsilyl)ethoxymethyl chloride (0.11 ml) was then added and the mixture was warmed to room temp. over 1 h. The reaction was quenched using 2M aqueous ammonia (1 ml) and methanol (1 ml) the solvent was evaporated and the aqueous residue was extracted with ethyl acetate. The organic extracts were dried using a hydrophobic filter tube and concentrated under vacuum to give the title compound (0.67 g).

LCMS: Rt 3.81 min.

Intermediate 77

N-Cyclopropyl-3-fluoro-4-methyl-5-[3-(methylsulfonyl)-1-({[2-(trimethylsilyl)ethyl]oxy}methyl)-1H-indazol-6-yl]benzamide

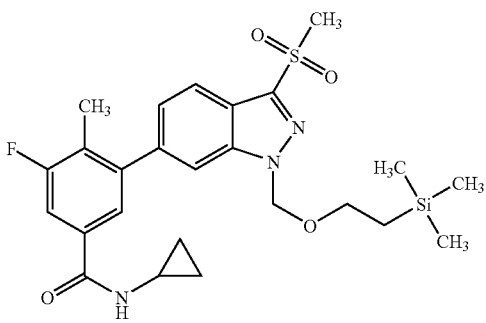

A mixture of 6-bromo-3-(methylsulfonyl)-1-({[2-(trimethylsilyl)ethyl]oxy}methyl)-1H-indazole (Intermediate 76) (0.18 g) N-cyclopropyl-3-fluoro-4-methyl-5-(4,4,5,5-tetramethyl-1,3,2-dioxaborolan-2-yl)benzamide (Intermediate 62) (0.14 g) aqueous sodium carbonate (1M, 1.32 ml) and tetrakis(triphenylphosphine)palladium(0) (0.01 g) in isopropanol (2 ml) was stirred at reflux under nitrogen for 18 h. The mixture was concentrated under vacuum and the residue was purified by column chromatography on silica eluting with cyclohexane:ethyl acetate (2:1) to give the title compound (0.15 g).

LCMS: Rt 3.82 min.

Intermediate 78

1-Acetyl-5-bromo-3-methyl-1H-indazole

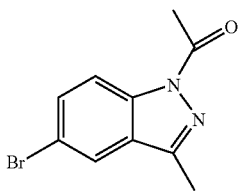

A solution of 4-bromo-2-ethylaniline (1.09 g) in chloroform (20 ml) was stirred at room temp. then treated with potassium acetate (0.49 g) followed by acetic anhydride (0.95 ml). 18-Crown-6 (0.26 g) and t-butylnitrite (1.32 ml) were added after 30 min and the mixture was stirred at reflux for 18 h. The reaction mixture was diluted with chloroform and washed with saturated aqueous sodium hydrogen carbonate. The organic phase was separated using a hydrophobic frit and the solvent was evaporated to give the title compound as a brown solid (1.0 g).

NMR: δH[CDCl3] 8.30 (1H, d), 7.79 (1H, s), 7.63 (1H, d), 2.74 (3H, s), (2.55 (3H, s).

General Method A

The halide (30 μmoles) was dissolved in DME or DMF (0.4-0.5 ml). The boronate ester (30 μmoles in 0.2 ml DME or DMF), sodium carbonate (10% aqueous solution, 0.25 ml) and
(A) tetrakis (triphenylphosphine) palladium (3.5 μmoles in 0.1 ml DME) or
(B) FibreCat™ 1001 (12 mg) were added and the mixture was heated under nitrogen at 80° for 18 h. The reaction mixture was
(A) filtered through silica (100 mg) and washed with methanol
(B) filtered through Celite and washed with DME or DMF.

The solvent was evaporated and the residue was dissolved in DMSO (0.25 ml) and purified by preparative mass-directed LC-MS.

General Method B

A solution of N-cyclopropyl-3-(1H-indazol-5-yl)-4-methylbenzamide Example 17, 30 mg) in dichloromethane (2 ml) was added to the sulfonyl chloride (0.11 mmol).

Pyridine (50 μmol) was added and the solution was stirred at 20° for 18 h (if a solution is not generated a substantial quantity of the 2-substituted product is formed). The solvent was evaporated and the residue was purified by column chromatography on silica eluting with cyclohexane:ethyl acetate (4:1 to 1:1).

General Method C

A solution of N-cyclopropyl-3-(1H-indazol-5-yl)-4-methylbenzamide (Example 17, or N-cyclopropyl-3-fluoro-5-(1H-indazol-5-yl)-4-methylbenzamide (Example 60) (100 mg) in DMF (3 ml) was treated with sodium hydride (60% dispersion in oil, 16.5 mg) under nitrogen. After 10 min the sulphonyl chloride (1.2 equiv) was added and the suspension was stirred at room temp. for 16 h. Methanol (5 ml) was added, the solvent was evaporated and the crude product was purified by column chromatography on silica eluting with a cyclohexane:ethyl acetate gradient or by reverse phase preparative Hplc.

General Method D

The solution of the ester methyl (5-{5-[(cyclopropylamino)carbonyl]-2-methylphenyl}-1H-indazol-1-yl)acetate (Example 117) or methyl (5-{5-[(cyclopropylamino)carbonyl]-3-fluoro-2-methylphenyl}-1H-indazol-1-yl)acetate (Example 123) (0.015 g) in methanol (0.2 ml) was treated with an amine (3 equiv) then stirred at 65° under nitrogen for 18 h. The methanol was evaporated and the residue, in chloroform, was applied to a Varian SCX-2 ion exchange column and eluted with chloroform:methanol (9:1). If required the product was further purified by reverse phase preparative Hplc.

Example 1

N-Cyclopropyl-4-methyl-3-(3-piperidin-4-yl-1,2-benzisoxazol-6-yl)benzamide

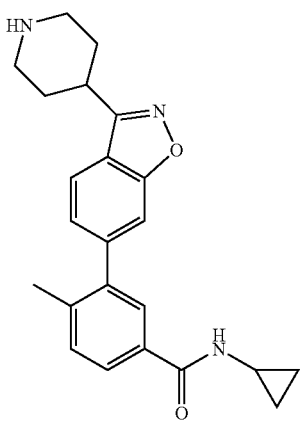

Example 1 was prepared by General Method A using 6-bromo-3-piperidin-4-yl-1,2-benzisoxazole and Intermediate 5.

NMR: δH [d6-DMSO] 8.43 (1H, s), 8.08 (1H, d), 7.75 (3H, m), 7.43 (2H, t), 3.6 (1H, m), 3.4 (2H, m) 3.12 (2H, m), 2.85 (2H, m), 2.3 (3H, s), 2.2 (2H, m), 2.1 (2H, m), 0.67 (2H, m), 0.56 (2H, m).

LCMS: Rt 2.31 min, MH+376.

Example 2

4-Methyl-N-(3-morpholin-4-ylphenyl)-3-(3-piperidin-4-yl-1,2-benzisoxazol-6-yl)benzamide

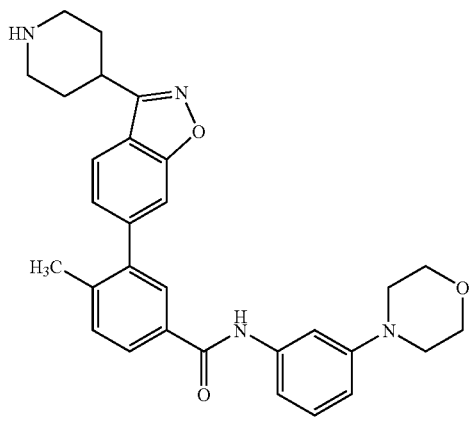

Example 2 was prepared by General Method A using 6-bromo-3-piperidin-4-yl-1,2-benzisoxazole and Intermediate 10.

NMR: δH [d6-DMSO] 10.09 (1H, s), 8.09 (1H, d), 7.94 (1H, dd), 7.91 (1H, brs), 7.82 (1H, brs), 7.51 (1H, d), 7.47 (1H, d), 7.39 (1h, brs), 7.29 (1H, brd), 7.19 (1H, t), 6.70 (1H, dd), 3.74 (4H, apparent t), 3.48 (1H, brm), 3.29 (2H, brd), 3.09 (4H, apparent t), 2.95 (2H, brt), 2.34 (3H, s), 2.15 (2H, brd), 2.01 (2H, brt).

LCMS: Rt 2.56 min, MH+497.

Example 3

N-[4-Methyl-3-(3-piperidin-4-yl-1,2-benzisoxazol-6-yl)phenyl]-2-pyrrolidin-1-ylisonicotinamide

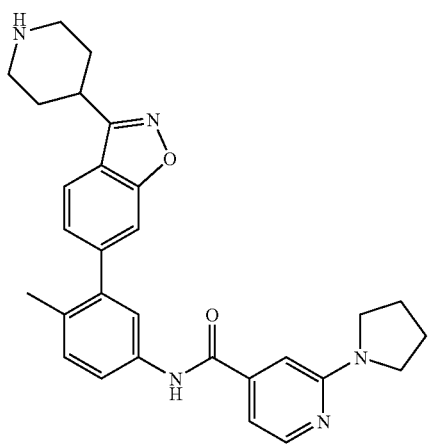

Example 3 was prepared by General Method A using 6-bromo-3-piperidin-4-yl-1,2-benzisoxazole and Intermediate 13.

NMR: δH [d6-DMSO] 10.3 (1H, s), 8.4 (1H, s), 8.2 (1H, d), 8.05 (1H,d), 7.75 (3H, m), 7.4 (1H, d), 7.3 (1H, d), 6.95 (1H, d), 6.85 (1H, s), 3.45 (4H, m), 3.2 (2H, d), 2.9 (2H, t), 2.25 (3H, s), 2.1 (2H, d), 1.95 (4H, m).

LCMS: Rt 2.26 min, MH+482.

Example 4

N-[4-Methyl-3-(3-methyl-1,2-benzisoxazol-6-yl)phenyl]-2-pyrrolidin-1-ylisonicotinamide

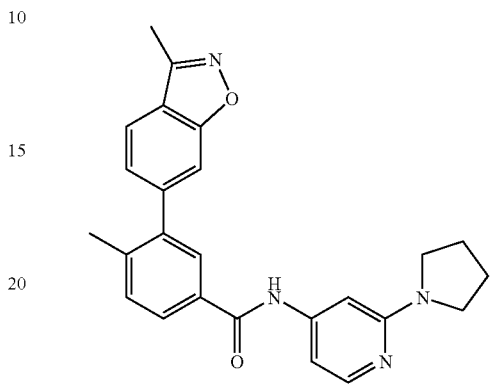

A mixture of 6-bromo-3-methyl-1,2-benzisoxazole (11 mg), N-[4-methyl-3-(4,4,5,5-tetramethyl-[1,3,2]dioxaborolan-2-yl)-phenyl]-2-pyrrolidin-1-yl-isonicotinamide (Intermediate 13, 15 mg) and aqueous sodium carbonate (0.5M, 0.25 ml) in anhydrous DME (1 ml) was degassed then stirred under nitrogen. A solution of tetrakis(triphenylphosphine) palladium(0) (2.5 mg) in DME (0.25 ml) was added and the mixture was stirred at 80° for 16 h. The solvent was removed under vacuum and the residue was partitioned between dichloromethane and water. The organic layer was separated using a hydrophobic filter, the solvent was evaporated and the residue was purified by column chromatography on silica, eluting with a cyclohexane-ethyl acetate gradient to give the title compound as an oil (5.6 mg).

NMR δH [d6-DMSO, 600 MHz] 10.3 (1H, br.s ), 8.18 (1H, d), 7.93 (1H, d ), 7.74 (1H,dd), 7.71 (1H,d), 7.67 (1H,s), 7.37 (1H,d), 7.37 (1H,d), 6.97 (1H,d), 6.86 (1H, s ), 3.43 (4H, br.t), 2.60 (3H, s), 2.22 (3H, s), 1.96 (4H, br.t).

LC-MS: Rt 2.91 min, MH+ 413.

Example 5

N-[4-Methyl-3-(3-methyl-1,2-benzisoxazol-6-yl)phenyl]thiophene-3-carboxamide

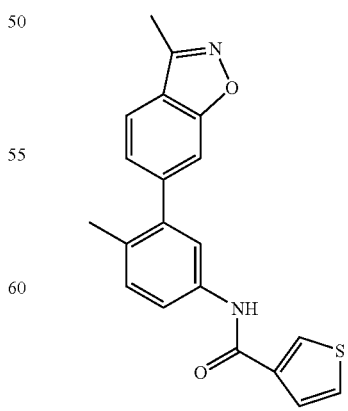

Example 5 was prepared in a similar manner to Example 4 using 6-bromo-3-methyl-1,2-benzisoxazole (11 mg) and N-[4-methyl-3-(4,4,5,5-tetramethyl-[1,3,2]dioxaborolan-2-yl)-phenyl]-3-thiopheneamide (Intermediate 15, 17 mg) to give an oil (8.5 mg).

NMR δH [d6-DMSO, 600 MHz] 10.06 (1H, br.s ), 8.32 (1H, dd,), 7.93 (1H, d), 7.73 (1H, dd), 7.69 (1H, d), 7.67 (1H, br.s ) 7.64. (1H, dd), 7.62 (1H, dd), 7.37 (1H, dd ), 7.31 (1H, d ), 2.60 (3H, s), 2.21 (3H, s).

LC-MS: Rt 3.51 min, MH+ 349.

Example 6

N-[4-Methyl-3-(3-methyl-1,2-benzisoxazol-6-yl)phenyl]-3-furamide

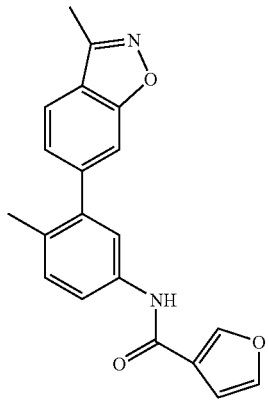

Example 6 was prepared in a similar manner to Example 4 using 6-bromo-3-methyl-1,2-benzisoxazole (11 mg) and N-[4-methyl-3-(4,4,5,5-tetramethyl-[1,3,2]dioxaborolan-2-yl)-phenyl]-3-furamide (Intermediate 17, 16 mg) to give the title compound as an oil (8.6 mg).

LC-MS: Rt 3.39, MH+ 333.

Example 7

4-Methyl-3-(3-methyl-1,2-benzisoxazol-6-yl)-N-(3-morpholin-4-ylphenyl)benzamide

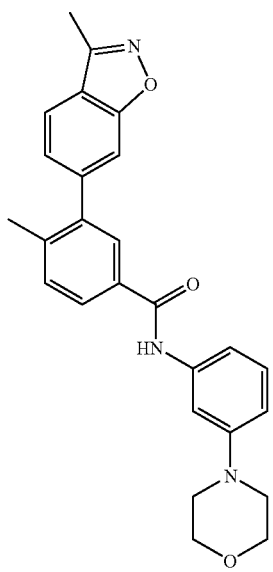

Example 7 was prepared in a similar manner to Example 4 using 6-bromo-3-methyl-1,2-benzisoxazole (11 mg) and 4-methyl-N-(3-morpholin-4-yl-phenyl)-3-(4,4,5,5-tetramethyl-[1,3,2]dioxaborolan-2-yl)-benzamide (Intermediate 9, 21 mg) to give the title compound as an oil (9.6 mg).

NMR δH [d6-DMSO, 600 MHz] 10.07 (1H, br.s), 7.96-7.88 (3H, m), 7.76 (1H, S), 7.50 (1H, d), 7.46 (1H, d), 7.38 (1, br.s), 7.28 (1H, br.d), 7.18 (1H, t), 6.70 (1H,dd), 3.74 (4H,m), 2.60 (3H,s), 2.32 (3H, s).

LC-MS: Rt 3.47 min, MH+ 428.

Example 8

4-Methyl-3-(3-methyl-1,2-benzisoxazol-6-yl)-N-(1,3-thiazol-2-yl)benzamide

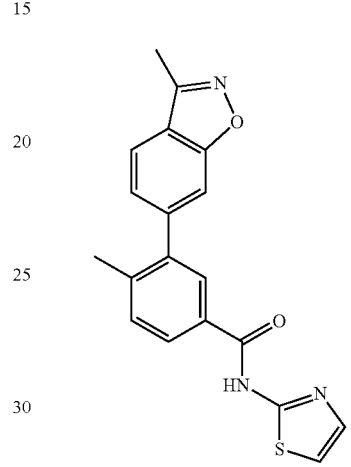

Example 8 was prepared in a similar manner to Example 4 using 6-bromo-3-methyl-1,2-benzisoxazole (11 mg) and N-(thiazol-2-yl)-4-methyl-3-(4,4,5,5-tetramethyl-[1,3,2]dioxaborolan-2-yl)-benzamide (Intermediate 18, 17 mg) followed by purification via mass directed autoprep to give the title compound as an oil (1.3 mg).

LC-MS: Rt 3.45 min, MH+ 350.

Example 9

N-Cyclopropyl-4-methyl-3-(3-methyl-1,2benzisoxazol-6-yl)benzamide

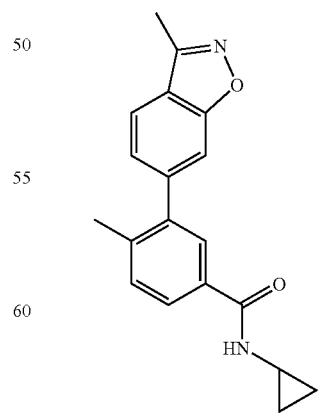

Example 9 was prepared in a similar manner to Example 4 using 6-bromo-3-methyl-1,2-benzisoxazole (11 mg) and N-cyclopropylmethyl-3-(4,4,5,5-tetramethyl-[1,3,2]dioxaborolan-2-yl)-benzamide (Intermediate 5, 15 mg) to give the title compound as an oil (8.5 mg).

NMR δH [d6-DMSO, 600 MHz] 8.43 (1H, br.d), 7.92 (1H, d), 7.78 (1H, dd ), 7.74 (1H, d), 7.70 (1H, s), 7.42-7.37 (2H, 2xd), 2.85 (1H, m), 2.60 (3H, s), 2.27 (3H, s), 0.67 (2H,m), 0.55 (2H,m).

LC-MS: Rt 3.19 min, MH+ 307.

Example 10

N-[4-Methyl-3-(3-methyl-1,2-benzisoxazol-5-yl)phenyl]-2-pyrrolidin-1-ylisonicotinamide

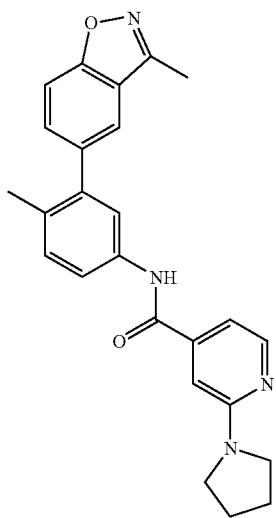

Example 10 was prepared in a similar manner to Example 4 using 5-bromo-3-methyl-1,2-benzisoxazole (11 mg) and N-[4-methyl-3-(4,4,5,5-tetramethyl-[1,3,2]dioxaborolan-2-yl)-phenyl]-2-pyrrolidin-1-yl-isonicotinamide (Intermediate 13, 16 mg) to give the title compound as an oil (6.6).

LC-MS: Rt 2.91 min, MH+ 413.

Example 11

N-Cyclopropyl-3-[3-({[2-hydroxy-1-(hydroxymethyl)ethyl]amino}methyl)-1,2-benzisoxazol-6-yl]-4-methylbenzamide

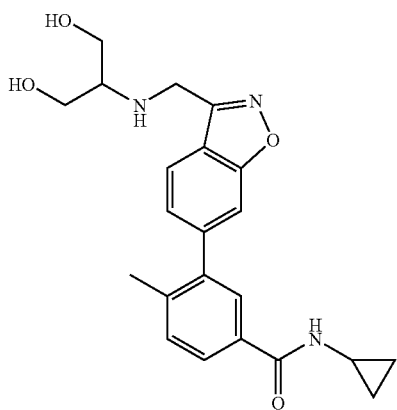

A mixture of 2-[(6-bromo-1,2-benzisoxazol-3-yl)methyl]amino-1,3-propanediol (Intermediate 2, 8 mg), N-cyclopropyl-4-methyl-3-(4,4,5,5-tetramethyl-[1,3,2]dioxaborolan-2-yl)-benzamide (Intermediate 5, 10 mg) aqueous sodium carbonate (1M, 0.1 ml) and tetrakis(triphenylphosphine)palladium(0) (1 mg) in 2-propanol (0.2 ml) was stirred at 80° under nitrogen for 18 h. The solvent was evaporated and the residue was purified on a Varian Bond-Elut SPE cartridge (silica, 500 mg) using a dichloromethane-methanol elution gradient (19:1 to 9:1) to give the title compound as an oil (3 mg).

NMR δH [d6-DMSO] 8.43 (1H, br.d), 8.08 (1H, d), 7.80 (1H, dd ), 7.75 (1H, d), 7.73 (1H, br.s), 7.40 (2H, 2xd), 4.48 (2H, br.t), 4.24 (2H, s), 3.42 (4H, m), 2.85 (1H, m), 2.61 (1H, m), 2.28 (3H, s), 0.72-0.53 (4H, m).

LC-MS: Rt 2.15 min, MH+ 396.

Example 12

N-(3-Methoxyphenyl)-4-methyl-3-(3-piperidin-4-yl-1,2-benzisoxazol-6-yl)benzamide

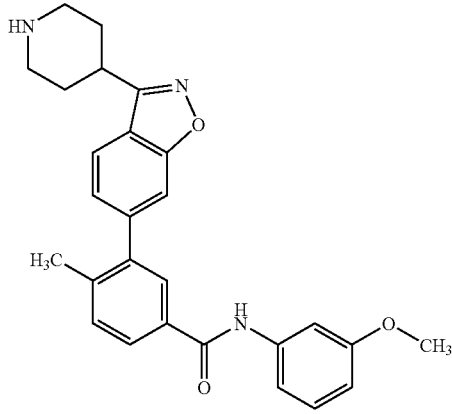

N-(3-Methoxyphenyl)-4-methyl-3-(4,4,5,5-tetramethyl-[1,3,2]dioxaborolan-2-yl)-benzamide (Intermediate 19, 54 mg), DME (3 ml), aqueous sodium carbonate (1M, 2 ml), tetrakis (triphenylphosphine) palladium (20 mg) and 6-bromo-3-piperidin-4-yl-1,2-benzisoxazole (44 mg) were heated together at 80° C. under nitrogen for 18 h. The solvent was evaporated and the residue was purified by column chromatography on silica (10 g) eluting with dichloromethane:ethanol:ammonia (40:8:1) to give the title compound (37 mg).

NMR: δH[d6-DMSO] 8.05 (1H, d), 7.88-7.97 (2H, m), 7.79 (1H, s), 7.50 (1H, d), 7.42-7.47 (2H, m), 7.36 (1H, br d), 7.23 (1H, dd), 6.67 (1H, dd), 3.09-3.14 (5H, m), 2.76 (2H, m), 2.32 (3H, s), 1.99 (2H, m), 1.83 (2H, m).

LCMS: Rt 2.66 min, MH+ 442.

Example 13

4-Methyl-3-(3-piperidin-4-yl-1,2-benzisoxazol-6-yl)-N-(1,3,4-thiadiazol-2-yl)benzamide

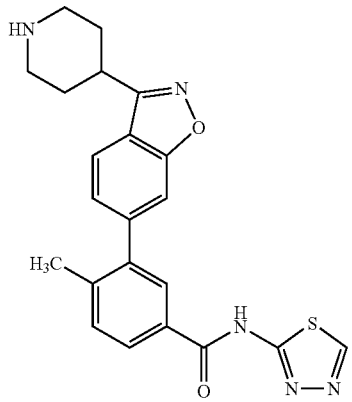

4-Methyl-3-(4,4,5,5-tetramethyl-[1,3,2]dioxaborolan-2-yl)-N-(thiadiazol-2-yl)-benzamide (Intermediate 20, 50.7 mg), DME (3 ml), aqueous sodium carbonate (1M, 2 ml), tetrakis (triphenylphosphine) palladium (20 mg) and 6-bromo-3-piperidinyl-4-yl-1,2-benzisoxazole (44 mg) were heated together at 80° C. under nitrogen for 18 h. The mixture was evaporated and the residue was purified by column chromatography on silica (10 g) eluting with cyclohexane:ethyl acetate (8:1 to 1:1) followed by dichloromethane:ethanol:ammonia (20:8:1) to give the title compound (30.1 mg).

NMR: δH[d6-DMSO] 8.95 (1H, s), 8.01-8.09 (4H, m), 7.80 (1H, s), 7.47 (1H, d), 7.45 (1H, d), 3.25-3.47 (3H, m), 2.97 (2H, dd), 2.32 (3H, s), 2.14 (2H, m), 1.97 (2H, m).

LCMS: Rt 2.44 min, MH+ 420.

Example 14

N-[4-Methyl-3-(3-piperidin-4-yl-1,2-benzisoxazol-6-yl)phenyl]thiophene-3-carboxamide

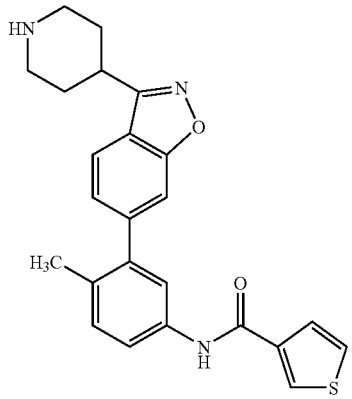

N-[4-Methyl-3-(4,4,5,5-tetramethyl-[1,3,2]dioxaborolan-2-yl)-phenyl]thiophene-3-amide (Intermediate 15, 50 mg), DMF (1.5 ml), aqueous sodium carbonate (1M, 0.75 ml), tetrakis (triphenylphosphine) palladium (7.5 mg) and 6-bromo-3-piperidin-4-yl-1,2-benzisoxazole (41 mg) were heated together at 80° C. under nitrogen for 18 h. The solvent was evaporated, and the residue was purified by column chromatography on silica (10 g) eluting with dichloromethane:ethanol:ammonia (100:8:1) to give the title compound (36.8 mg).

NMR: δH[d6-DMSO] 10.07 (1H, d), 8.32 (1H, s), 8.00 (1H, dd), 7.59-7.74 (4H, m), 7.35 (1H, d), 7.29 (1H, dd), 6.94 (1H, d), 3.02 (2H, m), 2.66 (2H, m), 2.20 (3H, s), 1.96 (1H, m), 1.78 (2H, m), 1.50 (1H, m).

LCMS: Rt 2.71 min, MH+ 418.

Example 15

N-[4-Methyl-3-(3-piperidin-4-yl-1,2-benzisoxazol-6-yl)phenyl]-3-furamide

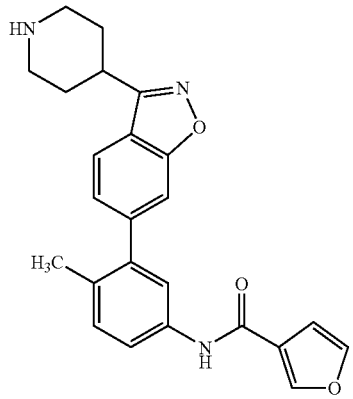

N-[4-Methyl-3-(4,4,5,5-tetramethyl-[1,3,2]dioxaborolan-2-yl)-phenyl]-3-furamide (Intermediate 17, 47 mg), DMF (1.5 ml), aqueous sodium carbonate (1M, 0.75 ml), tetrakis (triphenylphosphine) palladium (7.5 mg) and 6-bromo-3-piperidin-4-yl-1,2-benzisoxazole (41 mg) were heated together at 80° C. under nitrogen for 18 h. The solvent was evaporated and the residue was purified by column chromatography on silica (10 g) eluting with dichloromethane:ethanol:ammonia (100:8:1) to give the title compound (37.8 mg).

NMR: δH[d6-DMSO] 9.93 (1H, d), 8.35 (1H, s), 8.00 (1H, dd), 7.78 (1H, s), 7.61-7.69 (2H, m), 7.35 (1H, d), 7.28 (1H, dd), 6.98 (1H, s), 3.02 (2H, m), 2.65 (2H, m), 2.21 (3H, s), 1.96 (1H, m), 1.77 (2H, m), 1.49 (1H, m).

LCMS: Rt 2.55 min, MH+ 402.

Example 16

N-(Cyclopropylmethyl)-4-methyl-3-(3-piperidin-4-yl-1,2-benzisoxazol-6-yl)benzamide

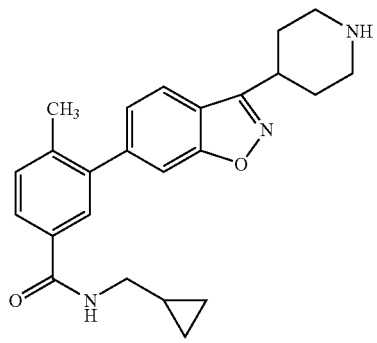

N-Cyclopropylmethyl-4-methyl-3-(4,4,5,5-tetramethyl-[1,3,2]dioxaborolan-2-yl)-benzamide (Intermediate 21, 100 mg), DME (5 ml), aqueous sodium carbonate (1M, 3 ml), tetrakis (triphenylphosphine) palladium (0) (37 mg) and 6-bromo-3-piperidin-4-yl-1,2-benzisoxazole (76 mg) were heated together at 80° C. under nitrogen for 18 h. The solvent was evaporated and the residue was purified by column chromatography on silica (10 g ) eluting with dichloromethane:ethanol:ammonia (100:8:1 to 70:8:1) to give the title compound (53 mg).

NMR: δH[d6-DMSO] 8.56 (1H, t), 8.03 (1H, d), 7.81 (1H, dd), 7.78 (1H, s), 7.74 (1H, s), 7.42 (1H, d), 7.38 (1H, d), 3.12 (2H, t), 3.05 (2H, m), 2.68 (2H, m), 2.29 (3H, s), 1.95 (2H, m), 1.78 (2H, m), 1.00 (1H, m), 0.41 (2H, m), 0.20 (2H, m).

LCMS: Rt 2.56 min, MH+ 390.

Example 17

N-Cyclopropyl-3-(1H-indazol-5-yl)-4-methylbenzamide

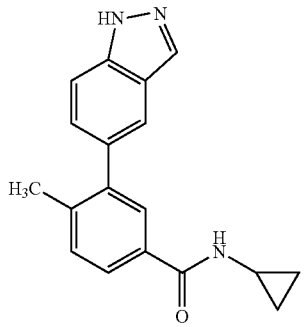

To a solution of tert-butyl 5-bromo-1H-indazole-1-carboxylate (Intermediate 3, 2.0 g) and N-cyclopropyl-4-methyl-3-(4,4,5,5-tetramethyl-[1,3,2]dioxaborolan-2-yl)-benzamide (Intermediate 5, 2.04 g) in DME (125 ml) was added tetrakis (triphenylphosphine) palladium (0.78 g) and aqueous sodium carbonate (1M, 80 ml). The mixture was heated at reflux under nitrogen for 16 h. The solvent was evaporated and the residue was purified by column chromatography on silica, eluting with cyclohexane:ethyl acetate (2:1 to 1:1) to give the title compound (1.38 g).

NMR: δH [CDCl₃] 8.10 (1H, s), 7.31-7.68 (7H, m), 6.26 (1H, br s), 2.89 (1H, m), 2.29 (3H, s), 0.86 (2H, m), 0.60 (2H, m).

LCMS: Rt 2.82 min, MH+ 292.

Example 18

N-Cyclopropyl-4-methyl-3-[1-(phenylsulfonyl)-1H-indazol-5-yl]benzamide

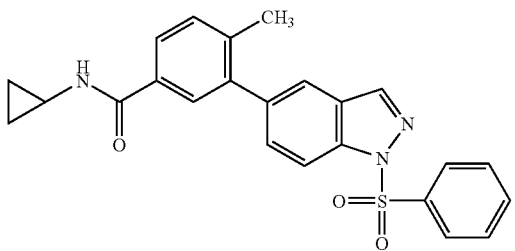

Example 18 was prepared by General Method B using benzenesulfonyl chloride to give the title compound (10.4 mg).

NMR: δH[d6-DMSO] 8.58 (1H, d), 8.38 (1H, d), 8.19 (1H, d), 7.97 (2H, d), 7.85 (1H, s), 7.62-7.77 (6H, m), 7.39 (1H, d), 2.82 (1H, m), 2.24 (3H, s), 0.65 (2H, m), 0.53 (2H, m).

LCMS: Rt 3.37 min, MH+ 432.

Example 19

N-Cyclopropyl-3-{1-[(3-fluorophenyl)sulfonyl]-1H-indazol-5-yl}-4-methylbenzamide

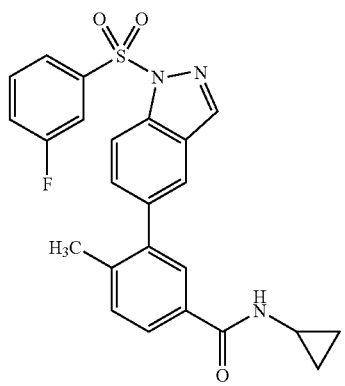

Example 19 was prepared by General Method B using 3-fluorobenzenesulfonyl chloride to give the title compound (19.2 mg).

NMR: δH[d6-DMSO] 8.62 (1H, s), 8.38 (1H, d), 8.20 (1H, d), 7.86 (1H, s), 7.60-7.84 (7H, m), 7.39 (1H, d), 2.82 (1H, m), 2.24 (3H, s), 0.65 (2H, m), 0.53 (2H, m).

LCMS: Rt 3.44 min, MH+ 450.

Example 20

3-{1-[(3-cyanophenyl)sulfonyl]-1H-indazol-5-yl}-N-cyclopropyl-4-methylbenzamide

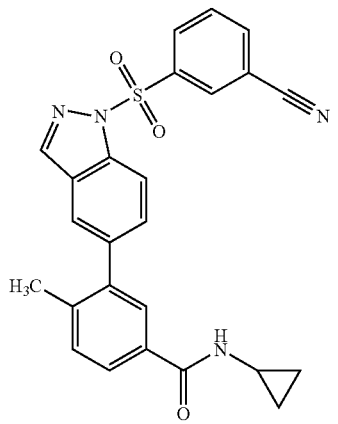

Example 20 was prepared by General Method B using 3-cyanobenzenesulfonyl chloride to give the title compound (14.5 mg).

NMR: δH[d6-DMSO] 8.64 (1H, s), 8.51 (1H, s), 8.39 (1H, d), 8.27 (1H, d), 8.21-8.24 (2H, m), 7.87 (1H, s), 7.83 (1H, dd), 7.76 (1H, d), 7.68-7.72 (2H, m), 7.39 (1H, d), 2.82 (1H, m), 2.24 (3H, s), 0.65 (2H1, m), 0.51 (2H, m).
LCMS: Rt 3.34 min, MH+ 457.

Example 21

N-Cyclopropyl-3-{1-[(3,4-difluorophenyl)sulfonyl]-1H-indazol-5-yl}-4-methylbenzamide

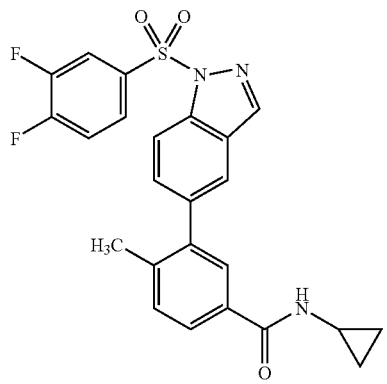

Example 21 was prepared by General Method B using 3,4-difluorobenzenesulfonyl chloride to give the title compound (15.6 mg).
NMR: δH[d6-DMSO] 8.63 (1H, s), 8.40 (1H, br d), 8.21 (1H, d), 8.16 (1H, td), 7.85-7.90 (2H, m), 7.65-7.80 (4H, m), 7.40 (1H, d), 2.82 (1H, m), 2.25 (3H, s), 0.67 (2H, m), 0.54 (2H, m).
LCMS: Rt 3.49 min, MH+ 468.

Example 22

N-Cyclopropyl-4-methyl-3-[1-(methylsulfonyl)-1H-indazol-5-yl]benzamide

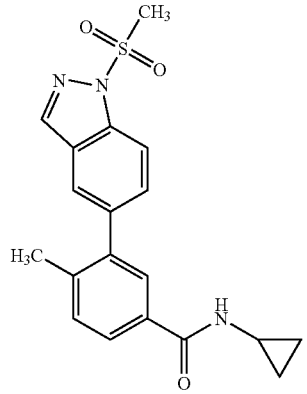

Example 22 was prepared by General Method B using methanesulfonyl chloride to give the title compound (6.9 mg).
NMR: δH[d6-DMSO] 8.64 (1H, s), 8.42 (1H, d), 8.03 (1H, d), 7.91 (1H, s), 7.76 (1H, d), 7.73 (1H, s), 7.66 (1H, dd), 7.40 (1H, d), 3.50 (3H, s), 2.84 (1H, m), 2.28 (3H, s), 0.67 (2H, m), 0.55 (2H, m).
LCMS: Rt 2.97 min, MH+ 370.

Example 23

N-Cyclopropyl-3-[1-(2,3-dihydro-1-benzofuran-5-ylsulfonyl)-1H-indazol-5-yl]-methylbenzamide

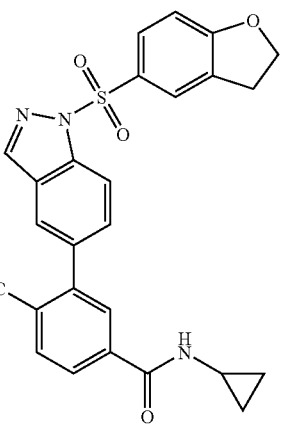

Example 23 was prepared by General Method B using 2,3-dihydro-1-benzofuran-5-sulfonyl chloride to give the title compound (9.2 mg).
NMR: δH[d6-DMSO] 8.54 (1H, s), 8.39 (1H, d), 8.17 (1H, d), 7.82-7.86 (2H, m), 7.74-7.77 (2H, m), 7.70 (1H, br s), 7.66 (1H, dd), 7.39 (1H, d), 6.93 (1H, d), 4.62 (2H, dd), 3.21 (2H, dd), 2.83 (1H, m), 2.25 (3H, s), 0.66 (2H, m), 0.54 (2H, m).
MS: e/z+ 474.

Example 24

N-Cyclopropyl-3-{1-[(3-methoxyphenyl)sulfonyl]-1H-indazol-5-yl}-4-methylbenzamide

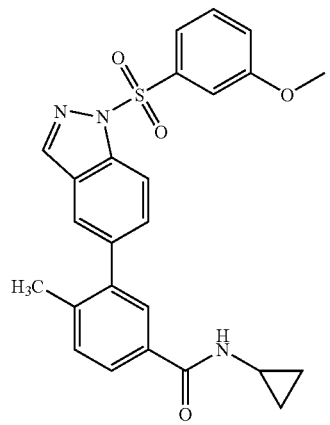

Example 24 was prepared by General Method B using 3-methoxyphenylsulfonyl chloride to give the title compound (11.0 mg).
NMR: δH[d6-DMSO] 8.59 (1H, s), 8.39 (1H, d), 8.19 (1H, d), 7.85 (1H, s), 7.76 (1H, d), 7.65-7.73 (2H, m), 7.49-7.54 (2H, m), 7.37-7.41 (2H, m), 7.30 (1H, d), 3.78 (3H, s), 2.82 (1H, m), 2.24 (3H, s), 0.66 (2H, m), 0.53 (2H, m).
LCMS: Rt 3.42 min, MH+ 462.

Example 25

3-[1-(Benzylsulfonyl)-1H-indazol-5-yl]-N-cyclopropyl-4-methylbenzamide

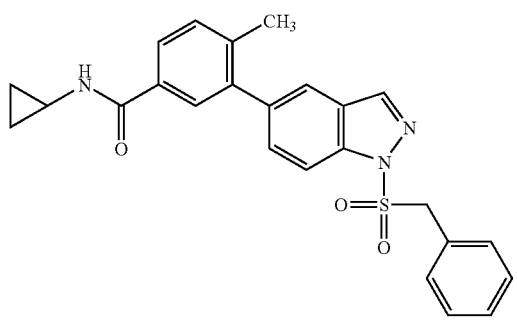

Example 25 was prepared by General Method B using benzylsulfonyl chloride to give the title compound (16.4 mg).

NMR: δH[d6-DMSO] 8.64 (1H, s), 8.41 (1H, d), 7.80 (1H, s), 7.75 (1H, dd), 7.67 (1H, d), 7.51 (1H, d), 7.37 (1H, dd), 7.18 (1H, dd), 7.12 (2H1, dd), 7.00 (2H, d), 5.02 (3H, s), 2.83 (1H, m), 2.21 (3H, s), 0.67 (2H, m), 0.54 (2H, m).

LCMS: Rt 3.34 min, MH+ 446.

Example 26

N-Cyclopropyl-3-{1-[(5-isoxazol-3-ylthien-2-yl)sulfonyl]-1H-indazol-5-yl}-4-methylbenzamide

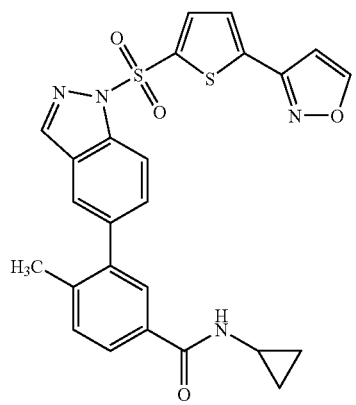

Example 26 was prepared by General Method B using 5-isoxazol-3-ylthiophene-2-sulfonyl chloride to give the title compound (3.5 mg).

NMR: δH[d6-DMSO] 8.73 (1H, s), 8.70 (1H, s), 8.39 (1H, d), 8.16 (1H, d), 8.03 (1H, d), 7.90 (1H, s), 7.69-7.79 (4H, m), 7.39 (1H, d), 7.16 (1H, d), 2.83 (1H, m), 2.25 (3H, s), 0.66 (2H, m), 0.52 (2H, m).

LCMS: Rt 3.46 min, MH+ 505.

Example 27

3-{1-[(4-Acetylphenyl)sulfonyl]-1H-indazol-5-yl}-N-cyclopropyl-4-methylbenzamide

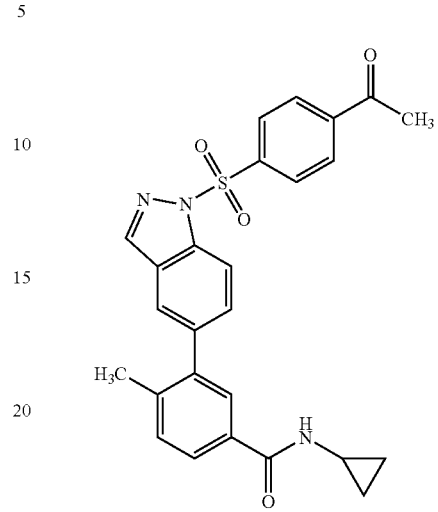

Example 27 was prepared by General Method B using 4-acetylphenylsulfonyl chloride to give the title compound (3.6 mg).

NMR: δH[d6-DMSO] 8.62 (1H, s), 8.38 (1H, d), 8.21 (1H, d), 8.10 (4H, m), 7.86 (1H, s), 7.76 (1H, dd), 7.69-7.71 (2H, m), 7.39 (1H, d), 2.83 (1H, m), 2.57 (3H, s), 2.24 (3H, s), 0.66 (2H, m), 0.52 (2H, m).

LCMS: Rt 3.32 min, MH+ 474.

Example 28

Methyl 4-{[(5-{5-[(cyclopropylamino)carbonyl]-2-methylphenyl}-1H-indazol-1-yl)sulfonyl]methyl}benzoate

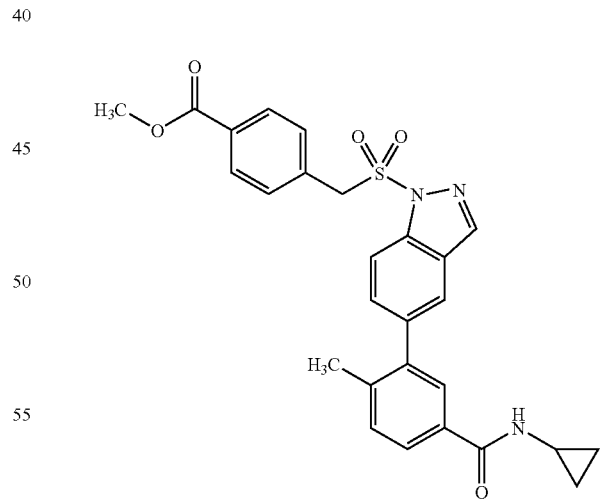

Example 28 was prepared by General Method B using methyl 4-[(chlorosulfonyl)methyl]benzoate to give the title compound (7.8 mg).

NMR: δH[d6-DMSO] 8.64 (1H, s), 8.39 (1H, d), 7.78 (1H, s), 7.74 (1H, d), 7.66 (2H, d), 7.64 (1H, s), 7.45 (1H, d), 7.37 (1H, d), 7.31 (1H, d), 7.11 (2H, d), 5.17 (2H, s), 3.76 (3H, s), 2.83 (1H, m), 2.13 (3H, s), 0.67 (2H, m), 0.54 (2H, m).

LCMS: Rt 3.38 min, MH+ 504.

Example 29

N-Cyclopropyl-3-{1-[(3,4-dimethoxyphenyl)sulfonyl]-1H-indazol-5-yl}-4-methylbenzamide

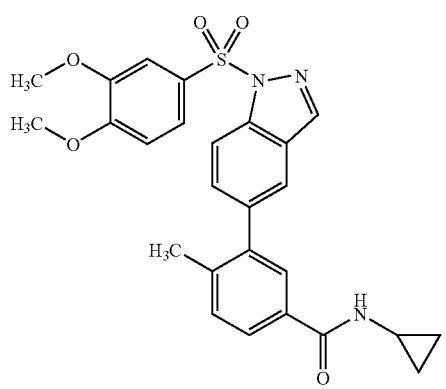

Example 29 was prepared by General Method B using 3,4-dimethoxybenzenesulfonyl chloride to give the title compound (4.2 mg).

NMR: δH[d6-DMSO] 8.56 (1H, s), 8.39 (1H, d),. 8.20 (1H, d), 7.84 (1H, s), 7.75 (1H, d), 7.70 (1H, s), 7.66 (1H, d), 7.57 (1H, dd), 7.39 (1H, d), 7.35 (1H, d), 7.14 (1H, d), 3.80 (3H, s), 3.77 (3H, s), 2.83 (1H, m), 2.24 (3H, s), 0.65 (2H, m), 0.53 (2H, m).

LCMS: Rt 3.29 min, MH+ 492.

Example 30

N-Cyclopropyl-4-methyl-3-(1-{[4-(trifluoromethyl)phenyl]sulfonyl}-1H-indazol-5-yl)benzamide

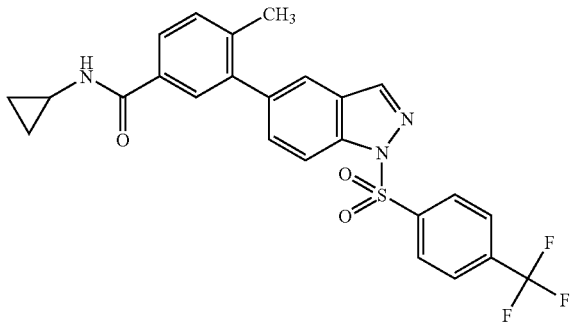

Example 30 was prepared by General Method B using 4-(trifluoromethyl)benzenesulfonyl chloride to give the title compound (13.3 mg).

NMR: δH[d6-DMSO 8.64 (1H, s), 8.39 (1H, d), 8.17-8.23 (3H, m), 8.02 (2H, d), 7.87 (1H, s), 7.76 (1H, d), 7.71 (1H, d), 7.70 (1H, s), 7.39 (1H, d), 2.83 (1H, m), 2.24 (3H, s), 0.65 (2H, m), 0.53 (2H, m).

LCMS: Rt 3.61 min, MH+ 500.

Example 31

N-Cyclopropyl-3-{1-[(4-fluorophenyl)sulfonyl]-1H-indazol-5-yl}-4-methylbenzamide

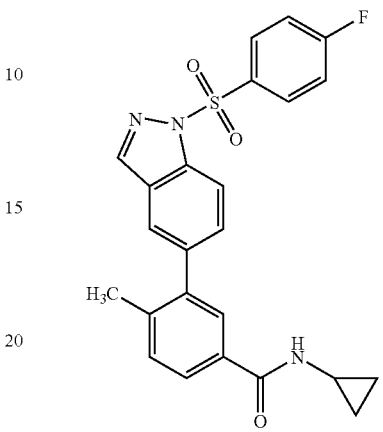

Example 31 was prepared by General Method B using 4-fluorobenzenesulfonyl chloride to give the title compound (13.3 mg).

NMR: δH[d6-DMSO] 8.39 (1H, s), 8.25 (1H, d), 8.06 (2H, dd), 7.76 (1H, s), 7.71 (1H, d), 7.66 (1H, s), 7.62 (1H, d), 7.38 (1H, d), 7.29 (2H, dd), 2.82 (1H, m), 2.27 (3H, s), 0.78 (2H, m), 0.61 (2H, m).

LCMS: Rt 3.41 min, MH+ 450.

Example 32

4-Methyl-3-(3-piperidin-4-yl-1,2-benzisoxazol-6-yl)-N-(1,3-thiazol-2-yl)benzamide

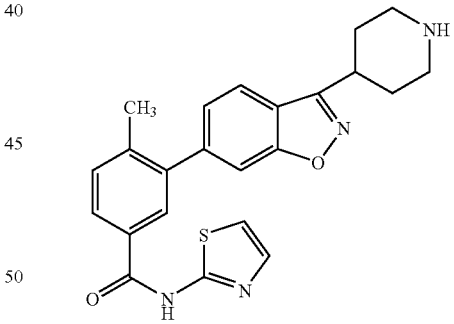

4-Methyl-3-(4,4,5,5-tetramethyl-[1,3,2]dioxaborolan-2-yl)-N-(thiazol-2-yl)-benzamide (Intermediate 18, 50 mg), DME (3 ml), aqueous sodium carbonate (1M, 2 ml), tetrakis(triphenylphosphine)palladium (20 mg) and 6-bromo-3-piperidin-4-yl-1,2-benzisoxazole (44 mg, 147 μmol) were heated together at 80° C. under nitrogen for 18 h. The solvent was evaporated, and the residue was purified by column chromatography on silica (10 g) eluting with dichloromethane:ethanol:ammonia (100:8:1) to give the title compound (43 mg).

NMR: δH[d6-DMSO] 8.00-8.09 (3H, m), 7.81 (1H, s), 7.44-7.52 (3H, m), 7.19 (1H, d), 3.08 (2H, m), 2.69 (2H, m), 2.34 (3H, s), 1.98 (2H, m), 1.80 (2H, m).

LCMS: Rt 2.53 min, MH+ 419.

Example 33

N-Cyclopropyl-4-methyl-3-[3-(1-piperazinyl)-1,2-benzisoxazol-6-yl]benzamide

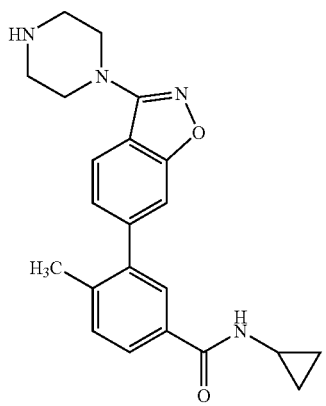

A solution of 1,1-dimethylethyl 4-(6-{5-[(cyclopropylamino)carbonyl]-2methylphenyl}-1,2-benzisoxazol-3-yl)-1-piperazinecarboxylate (Intermediate 26) in methanol (1 ml) was treated with a solution of hydrogen chloride in dioxan (4N, 1 ml) then stirred at room temp. for 18 h. The solvent was evaporated and the residue was re-dissolved in methanol and applied to an SCX cartridge (1 g). Elution with methanol followed by methanol:0.88 ammonia (99:1) gave the title compound as a white solid (0.016 g).

LCMS: Rt 2.31 min, MH+ 377.

Example 34

N-Cyclopropyl-4-methyl-3-[3-(4-morpholinyl)-1,2-benzisoxazol-6-yl]benzamide

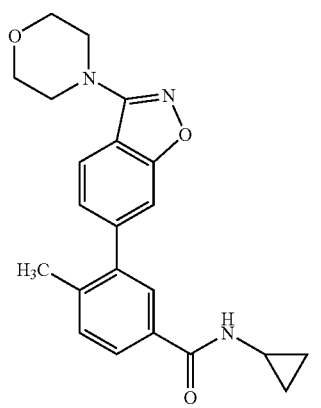

A mixture of 6-romo-3-(4-morpholinyl)-1,2-benzisoxazole (Intermediate 27) (0.016 g), N-Cyclopropyl-4-methyl-3-(4,4,5,5-tetramethyl-1,3,2dioxaborolan-2-yl)benzamide (Intermediate 5), (0.03 g) 2N aqueous sodium carbonate (1 ml) and tetrakis(triphenylphosphine)palladium(0) (0.5 mg) in isopropanol (3 ml) was stirred at reflux under nitrogen for 17 h. The residue was absorbed onto silica (Merck 7734) and applied to a Varian Bond-Elut SPE cartridge (silica, 5 g). Elution with dichloromethane:methanol (98:2) gave the title compound as a white solid (0.024 g).

LCMS: Rt 3.03 min, MH+ 378.

Example 35

N-Cyclopropyl-4-methyl-3-{3-[2-oxo-2-(1-piperazinyl)ethyl]-1,2-benzisoxazol-6-yl}benzamide

Example 36

Methyl (6-{5-[(cyclopropylamino)carbonyl]-2-methylphenyl}-1,2-benzisoxazol-3-yl)acetate

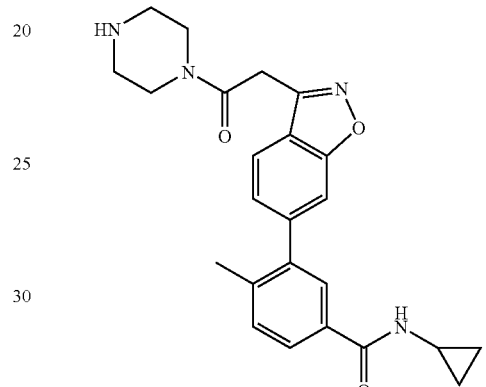

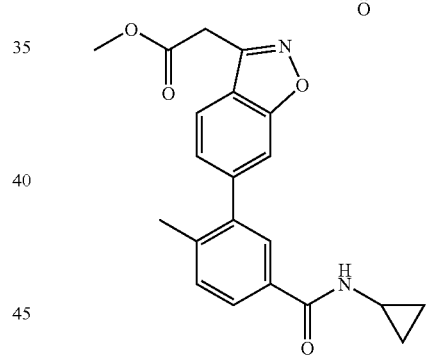

A suspension of 1,1-dimethylethyl 4-[(6-{5-[(cyclopropylamino)carbonyl]-2-methylphenyl}-1,2-benzisoxazol-3-yl)acetyl]-1-piperazinecarboxylate (Intermediate 34) (0.03 g) in methanol (1 ml) was treated with a solution of hydrogen chloride in dioxan (4M, 1 ml) to give a colourless solution which was stirred at room temp. for 18 h. The solvent was evaporated and the residue was partitioned between dichloromethane (2 ml) and 2M aqueous sodium carbonate (2 ml) The organic layer was applied to a Varian Bond-Elut SPE cartridge (silica, 5 g) and sequentially eluted with dichloromethane, ether, ethyl acetate, acetonitrile, acetone, dichloromethane:ethanol:0.88 ammonia (100:8:1) dichloromethane:ethanol:0.88 ammonia (40:8:1) ethanol and methanol to give Example 35 (6 mg) as a white solid and Example 36 (4 mg) as a white solid.

Example 35—LCMS: Rt 2.27 min, MH+ 419.

Example 36—LCMS: Rt 3.02 min, MH+ 365.

Example 37

N-Cyclopropyl-3-(3-{2-[(2-hydroxyethyl)amino]-2-oxoethyl}-1,2-benzisoxazol-6-yl)-4-methylbenzamide

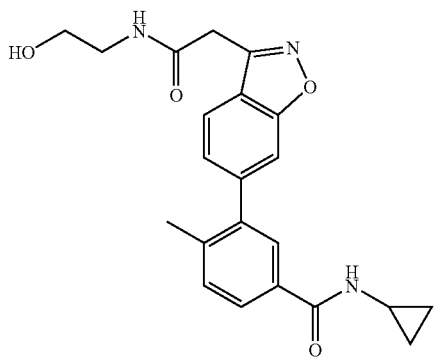

A mixture of N-cyclopropyl-4-methyl-3-(4,4,5,5-tetramethyl-1,3,2-dioxaborolan-2-yl)benzamide (Intermediate 5) (0.04 g) 2-(6-bromo-1,2-benzisoxazol-3-yl)-N-(2-hydroxyethyl)acetamide (Intermediate 35) (0.04 g) 2M aqueous sodium carbonate (1.5 ml) and tetrakis(triphenylphosphine)palladium(0) (1 mg) in isopropanol (3 ml) was stirred at reflux under nitrogen for 18 h. The mixture was absorbed onto silica (Merck 7734) and applied to a Varian Bond-Elut SPE cartridge (silica, 5 g) and eluted with a toluene:ethanol gradient (100:0 to 0:100) to give the title compound as a white solid (0.03 g).

LCMS: Rt 2.60 min, MH+ 394.

Example 38

N-Cyclopropyl-4-methyl-3-{3-[2-oxo-2-(1-piperidinyl)ethyl]-1,2-benzisoxazol-6-yl}benzamide

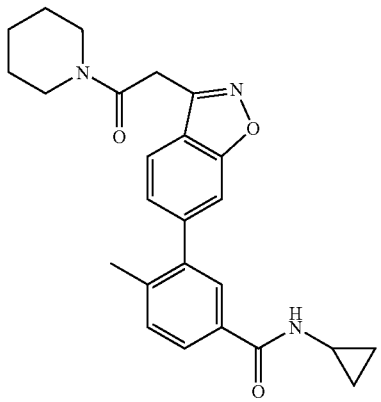

The procedure for Example 37 was followed using 6-bromo-3-[2-oxo-2-(1-piperidinyl)ethyl]-1,2-benzisoxazole (Intermediate 36) (0.04 g) in place of Intermediate 35 to give the title compound as a white solid (0.03 g).

LCMS: Rt 3.10 min, MH+ 418.

Example 39

N-Cyclopropyl-4-methyl-3-{3-[2-(methylamino)-2-oxoethyl]-1,2-benzisoxazol-6-yl}benzamide

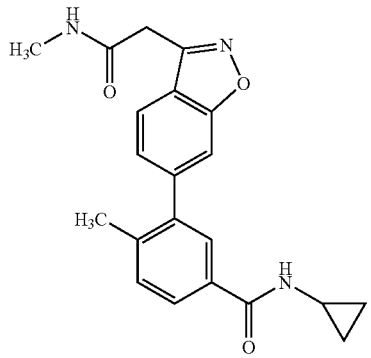

The procedure for Example 37 was followed 2-(6-bromo-1,2-benzisoxazol-3-yl)-N-methylacetamide (Intermediate 37) (0.04 g) in place of Intermediate 35 to give the title compound as a white solid (0.02 g).

LCMS: Rt 2.69 min, MH+ 364.

Example 40

N-Cyclopropyl-3-(3-{2-[(3-hydroxypronyl)amino]-2-oxoethyl}-1,2-benzisoxazol-6-yl)-4-methylbenzamide

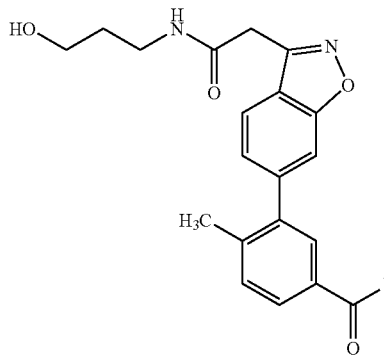

The procedure for Example 37 was followed 2-(6-bromo-1,2-benzisoxazol-3-yl)-N-(3-hydroxypropyl)acetamide (Intermediate 38) (0.04 g) in place of Intermediate 35 to give the title compound as a white solid (0.03 g).

LCMS: Rt 2.60 min, MH+ 408.

Example 41

N-Cyclopropyl-3-(3-{2-[(cyclopropylmethyl)amino]-2-oxoethyl}-1,2-benzisoxazol-6-yl)-4-methylbenzamide

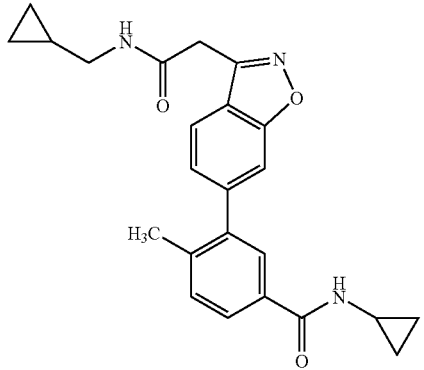

The procedure for Example 37 was followed 2-(6-bromo-1,2-benzisoxazol-3-yl)-N-(cyclopropylmethyl)acetamide (Intermediate 39) (0.04 g) in place of Intermediate 35 to give the title compound as a white solid (0.02 g).
LCMS: Rt 2.99 min, MH+ 404.

Example 42

N-Cyclopropyl-4-methyl-3-{3-[2-oxo-2-(1-pyrrolidinyl)ethyl]-1,2-benzisoxazol-6-yl}benzamide

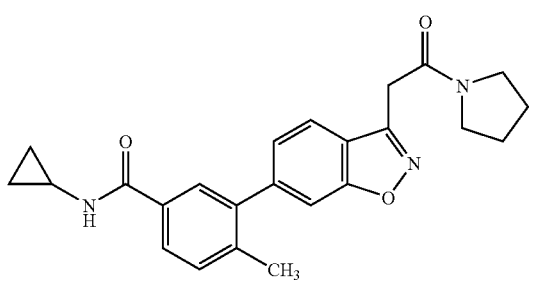

The procedure for Example 37 was followed using 6-bromo-3-[2-oxo-2-(1-pyrrolidinyl)ethyl]-1,2-benzisoxazole (Intermediate 40) (0.04 g) in place of Intermediate 35 to give the title compound as a white solid (0.01 g).
LCMS: Rt 3.19 min, MH+ 404.

Example 43

N-Cyclopropyl-3-{3-[2-(ethylamino)-2-oxoethyl]-1,2-benzisoxazol-6-yl}-4-methylbenzamide

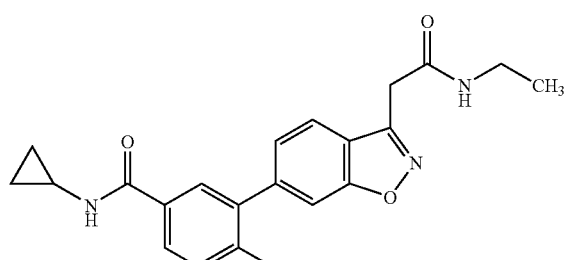

The procedure for Example 37 was followed using 2-(6-bromo-1,2-benzisoxazol-3-yl)-N-ethylacetamide (Intermediate 41) (0.04 g) in place of Intermediate 35 to give the title compound as a white solid (0.02 g).
LCMS: Rt 2.81 min, MH+ 378.

Example 44

N-Cyclopropyl-3-{3-[2-(cyclopropylamino)-2-oxoethyl]-1,2-benzisoxazol-6-yl}-4-methylbenzamide

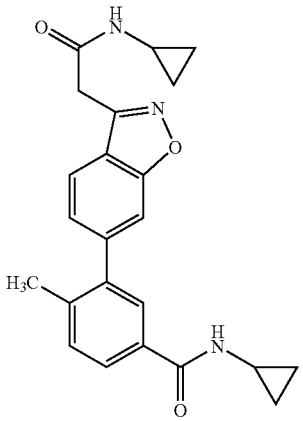

The procedure for Example 37 was followed using 2-(6-bromo-1,2-benzisoxazol-3-yl)-N-cyclopropylacetamide (Intermediate 42) (0.04 g) in place of Intermediate 35 to give the title compound as a white solid (0.02 g).
LCMS: Rt 2.83 min, MH+ 390.

Example 45

N-Cyclopropyl-4-methyl-3-{3-[2-(4-morpholinyl)-2-oxoethyl]-1,2-benzisoxazol-6-yl}benzamide

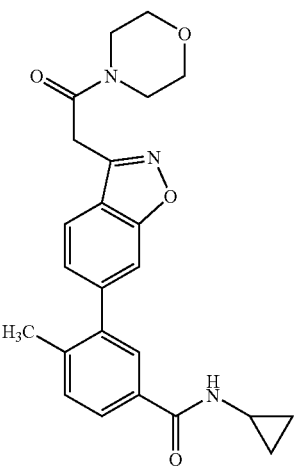

The procedure for Example 37 was followed using 6-bromo-3-[2-(4-morpholinyl)-2-oxoethyl]-1,2-benzisoxazole (Intermediate 43) (0.04 g) in place of Intermediate 35 to give the title compound as a white solid (0.02 g).
LCMS: Rt 2.79 min, MH+ 420.

Example 46

N-Cyclopropyl-4-methyl-3-{3-[2-({[3-(methyloxy)phenyl]methyl}amino)-2-oxoethyl]-1,2-benzisoxazol-6-yl}benzamide

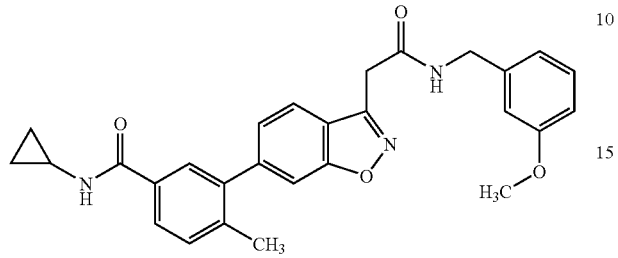

The procedure for Example 37 was followed using 2-(6-bromo-1,2-benzisoxazol-3-yl)-N-{[3-(methyloxy)phenyl]methyl}acetamide (Intermediate 44) (0.05 g) in place of Intermediate 35 to give the title compound as a white solid (0.02 g).

LCMS: Rt 3.16 min, MH+ 470.

Example 47

N-Cyclopropyl-4-methyl-3-{3-[2-oxo-2-(1,3-thiazol-2-ylamino)ethyl]-1,2-benzisoxazol-6-yl}benzamide

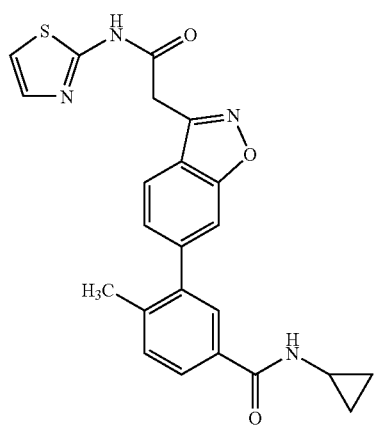

The procedure for Example 37 was followed using 2-(6-bromo-1,2-benzisoxazol-3-yl)-N-1,3-thiazol-2-ylacetamide (Intermediate 45) (0.03 g) in place of Intermediate 35. The SPE cartridge was eluted with cyclohexane:ethyl acetate (100:0 to 50:50) to give the title compound as a white solid (0.005 g).

LCMS: Rt 3.06 min, MH+ 433.

Example 48

N-Cyclopropyl-4-methyl-3-{3-[(4-methyl-1-piperazinyl)methyl]-1,2-benzisoxazol-6-yl}benzamide

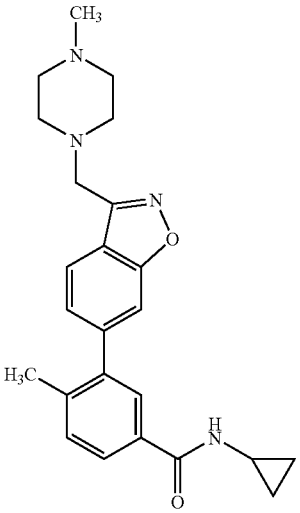

A mixture of 6-bromo-3-[(4-methyl-1-piperazinyl)methyl]-1,2-benzisoxazole (Intermediate 46) (0.02 g) N-cyclopropyl-4-methyl-3-(4,4,5,5-tetramethyl-1,3,2-dioxaborolan-2-yl)benzamide (Intermediate 5) (0.02 g) 2N aqueous sodium carbonate and tetrakis(triphenylphosphine)palladium(0) (1 mg) in isopropanol (0.3 ml) was heated in a Reactivial™ at 65° for 18 h. the reaction mixture was partitioned between water and ethyl acetate, the phases were separated and the aqueous layer was re-extracted with ethyl acetate. The combined organic extracts were washed with water (×2) and brine, dried using a hydrophobic filter tube and concentrated under a stream of nitrogen. The residue was purified by reverse phase preparative Hplc to give the title compound as a white foam (0.006 g).

LCMS: Rt 2.26 min, MH+ 405.

Example 49

N-Cyclopropyl-4-methyl-3-[3-(1-piperidinylmethyl)-1,2-benzisoxazol-6-yl]benzamide

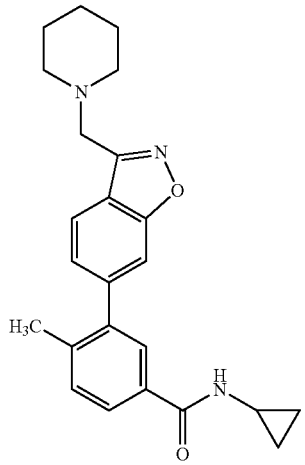

The procedure for Example 48 was followed using 6-bromo-3-(1-piperidinylmethyl)-1,2-benzisoxazole (Intermediate 47) (0.015 g) in place of Intermediate 46 to give the title compound as a white foam (0.005 g).

LCMS: Rt 2.28 min, MH+ 390.

Example 50

N-Cyclopropyl-4-methyl-3-[3-(4-morpholinylmethyl)-1,2-benzisoxazol-6-yl]benzamide

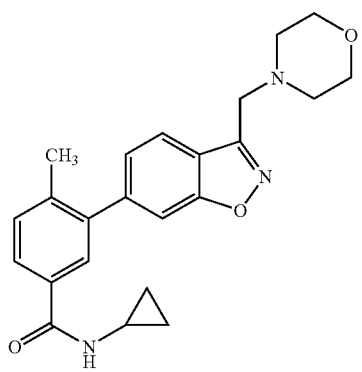

The procedure for Example 48 was followed using 6-bromo-3-(4-morpholinylmethyl)-1,2-benzisoxazole (Intermediate 48) (0.025 g) in place of Intermediate 46 to give the title compound as a white foam (0.002 g).

LCMS: Rt 2.64 min, MH+ 392.

Example 51

N-Cyclopropyl-4-methyl-3-[3-(1-pyrrolidinylmethyl)-1,2-benzisoxazol-6-yl]benzamide

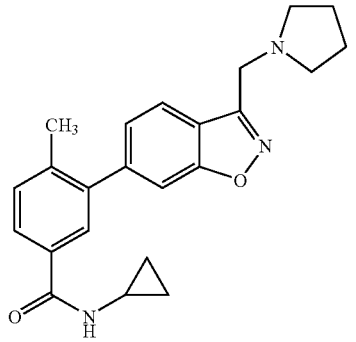

The procedure for Example 48 was followed using 6-bromo-3-(1-pyrrolidinylmethyl)-1,2-benzisoxazole (Intermediate 49) (0.015 g) in place of Intermediate 46 to give the title compound as a white foam (0.002 g).

LCMS: Rt 2.24 min, MH+ 376.

Example 52

3-(3-Amino-1,2-benzisoxazol-6-yl)-N-cyclopropyl-4-methylbenzamide

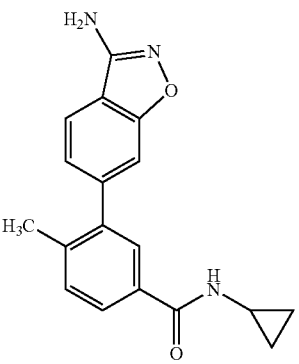

A mixture of 3-amino6-bromo-1,2-benzisoxazole (0.04 g) N-cyclopropyl-4-methyl-3-(4,4,5,5-tetramethyl-1,3,2-dioxaborolan-2-yl)benzamide (Intermediate 5) (0.07 g) and saturated aqueous sodium hydrogen carbonate (0.25 ml) was stirred under nitrogen, treated with tetrakis(triphenylphosphine)palladium(0) then heated at reflux for 6 h. Ethyl acetate (2 ml) and water (2 ml) were added to the cooled mixture and the phases were separated. The organic layer was washed with brine, dried using a hydrophobic filter tube and concentrated under a stream of nitrogen. The residue was purified by reverse phase preparative Hplc to give the title compound as a white foam (0.006 g).

LCMS: Rt 2.75 min, MH+ 308.

Example 53

N-Cyclopropyl-3-[3-(cyclopropylamino)-1,2-benzisoxazol-6-yl]-5-fluoro-4-methylbenzamide

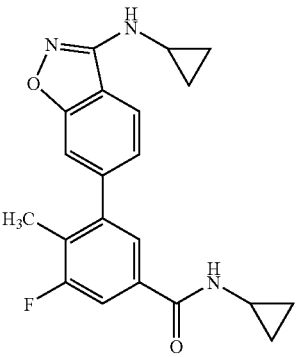

A mixture of 6-bromo-N-cyclopropyl-1,2-benzisoxazol-3-amine (Intermediate 53) (0.02 g) N-cyclopropyl-3-fluoro-4-methyl-5-(4,4,5,5-tetramethyl-1,3,2-dioxaborolan-2-yl)benzamide (Intermediate 62) (0.02 g) saturated aqueous sodium hydrogen carbonate (0.5 ml) and tetrakis(triphenykphosphine)palladium(0) in isopropanol (2 ml) was heated in a microwave at 150° for 10 min. The residue was absorbed onto silica Merck 7734) and applied to a Varian Bond Elut SPE cartridge (silica, 5 g) elutin with cyclohexane:ethyl acetate (75:25 to 0:100) to give the title compound (10 mg).
LCMS: Rt 3.20, MH+ 366.

Example 54

6-{5-[(Cyclopropylamino)carbonyl]-3-fluoro-2-methylphenyl}-N-(cyclopropylmethyl)-1,2-benzisoxazole-3-carboxamide

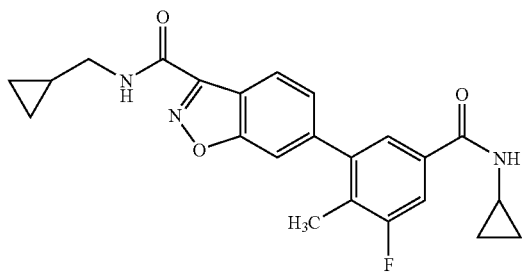

A mixture of 6-bromo-N-(cyclopropylmethyl)-1,2-benzisoxazole-3-carboxamide (Intermediate 56) (0.03 g) N-cyclopropyl-3-fluoro-4-methyl-5-(4,4,5,5-tetramethyl-1,3,2-dioxaborolan-2-yl)benzamide (Intermediate 62) (0.03 g) saturated aqueous sodium hydrogen carbonate (0.25 ml) and tetrakis(triphenylphosphine)palladium(0) (1 mg) in isopropanol (0.5 ml) was stirred at reflux under nitrogen for 4 h. Ethyl acetate (2 ml) and water (2 ml) were added, the phases were separated and the aqueous layer was re-extracted with ethyl acetate. The combined organic extracts were washed with brine, dried using a hydrophobic filter tube and concentrated under a stream of nitrogen. The residue was purified on Varian Bond-Elut SPE cartridge (silica, 1 g) eluting with cyclohexane:ethyl acetate (100:0 to 50:50) to give the title compound as a colourless foam (0.03 g).
LCMS: Rt 3.37 min, MH+ 408.

Example 55

6-{5-[(Cyclopropylamino)carbonyl]-3-fluoro-2-methylphenyl}-N-propyl-1,2-benzisoxazole-3-carboxamide

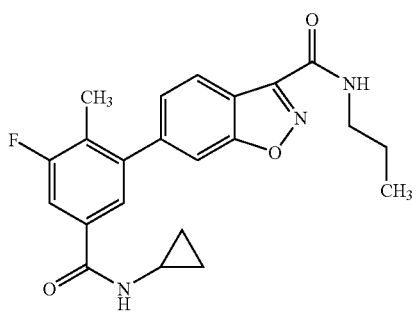

The procedure for Example 54 was followed using 6-bromo-N-propyl-1,2-benzisoxazole-3-carboxamide (Intermediate 57) (0.04 g) in place of Intermediate 56 to give the title compound as a yellow foam (0.02 g).
LCMS: Rt 3.32 min, MH+ 396.

Example 56

6-{5-[(Cyclopropylamino)carbonyl]-3-fluoro-2-methylphenyl}-N-methyl-1,2benzisoxazole-3-carboxamide

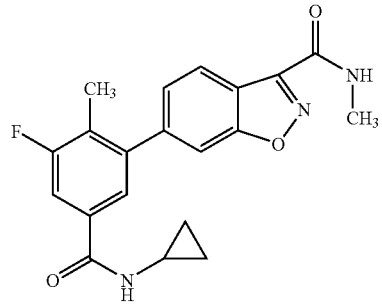

The procedure for Example 54 was followed using 6-bromo-N-methyl-1,2-benzisoxazole-3-carboxamide (Intermediate 58) (0.04 g) in place of Intermediate 56 to give the title compound as a yellow foam (0.02 g).
LCMS: Rt 3.04 min, MH+ 368.

Example 57

6-{5-[(Cyclopropylamino)carbonyl]-3-fluoro-2-methylphenyl}-N,N-dimethyl-1,2-benzisoxazole-3-carboxamide

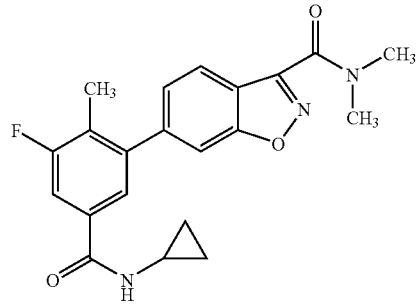

The procedure for Example 54 was followed using 6-bromo-N,N-dimethyl-1,2-benzisoxazole-3-carboxamide (Intermediate 59) (0.04 g) in place of Intermediate 56 to give the title compound as a yellow foam (0.02 g).
LCMS: Rt 3.05 min, MH+ 382.

Example 58

N-Cyclopropyl-6-{5-[(cyclopropylamino)carbonyl]-3-fluoro-2-methylphenyl}-1,2-benzisoxazole-3-carboxamide

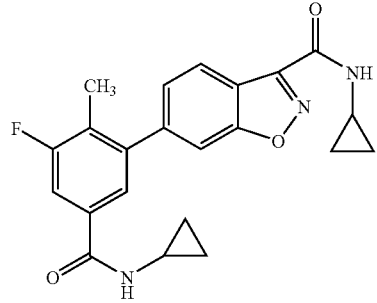

The procedure for Example 54 was followed using 6-bromo-N-cyclopropyl-1,2-benzisoxazole-3-carboxamide (Intermediate 60) (0.04 g) in place of Intermediate 56 to give the title compound as a yellow foam (0.02 g).
LCMS: Rt 3.18 min, MH+ 394.

Example 59

1,1-Dimethylethyl 5-{5-[(cyclopropylamino)carbonyl]-3-fluoro-2-methylphenyl}-1H-indazole-1-carboxylate

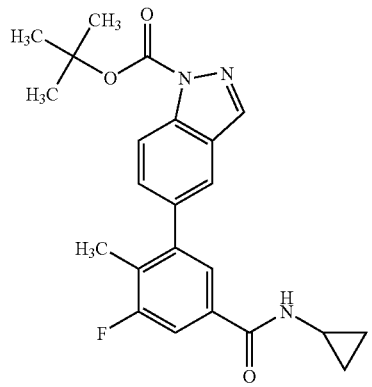

A mixture of tert-butyl 5-bromo-1H-indazole-1-carboxylate (Intermediate 3) (1.07 g) {5-[(cyclopropylamino)carbonyl]-3-fluoro-2-methylphenyl}boronic acid (Intermediate 64) (0.85 g) sodium carbonate (1.9 g) and tetrakis(triphenylphosphine)palladium(0) (0.42 g) in 1,2-dimethoxyethane (70 ml) was stirred at reflux under nitrogen for 20 h. the solvent was removed and the residue was partitioned between water (50 ml) and ethyl acetate (50 ml). The aqueous layer was re-extracted with ethyl acetate (3×30 ml) and the combined organic extracts were dried using a hydrophobic filter tube and concentrated under vacuum. The residue was purified by column chromatography on silica eluting with cyclohexane:ethyl acetate (75:25 to 60:40) to give the title compound (3.1 g).
LCMS: Rt 3.46 min, MH+ 410.

Example 60

N-Cyclopropyl-3-fluoro-5-(1H-indazol-5-yl)-4-methylbenzamide

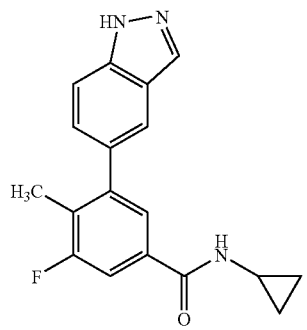

A mixture of 1,1-dimethylethyl 5-{5-[(cyclopropylamino)carbonyl]-3-fluoro-2-methylphenyl}-1H-indazole-1-carboxylate (Example 59) (0.46 g) in a solution of hydrogen chloride in dioxan (4M, 7 ml) was stirred at room temp. under nitrogen for 4.5 h. The solvent was evaporated and the residue was partitioned between dichloromethane (20 ml) and aqueous sodium hydroxide (2M, 20 ml). The organic layer was separated using a hydrophobic filter tube, the solvent was evaporated and the residue was purified on a Varian Bond-Elut SPE cartridge (silica, 10 g) eluting with chloroform:methanol (100:0 to 98:2) to give the title compound (0.06 g).
LCMS: Rt 2.96 min, MH+ 310.

Example 61

N-Cyclopropyl-4-methyl-3-{1-[(1-methylethyl)sulfonyl]-1H-indazol-5-yl}benzamide

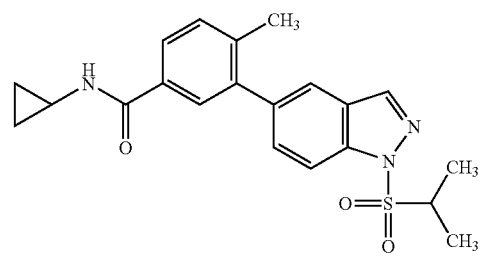

Prepared by General Method C. See Table.

Example 62

N-Cyclopropyl-3-[1-(ethylsulfonyl)-1H-indazol-5-yl]-4-methylbenzamide

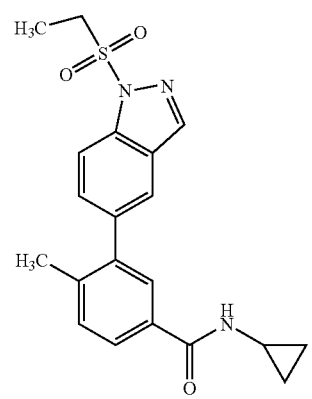

Prepared by General Method C. See Table.

Example 63

N-Cyclopropyl-3-[1-(cyclopropylsulfonyl)-1H-indazol-5-yl]-4-methylbenzamide

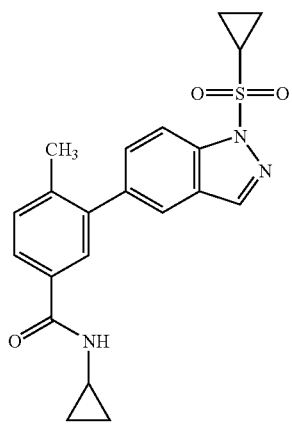

Prepared by General Method C. See Table.

Example 64

Methyl 5-[(5-{5-[(cyclopropylamino)carbonyl]-2-methylphenyl}-1H-indazol-1-yl)sulfonyl]-2-furancarboxylate

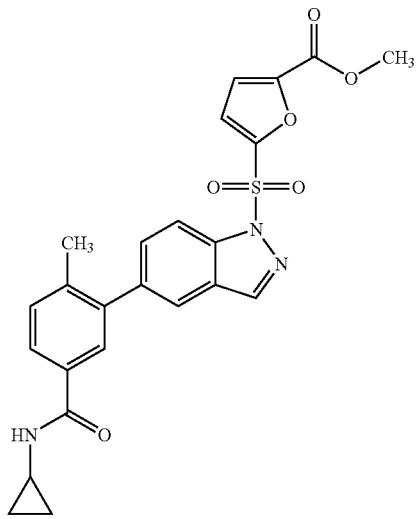

Prepared by General Method C. See Table.

Example 65

3-[1-(2,1,3-Benzoxadiazol-4-ylsulfonyl)-1H-indazol-5-yl]-N-cyclopropyl-4-methylbenzamide

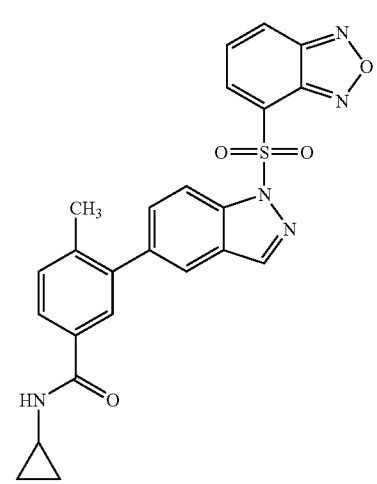

Prepared by General Method C. See Table.

Example 66

N-Cyclopropyl-3-{1-[(2-fluorophenyl)sulfonyl]-1H-indazol-5-yl}-4-methylbenzamide

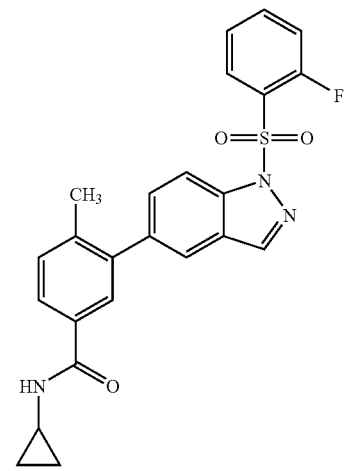

Prepared by General Method C. See Table.

Example 67

N-Cyclopropyl-4-methyl-3-{1[(4-methylphenyl)sulfonyl]-1H-indazol-5-yl}benzamide

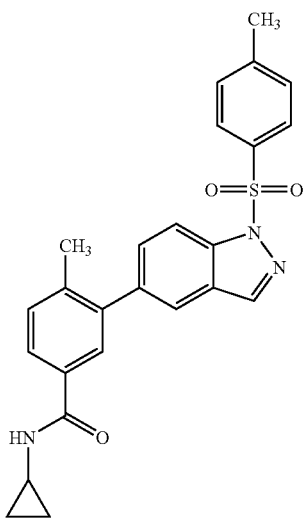

Prepared by General Method C. See Table.

Example 68

N-Cyclopropyl-4-methyl-3-[1-(2-thienylsulfonyl)-1H-indazol-5-yl]benzamide

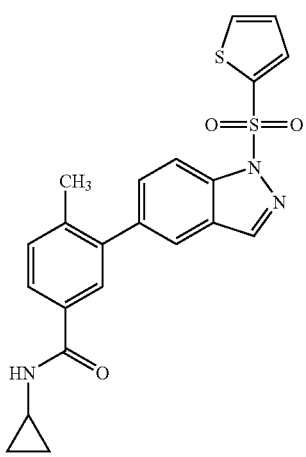

Prepared by General Method C. See Table.

Example 69

N-Cyclopropyl-3-{1-[(3,5-dimethyl-4-isoxazolyl)sulfonyl]-1H-indazol-5-yl}-4-methylbenzamide

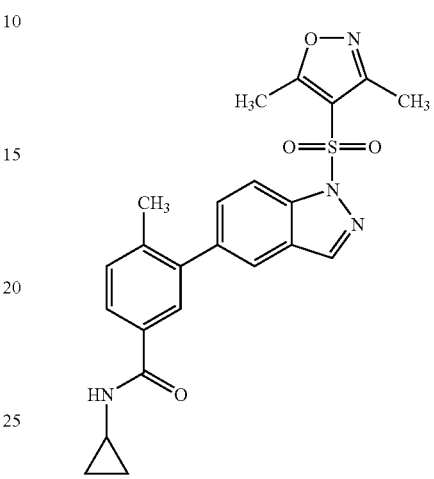

Prepared by General Method C. See Table.

Example 70

N-Cyclopropyl-4-methyl-3-[1-(propylsulfonyl)-1H-indazol-5-yl]benzamide

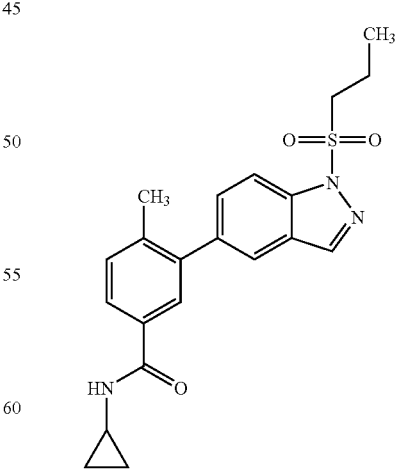

Prepared by General Method C. See Table.

95

Example 71

N-Cyclopropyl-4-methyl-3-{1-[(2-nitrophenyl)sulfonyl]-H-indazol-5-yl}benzamide

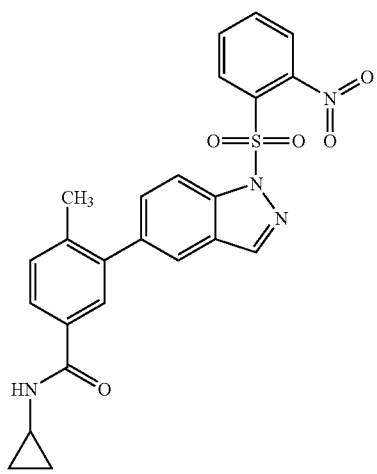

Prepared by General Method C. See Table.

Example 72

N-Cyclopropyl-4-methyl-3-{1-[(2,2,2-trifluoroethyl)sulfonyl]-1H-indazol-5-yl}benzamide

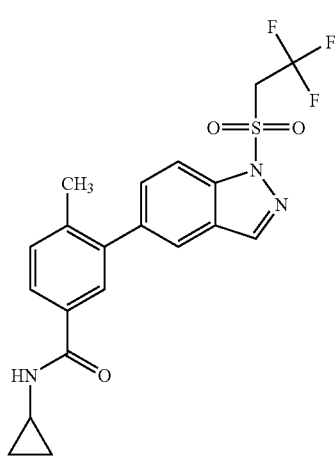

Prepared by General Method C. See Table.

96

Example 73

3-{1-[(2-Cyanophenyl)sulfonyl]-1H-indazol-5-yl}-N-cyclopropyl-4-methylbenzamide

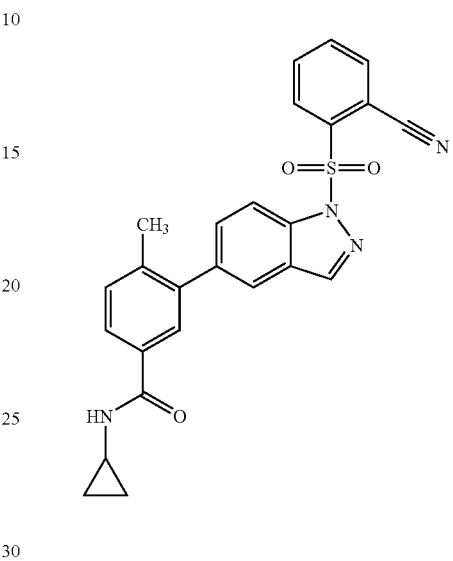

Prepared by General Method C. See Table.

Example 74

N-Cyclopropyl-4-methyl-3-{1-[(1,3,5-trimethyl-1H-pyrazol-4-yl)sulfonyl]-1H-indazol-5-yl}benzamide

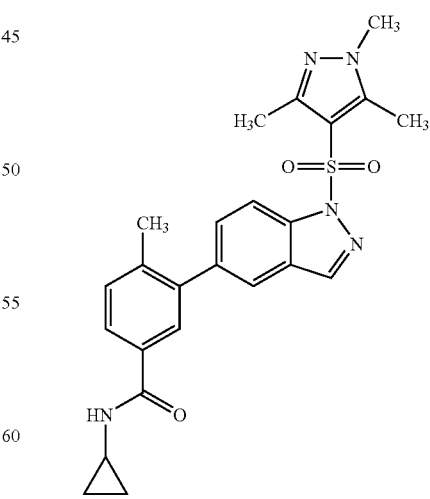

Prepared by General Method C. See Table.

Example 75

N-Cyclopropyl-4-methyl-3-{1-[(1-methyl-1H-imidazol-4-yl)sulfonyl]-1H-indazol-5-yl}benzamide

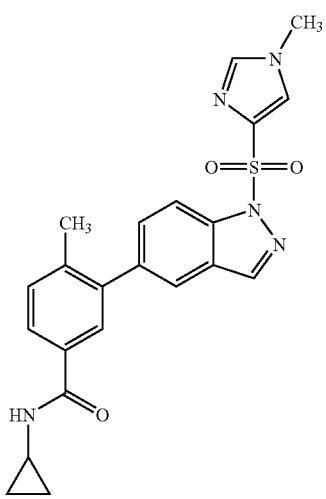

Prepared by General Method C. See Table.

Example 76

N-Cyclopropyl-3-fluoro-4-methyl-5-[1-(2-thienylsulfonyl)-1H-indazol-5-yl]benzamide

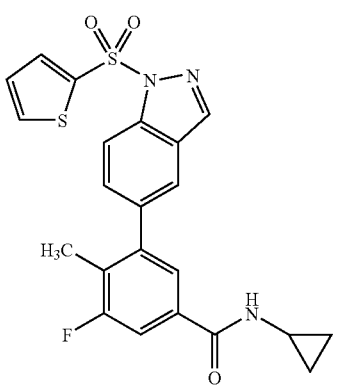

Prepared by General Method C. See Table.

Example 77

N-Cyclopropyl-3-fluoro-4-methyl-5-[1-(3-thienylsulfonyl)-1H-indazol-5-yl]benzamide

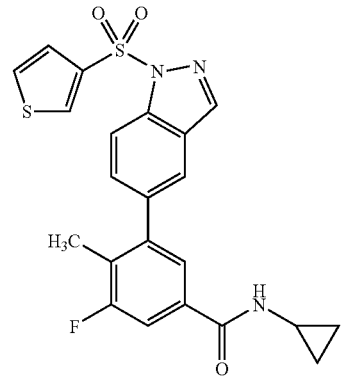

Prepared by General Method C. See Table.

Example 78

N-Cyclopropyl-3-fluoro-4-methyl-5-{1-[(4-methylphenyl)sulfonyl]-1H-indazol-5-yl}benzamide

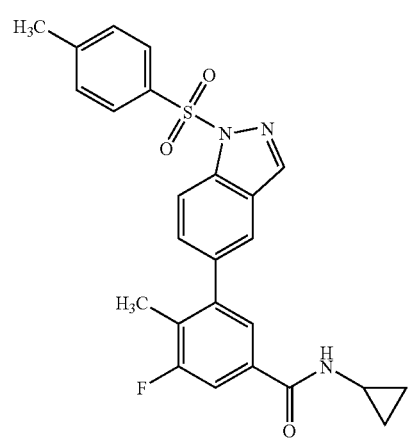

Prepared by General Method C. See Table.

Example 79

N-Cyclopropyl-3-fluoro-4-methyl-5-(1-{[4-(methyloxy)phenyl]sulfonyl}-1H-indazol-5-yl)benzamide

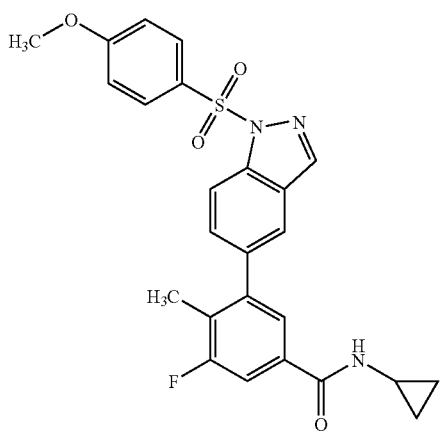

Prepared by General Method C. See Table.

Example 80

N-Cyclopropyl-3-fluoro-4-methyl-5-(1-{[4-(1-methylethyl)phenyl]sulfonyl}-1H-indazol-5-yl)benzamide

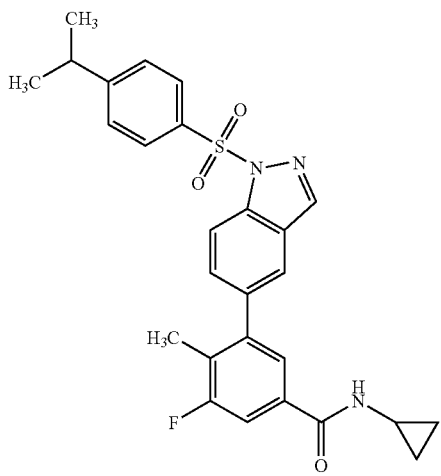

Prepared by General Method C. See Table.

Example 81

3-{1-[(4-Chlorophenyl)sulfonyl]-1H-indazol-5-yl}-N-cyclopropyl-5-fluoro-4-methylbenzamide

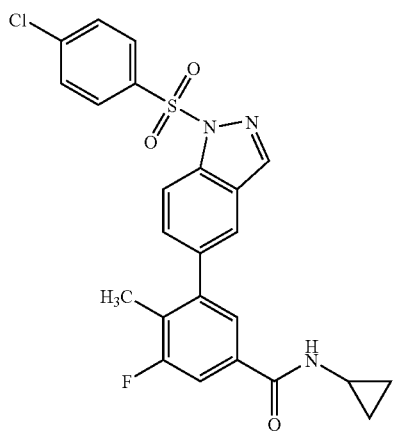

Prepared by General Method C. See Table.

Example 82

N-Cyclopropyl-3-{1-[(2,4-difluorophenyl)sulfonyl]-1H-indazol-5-yl}-5-fluoro-4-methylbenzamide

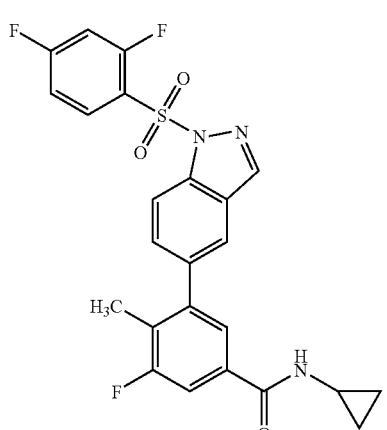

Prepared by General Method C. See Table.

Example 83

3-{1-[(3-Chlorophenyl)sulfonyl]-1H-indazol-5-yl}-N-cyclopropyl-5-fluoro-4-methylbenzamide

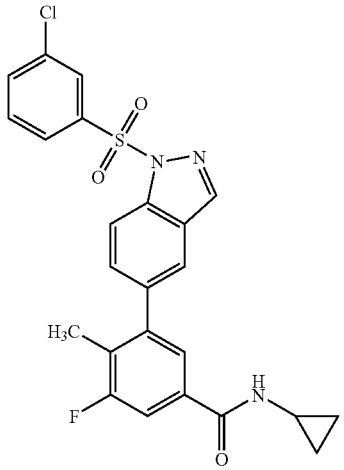

Prepared by General Method C. See Table.

Example 84

N-Cyclopropyl-3-fluoro-5-{1-[(5-fluoro-2-methylphenyl)sulfonyl]-1H-indazol-5-yl}-4-methylbenzamide

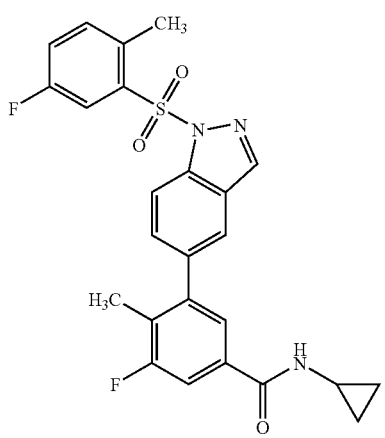

Prepared by General Method C. See Table.

Example 85

N-Cyclopropyl-3-fluoro-5-{1-[(3-fluorophenyl)sulfonyl]-1H-indazol-5-yl}-4-methylbenzamide

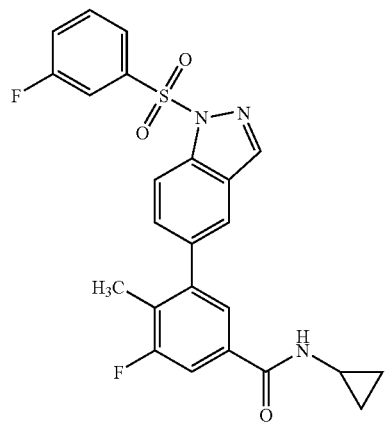

Prepared by General Method C. See Table.

Example 86

N-Cyclopropyl-3-fluoro-4-methyl-5-(1-{[3-(methyloxy)phenyl]sulfonyl}-1H-indazol-5-yl)benzamide

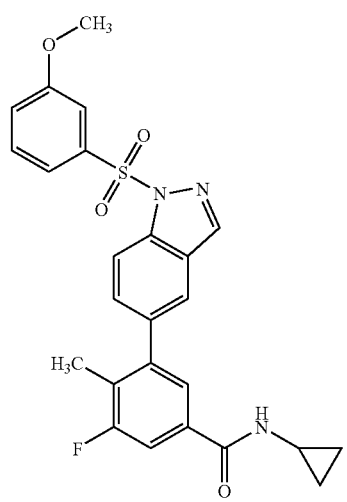

Prepared by General Method C. See Table.

Example 87

N-Cyclopropyl-3-{1-[(3,5-difluorophenyl)sulfonyl]-1H-indazol-5-yl}-5-fluoro-4-methylbenzamide

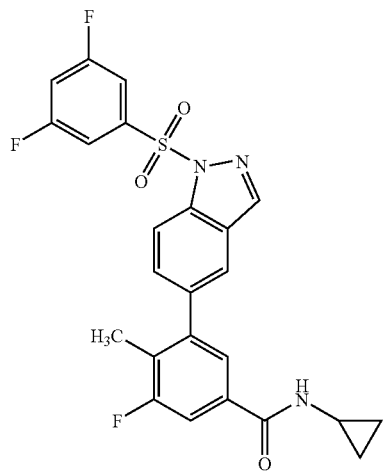

Prepared by General Method C. See Table.

Example 88

N-Cyclopropyl-3-fluoro-4-methyl-5-{1-[(3-methylphenyl)sulfonyl]-1H-indazol-5-yl}benzamide

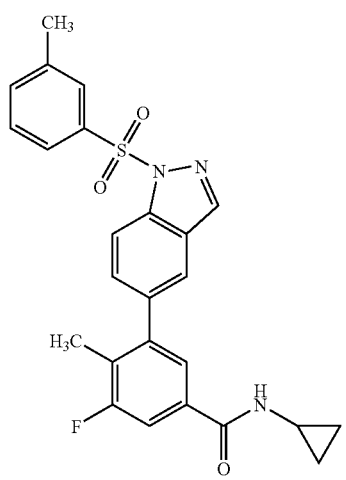

Prepared by General Method C. See Table.

Example 89

N-Cyclopropyl-3-fluoro-4-methyl-5-{1-[(1-methylethyl)sulfonyl]-1H-indazol-5-yl}benzamide

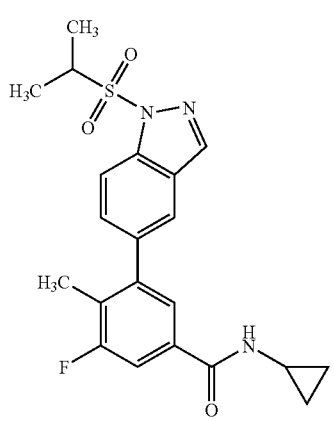

Prepared by General Method C. See Table.

Example 90

N-Cyclopropyl-3-fluoro-4-methyl-5-[1-(propylsulfonyl)-1H-indazol-5-yl]benzamide

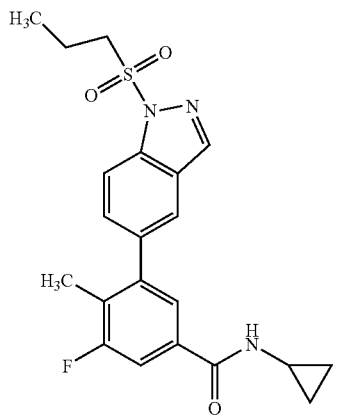

Prepared by General Method C. See Table.

Example 91

N-Cyclopropyl-3-fluoro-4-methyl-5-[1-(methylsulfonyl)-1H-indazol-5-yl]benzamide

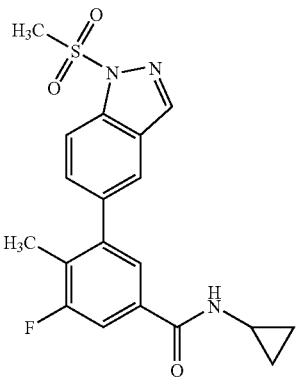

Prepared by General Method C. See Table.

Example 92

3-[1-(Butylsulfonyl)-1H-indazol-5-yl]-N-cyclopropyl-5-fluoro-4-methylbenzamide

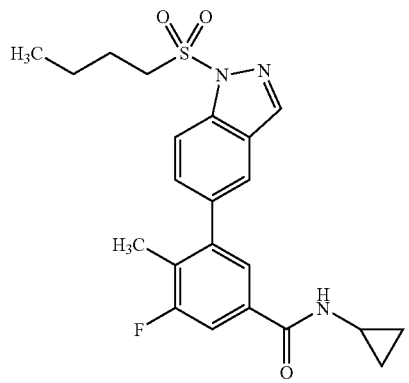

Prepared by General Method C. See Table.

Example 93

N-Cyclopropyl-3-fluoro-4-methyl-5-[1-(octylsulfonyl)-1H-indazol-5-yl]benzamide

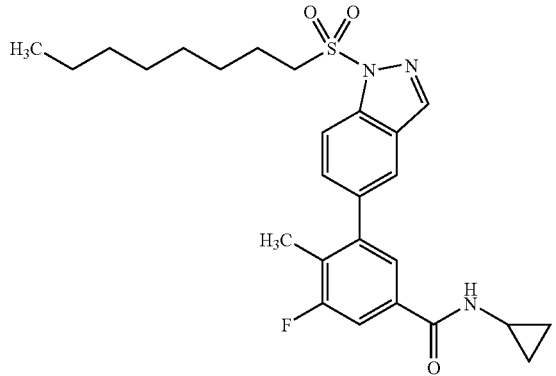

Prepared by General Method C. See Table.

Example 94

N-Cyclopropyl-3-[1-(cyclopropylsulfonyl)-1H-indazol-5-yl]-5-fluoro-4-methylbenzamide

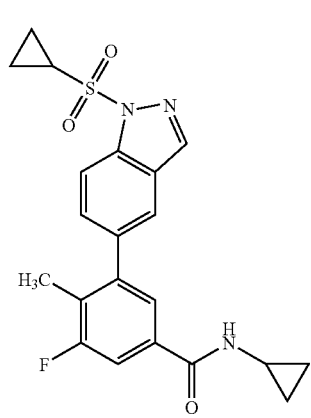

Prepared by General Method C. See Table.

Example 95

3-{1-[(5-Chloro-2-thienyl)sulfonyl]-1H-indazol-5-yl}-N-cyclopropyl-5-fluoro-4-methylbenzamide

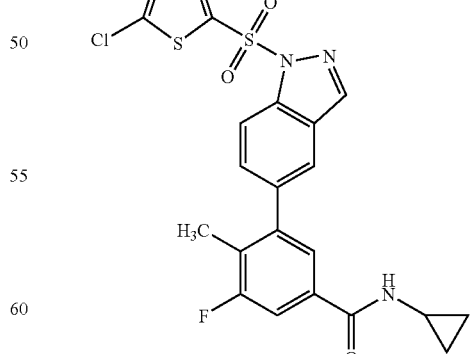

Prepared by General Method C. See Table.

Example 96

N-Cyclopropyl-3-{1-[(3,5-dimethyl-4-isoxazolyl)sulfonyl]-1H-indazol-5-yl}-5-fluoro-4-methylbenzamide

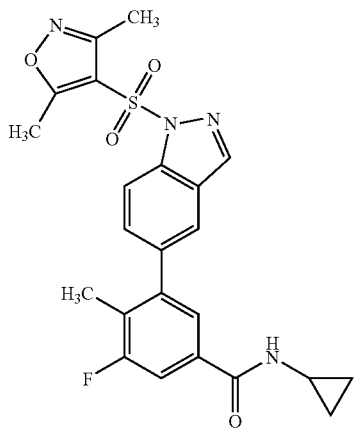

Prepared by General Method C. See Table.

Example 97

N-Cyclopropyl-3-{1-[(1,2-dimethyl-1H-imidazol-4-yl)sulfonyl]-1H-indazol-5-yl}-5-fluoro-4-methylbenzamide

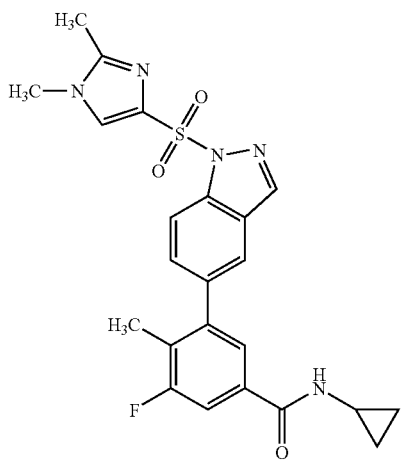

Prepared by General Method C. See Table.

Example 98

N-Cyclopropyl-3-[1-(ethylsulfonyl)-1H-indazol-5-yl]-5-fluoro-4-methylbenzamide

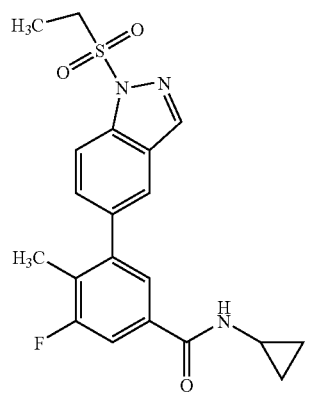

Prepared by General Method C. See Table.

Example 99

3-{1-[(2-Chlorophenyl)sulfonyl]-1H-indazol-5-yl}-N-cyclopropyl-5-fluoro-4-methylbenzamide

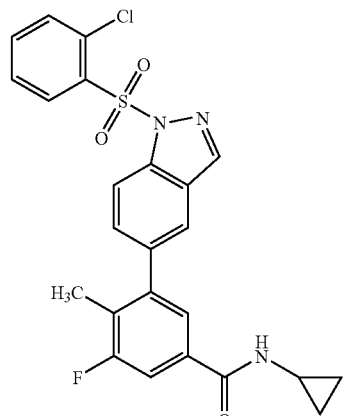

Prepared by General Method C. See Table.

Example 100

N-Cyclopropyl-3-fluoro-4-methyl-5-{1-[(2-methylphenyl)sulfonyl]-1H-indazol-5-yl}benzamide

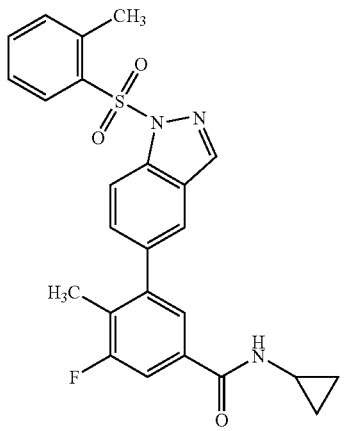

Prepared by General Method C. See Table.

Example 101

N-Cyclopropyl-3-{1-[(4-ethylphenyl)sulfonyl]-1H-indazol-5-yl}-5-fluoro-4-methylbenzamide

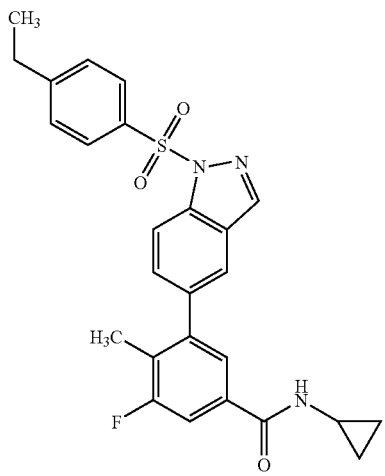

Prepared by General Method C. See Table.

Example 102

N-Cyclopropyl-3-fluoro-4-methyl-5-{1-[(4-propylphenyl)sulfonyl]-1H-indazol-5-yl}benzamide

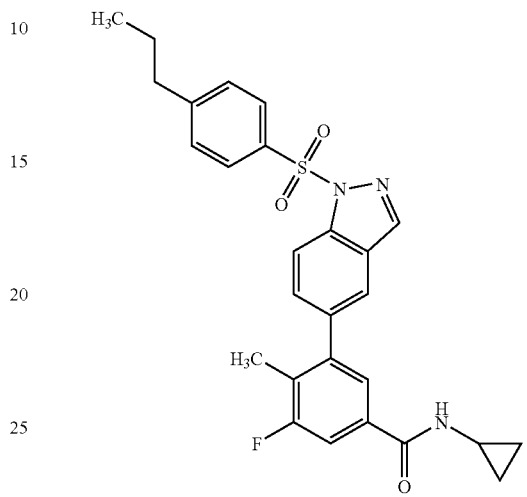

Prepared by General Method C. See Table.

Example 103

N-Cyclopropyl-3-{1-[(3,4-difluorophenyl)sulfonyl]-1H-indazol-5-yl}-5-fluoro-4-methylbenzamide

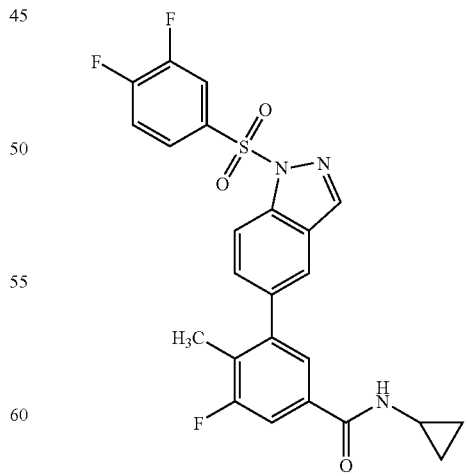

Prepared by General Method C. See Table.

Example 104

3-{1-[(4-Butylphenyl)sulfonyl]-1H-indazol-5-yl}-N-cyclopropyl-5-fluoro-4-methylbenzamide

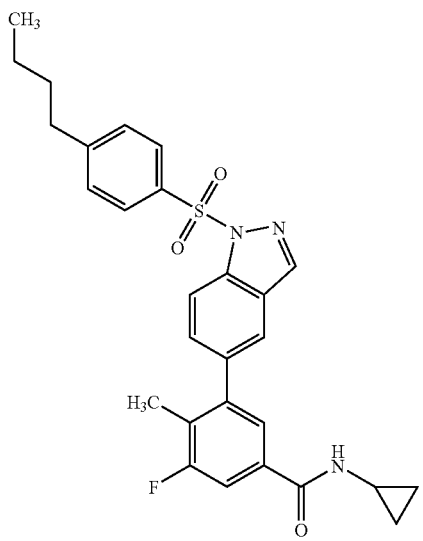

Prepared by General Method C. See Table.

Example 105

N-Cyclopropyl-3-fluoro-4-methyl-5-[1-(phenylsulfonyl)-1H-indazol-5-yl]benzamide

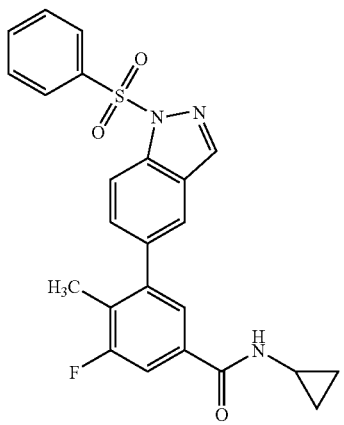

Prepared by General Method C. See Table.

Example 106

N-Cyclopropyl-3-fluoro-4-methyl-5-{1-[(phenylmethyl)sulfonyl]-1H-indazol-5-yl}benzamide

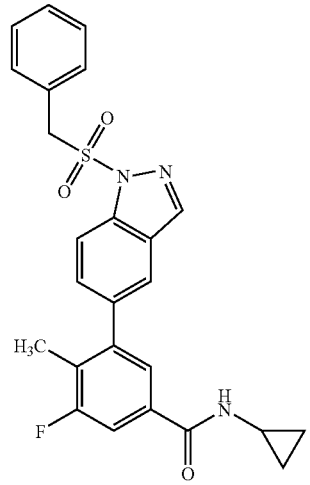

Prepared by General Method C. See Table.

Example 107

N-Cyclopropyl-3-fluoro-4-methyl-5-(1-{[(E)-2-phenylethenyl]sulfonyl}-1H-indazol-5-yl)benzamide

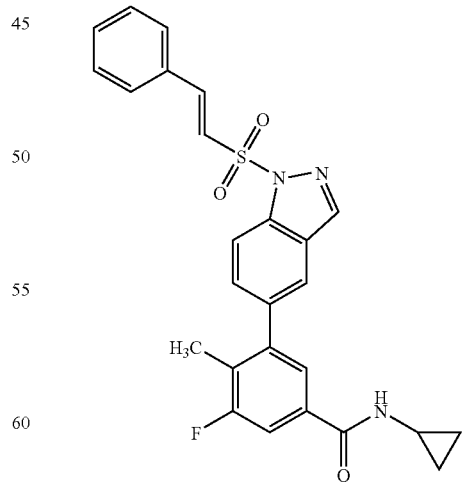

Prepared by General Method C. See Table.

Example 108

N-Cyclopropyl-3-{1-[(2,5-difluorophenyl)sulfonyl]-1H-indazol-5-yl}-5-fluoro-4-methylbenzamide

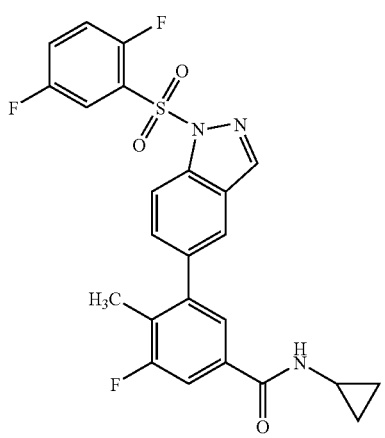

Prepared by General Method C. See Table.

Example 109

N-Cyclopropyl-3-fluoro-5-{1-[(2-fluorophenyl)sulfonyl]-1H-indazol-5-yl}-4-methylbenzamide

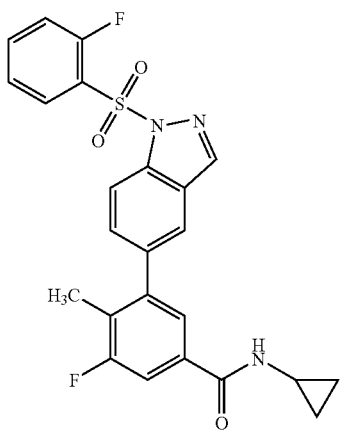

Prepared by General Method C. See Table.

Example 110

3-{1-[(4-Cyanophenyl)sulfonyl]-1H-indazol-5-yl}-N-cyclopropyl-5-fluoro-4-methylbenzamide

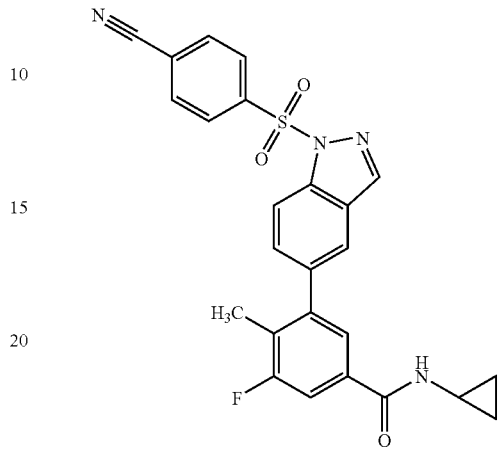

Prepared by General Method C. See Table.

Example 111

N-Cyclopropyl-3-[1-(2,3-dihydro-1-benzofuran-5-ylsulfonyl)-1H-indazol-5-yl]-5-fluoro-4-methylbenzamide

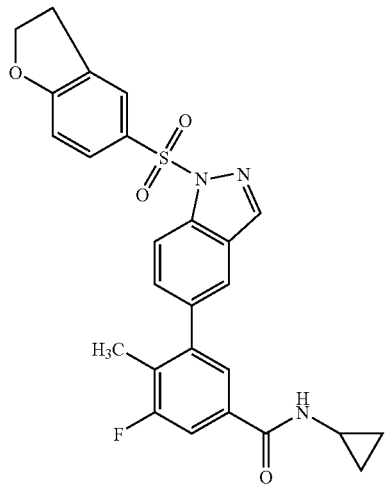

Prepared by General Method C. See Table.

TABLE (Examples 61-111)

| Example No | Indazole Precursor | Sulphonyl Chloride | Rt (min) | MH+ |
|---|---|---|---|---|
| Example 61 | Example 17 | 2-propanesulfonyl chloride[1] | 3.17 | 398 |
| Example 62 | Example 17 | ethanesulfonyl chloride[2] | 3.13 | 384 |
| Example 63 | Example 17 | cyclopropanesulfonyl chloride[3] | 3.18 | 396 |
| Example 64 | Example 17 | methyl 5-(chlorosulfonyl)-2-furancarboxylate[4] | 3.29 | 480 |

TABLE-continued (Examples 61-111)

| Example No | Indazole Precursor | Sulphonyl Chloride | Rt (min) | MH+ |
|---|---|---|---|---|
| Example 65 | Example 17 | 2,1,3-benzoxadiazole-4-sulfonyl chloride[4] | 3.36 | 474 |
| Example 66 | Example 17 | 2-fluorobenzenesulfonyl chloride[1] | 3.38 | 450 |
| Example 67 | Example 17 | 4-methylbenzenesulfonyl chloride[1] | 3.38 | 446 |
| Example 68 | Example 17 | 2-thiophenesulfonyl chloride[1] | 3.33 | 438 |
| Example 69 | Example 17 | 3,5-dimethyl-4-isoxazolesulfonyl chloride[4] | 3.38 | 451 |
| Example 70 | Example 17 | 1-propanesulfonyl chloride[5] | 3.11 | 398 |
| Example 71 | Example 17 | 2-nitrobenzenesulfonyl chloride[1] | 3.4 | 477 |
| Example 72 | Example 17 | 2,2,2-trifluoroethanesulfonyl chloride[1] | 3.11 | 438 |
| Example 73 | Example 17 | 2-cyanobenzenesulfonyl chloride[1] | 3.31 | 457 |
| Example 74 | Example 17 | 1,3,5-trimethyl-1H-pyrazole-4-sulfonyl chloride[4] | 3.18 | 464 |
| Example 75 | Example 17 | 1-methyl-1H-imidazole-4-sulfonyl chloride[4] | 2.88 | 436 |
| Example 76 | Example 60 | 2-thiophenesulfonyl chloride[1] | 3.42 | 456 |
| Example 77 | Example 60 | 3-thiophenesulfonyl chloride[4] | 3.39 | 456 |
| Example 78 | Example 60 | 4-methylbenzenesulfonyl chloride[1] | 3.57 | 464 |
| Example 79 | Example 60 | 4-(methyloxy)benzenesulfonyl chloride[2] | 3.5 | 480 |
| Example 80 | Example 60 | 4-(1-methylethyl)benzenesulfonyl chloride[1] | 3.77 | 492 |
| Example 81 | Example 60 | 4-chlorobenzenesulfonyl chloride[1] | 3.64 | 484 |
| Example 82 | Example 60 | 2,4-difluorobenzenesulfonyl chloride[1] | 3.53 | 486 |
| Example 83 | Example 60 | 3-chlorobenzenesulfonyl chloride[1] | 3.65 | 484 |
| Example 84 | Example 60 | 5-fluoro-2-methylbenzenesulfonyl chloride[1] | 3.65 | 482 |
| Example 85 | Example 60 | 3-fluorobenzenesulfonyl chloride[1] | 3.53 | 468 |
| Example 86 | Example 60 | 3-(methyloxy)benzenesulfonyl chloride[1] | 3.65 | 480 |
| Example 87 | Example 60 | 3,5-difluorobenzenesulfonyl chloride[1] | 3.73 | 486 |
| Example 88 | Example 60 | 3-methylbenzenesulfonyl chloride[2] | 3.71 | 464 |
| Example 89 | Example 60 | 4-(methyloxy)benzenesulfonyl chloride[2] | 3.35 | 416 |
| Example 90 | Example 60 | 1-propanesulfonyl chloride[5] | 3.39 | 416 |
| Example 91 | Example 60 | methanesulfonyl chloride[2] | 3.14 | 388 |
| Example 92 | Example 60 | 1-butanesulfonyl chloride[1] | 3.46 | 430 |
| Example 93 | Example 60 | 1-octanesulfonyl chloride[2] | 3.95 | 486 |
| Example 94 | Example 60 | cyclopropanesulfonyl chloride[3] | 3.25 | 414 |
| Example 95 | Example 60 | 5-chloro-2-thiophenesulfonyl chloride[1] | 3.68 | 490 |
| Example 96 | Example 60 | 3,5-dimethyl-4-isoxazolesulfonyl chloride[2] | 3.48 | 469 |
| Example 97 | Example 60 | 1,2-dimethyl-1H-imidazole-4-sulfonyl chloride[4] | 3 | 468 |
| Example 98 | Example 60 | ethanesulfonyl chloride[2] | 3.21 | 402 |
| Example 99 | Example 60 | 2-chlorobenzenesulfonyl chloride[1] | 3.59 | 484 |
| Example 100 | Example 60 | 2-methylbenzenesulfonyl chloride[1] | 3.59 | 464 |
| Example 101 | Example 60 | 4-ethylbenzenesulfonyl chloride[4] | 3.68 | 478 |
| Example 102 | Example 60 | 4-propylbenzenesulfonyl chloride[2] | 3.81 | 492 |
| Example 103 | Example 60 | 3,4-difluorobenzenesulfonyl chloride[1] | 3.59 | 486 |
| Example 104 | Example 60 | 4-butylbenzenesulfonyl chloride[2] | 3.9 | 506 |
| Example 105 | Example 60 | benzenesulfonyl chloride[1] | 3.45 | 450 |
| Example 106 | Example 60 | phenylmethanesulfonyl chloride[1] | 3.42 | 464 |
| Example 107 | Example 60 | (E)-2-phenylethenesulfonyl chloride[1] | 3.58 | 476 |
| Example 108 | Example 60 | 2,5-difluorobenzenesulfonyl chloride[1] | 3.52 | 486 |
| Example 109 | Example 60 | 2-fluorobenzenesulfonyl chloride[1] | 3.47 | 468 |
| Example 110 | Example 60 | 4-cyanobenzenesulfonyl chloride[2] | 3.42 | 475 |
| Example 111 | Example 60 | 2,3-dihydro-1-benzofuran-5-sulfonyl chloride[4] | 3.47 | 492 |

[1] Purchased from Aldrich.
[2] Purchased from Avocado.
[3] Purchased from Array Biopharma Inc.
[4] Purchased from Maybridge.
[5] Purchased from Pfaltz & Bauer.

Example 112

N-Cyclopropyl-3-fluoro-4-methyl-5-{1-[(4-methylphenyl)sulfonyl]-1H-indol-5-yl}benzamide

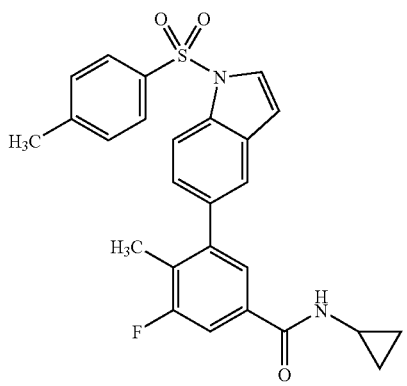

A mixture of 5-bromo-1-[(4-methylphenyl)sulfonyl]-1H-indole (0.035 g) {5-[(cyclopropylamino)carbonyl]-3-fluoro-2-methylphenyl}boronic acid (Intermediate 64) (0.024 g) saturated aqueous sodium hydrogen carbonate (0.5 ml) and tetrakis(triphenylphosphine)palladium(0) (2 mg) in isopropanol (2 ml) was heated in a microwave at 150° for 10 min. The solid was removed by filtration and the residue was purified by preparative Hplc to give the title compound (0.013 g).

LCMS: Rt 3.71 min, MH+ 463.

Example 113

N-Cyclopropyl-3-fluoro-4-methyl-5-[1-(phenylsulfonyl)-1H-indol-5-yl]benzamide

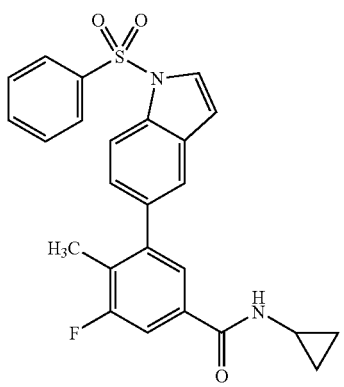

The procedure for Example 112 was followed using 5-bromo-1-(phenylsulfonyl)-1H-indole (0.033 g) in place of 5-bromo-1-[(4-methylphenyl)sulfonyl]-1H-indole to give the title compound (0.009 g).

LCMS: Rt 3.61 min, MH+ 449.

Example 114

N-Cyclopropyl-3-[1-(cyclopropylmethyl)-1H-indazol-5-yl]-4-methylbenzamide

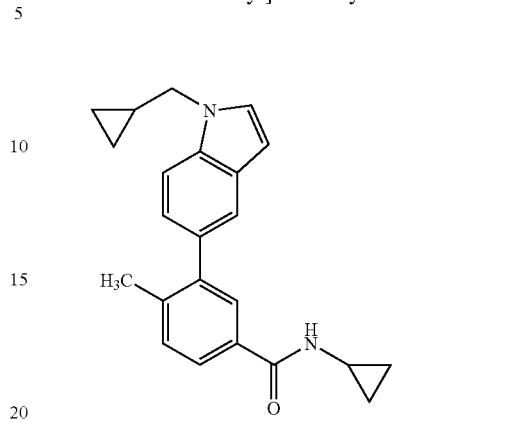

A solution of N-cyclopropyl-3-(1H-indazol-5-yl)-4-methylbenzamide (Example 17) (0.10 g) in dry DMF (3 ml) was treated with sodium hydride (60% oil dispersion, 0.017 g) under nitrogen. After 5 min cyclopropylmethyl bromide (0.04 ml) was added and the yellow solution was stirred at room temp. for 18 h. Methanol (2 drops) was added and the solvent was evaporated. The residue was purified by column chromatography on silica eluting with cyclohexane:ethyl acetate (2:1 to 1:1) to give the title compound (0.05 g).

LCMS: Rt 3.21 min, MH+ 346.

Example 115

1,1-Dimethylethyl 4-(5-{5-[(cyclopropylamino)carbonyl]-2-methylphenyl}-1H-indazol-1-yl)-1-piperidinecarboxylate

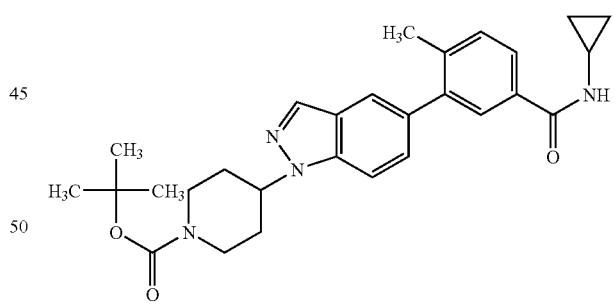

A solution of N-cyclopropyl-3-(1H-indazol-5-yl)-4-methylbenzamide (Example 17) (0.07 g) in dry DMF (3 ml) was treated with sodium hydride (60% oil dispersion, 0.014 g) under nitrogen. After 5 min 1,1-dimethylethyl 4-[(methylsulfonyl)oxy]-1-piperidinecarboxylate (0.08 g) was added and the mixture was stirred at room temp. for 18 h. 0.88 Ammonia (1 ml) was added and the mixture was concentrated under vacuum. The residue was purified by column chromatography on silica eluting with cyclohexane:ethyl acetate (1:1) followed by reverse phase preparative Hplc to give the title compound (0.005 g).

LCMS: Rt 3.55 min, MH+ 475.

Example 116

N-Cyclopropyl-4-methyl-3-[1-(4-piperidinyl)-1H-indazol-5-yl]benzamide hydrochloride

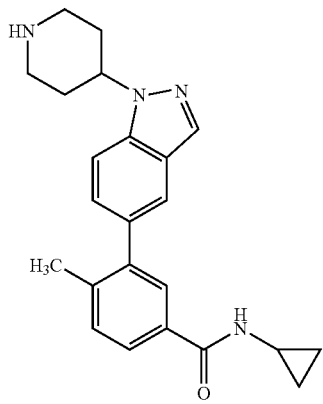

A suspension of 1,1-dimethylethyl 4-(5-{5-[(cyclopropylamino)carbonyl]-2-methylphenyl}-1H-indazol-1-yl)-1-piperidinecarboxylate Example 115) (0.01 g) in a solution of hydrogen chloride in dioxan (4M, 1 ml) was treated with methanol (0.25 ml) to give a solution which was stirred at room temp. for 18 h. The solvent was evaporated and the residue was dried under vacuum to give the title compound (0.009 g).
LCMS: Rt 2.40 min, MH+ 375.

Example 117

Methyl (5-{5-[(cyclopropylamino)carbonyl]-2-methylphenyl}-1H-indazol-1-yl)acetate

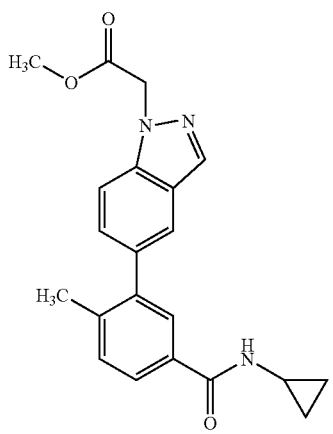

A solution of N-cyclopropyl-3-(1H-indazol-5-yl)-4-methylbenzamide (Example 17) (0.65 g) in dry DMF (26 ml) was treated with sodium hydride (60% oil dispersion, 0.134 g) under nitrogen. After 5 min methyl chloroacetate (0.29 g) was added and the mixture was stirred for 2 h. Aqueous ammonia (2M, 10 ml) was added and the solvent was removed under vacuum. The residue was purified by column chromatography on silica eluting with cyclohexane:ethyl acetate (2:1 to 1:1) to give the title compound (0.56 g).
LCMS: Rt 2.95 min, MH+ 364.

Example 118

N-cyclopropyl-3-(1H-indazol-6-yl)-4-methylbenzamide

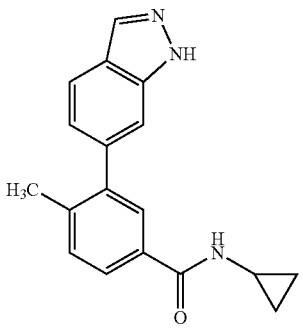

A mixture of 1-acetyl-6-bromo-1H-indazole (Intermediate 65) (0.50 g) N-cyclopropyl-4-methyl-3-(4,4,5,5-tetramethyl-1,3,2-dioxaborolan-2-yl)benzamide (Intermediate 5) (0.59 g) aqueous sodium carbonate (1M, 2.35 ml) and PdCl$_2$dppf (0.237 g) in 1,2-dimethoxyethane (30 ml) was stirred at reflux under nitrogen for 16 h. More sodium carbonate (2.3 ml) and catalyst (120 mg) were added and reflux was continued for a further 4 h. Conc. hydrochloric acid (1 ml) was added and the mixture was heated for a further 1 h. The mixture was absorbed onto silica then purified by column chromatography on silica eluting with cyclohexane:ethyl acetate (2:1 to 1:4) to give the title compound (0.25 g).
LCMS: Rt 2.88 min, MH+ 292.

Example 119

N-Cyclopropyl-3-{3-[(4-fluorophenyl)sulfonyl]-1H-indazol-6-yl}-4-methylbenzamide

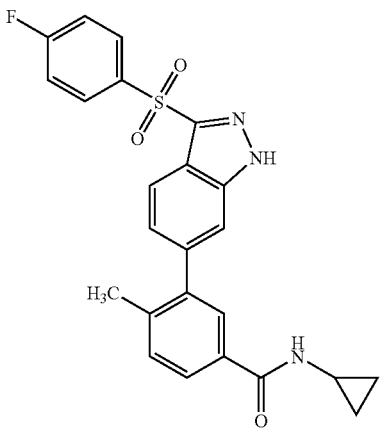

To a solution of N-cyclopropyl-3-[3-[(4-fluorophenyl)sulfonyl]-1-({[2-(trimethylsilyl)ethyl]oxy}methyl)-1H-indazol-6-yl]-4-methylbenzamide (Intermediate 71) (0.05 g) in methanol (1.5 ml) was added conc hydrochloric acid (0.75 ml). The solution was heated at reflux for 15 h then left at room temp. for 18 h. The solution was concentrated under vacuum then purified on a Varian Bond-Elut SPE cartridge (silica, 5 g) eluting with cyclohexane:ethyl acetate (1:1) to give the title compound (0.01 g).
LCMS: Rt 3.32 min, MH+ 450.

Example 120

N-Cyclopropyl-3-fluoro-4-methyl-5-[3-(methylsulfonyl)-1H-indazol-6-yl]benzamide

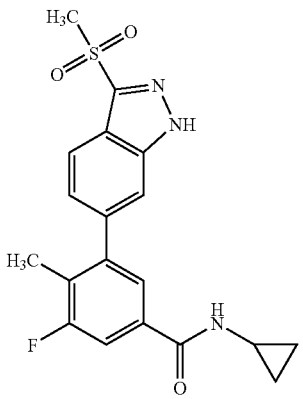

Conc. hydrochloric acid ((0.5 ml) was added to a solution of N-cyclopropyl-3-fluoro-4-methyl-5-[3-(methylsulfonyl)-1-({[2-(trimethylsilyl)ethyl]oxy}methyl)-1H-indazol-6-yl]benzamide (Intermediate 77) (0.15 g) then stirred at reflux for 12 h. The solvent was evaporated and the residue was purified by column chromatography on silica, eluting with cyclohexane:ethyl acetate (1:1 to 1:2) to give the title compound (0.085 g).
LCMS: Rt 2.91 min, MH+ 388.

Example 121

N-Cyclopropyl-3-fluoro-4-methyl-5-(3-methyl-1H-indazol-5-yl)benzamide

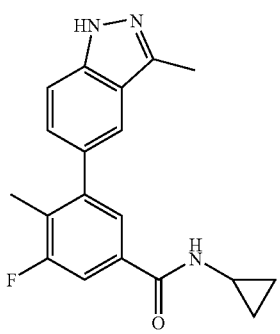

A mixture of 1-acetyl-5-bromo-3-methyl-1H-indazole (0.100 g) {5-[(cyclopropylamino)carbonyl]-3-fluoro-2-methylphenyl}boronic acid (Intermediate 64) (0.094 g) saturated aqueous sodium hydrogen carbonate (2 ml) and tetrakis(triphenylphosphine)palladium(0) (9 mg) in isopropanol (6 ml) was heated in a microwave at 150° for 10 min. The solvent was evaporated and the residue was purified on a Varian Bond-Elut SPE cartridge (silica log) eluting with cyclohexane:ethyl acetate (1:1) to give the title compound (0.073 g).
LCMS: Rt 3.02 min, MH+ 324.

Example 122

N-Cyclopropyl-3-fluoro-4-methyl-5-[3-methyl-1-(2-thienylsulfonyl)-1H-indazol-5-yl]benzamide

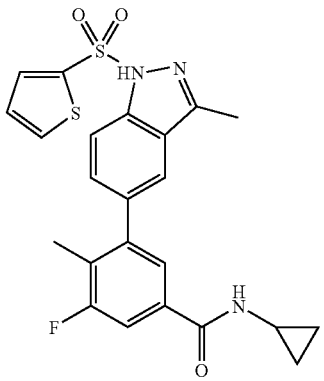

Sodium hydride (60% oil dispersion, 0.008 g) was added to a stirred solution of N-cyclopropyl-3-fluoro-4-methyl-5-(3-methyl-1H-indazol-5-yl)benzamide (Example 121) (0.033 g) in dry DMF (1.5 ml) under nitrogen. After 5 min a solution of 2-thiophenesulphonyl chloride (0.038 g) in DMF (0.75 ml) was added and stirring was continued for a further 2 h. Water (1 ml) and chloroform (10 ml) were added, the mixture was passed through a hydrophobic filter and the solvent was evaporated. The residue was purified by preparative Hplc to give the title compound as a clear glass (0.024 g).
LCMS: Rt 3.44 min, MH+ 470.

Example 123

Methyl (5-{5-[(cyclopropylamino)carbonyl]-3-fluoro-2-methylphenyl}-1H-indazol-1-yl)acetate

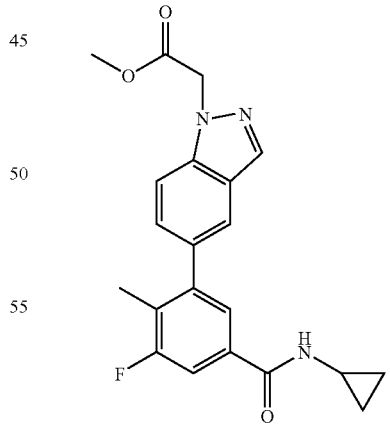

A solution of N-cyclopropyl-3-fluoro-5-(1H-indazol-5-yl)-4-methylbenzamide (example 60) (0.35 g) in dry DMF (5 ml) was treated with sodium hydride (60% oil dispersion, 0.08 g) at room temp under nitrogen then stirred for 20 min. A solution of methyl bromoacetate (0.2 ml) in dry DMF (0.5 ml) was added and stirring was continued for 1 h. Water (30 ml) was added and the mixture was extracted with ethyl acetate (×2). The organic extracts were washed with water (×3) and brine, dried (Na$_2$SO$_4$) and concentrated under vacuum. The residue was purified using a Varian Bond-Elut SPE cartridge (silica, 10 g) eluting with cyclohexane:ethyl acetate (4:1 to 1:1) to give the title compound as a yellow foam (0.26 g).

LCMS: Rt 3.03 min, MH+ 382.

Example 124

N-Cyclopropyl-4-methyl-3-{1-[2-({[4-(methyloxy) phenyl]methyl}amino)-2-oxoethyl]-1H-indazol-5-yl}benzamide

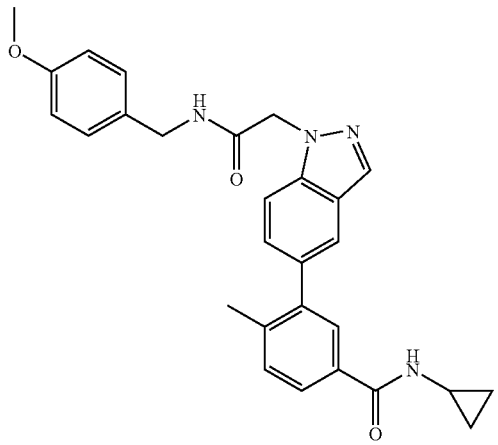

Example 124 was prepared by General Method D using methyl (5-{5-[(cyclopropylamino)carbonyl]-2-methylphenyl}-1H-indazol-1-yl)acetate (Example 117) and 4-methoxybenzylamine to give the title compound (0.011 g).

LCMS: Rt 2.99 min, MH+ 469.

Example 125

N-Cyclopropyl-4-methyl-3-(1-{2-oxo-2-[(phenylmethyl)amino]ethyl}-1H-indazol-5-yl)benzamide

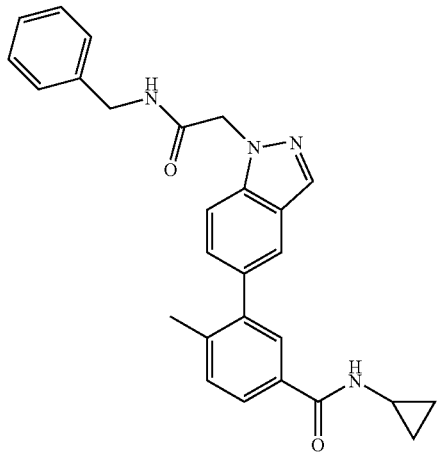

Example 125 was prepared by General Method D using methyl (5-{5-[(cyclopropylamino)carbonyl]-2-methylphenyl}-1H-indazol-1-yl)acetate (Example 117) and benzylamine to give the title compound (0.002 g), LCMS: Rt 3.00 min, MH+ 439.

Example 126

N-Cyclopropyl-4-methyl-3-[1-(2-{[(4-methylphenyl) methyl]amino}-2-oxoethyl)-1H-indazol-5-yl]benzamide

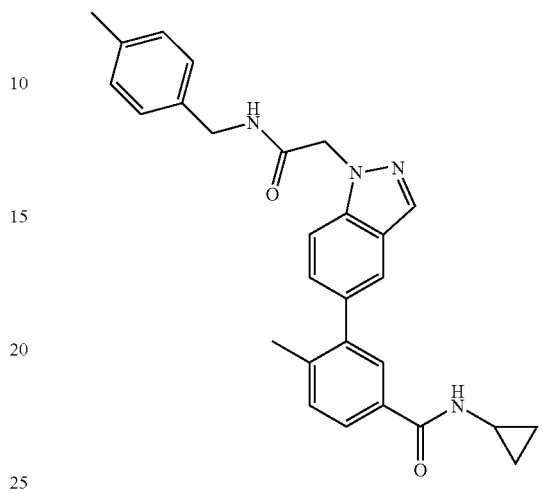

Example 126 was prepared by General Method D using methyl (5-{5-[(cyclopropylamino)carbonyl]-2-methylphenyl}-1H-indazol-1-yl)acetate Example 117) and 4-methylbenzylamine to give the title compound (0.010 g)

LCMS: Rt 3.11 min, MH+ 453.

Example 127

N-Cyclopropyl-4-methyl-3-(1-{2-[({4-[(methylamino)carbonyl]phenyl}methyl)amino]-2-oxoethyl}-1H-indazol-5-yl)benzamide

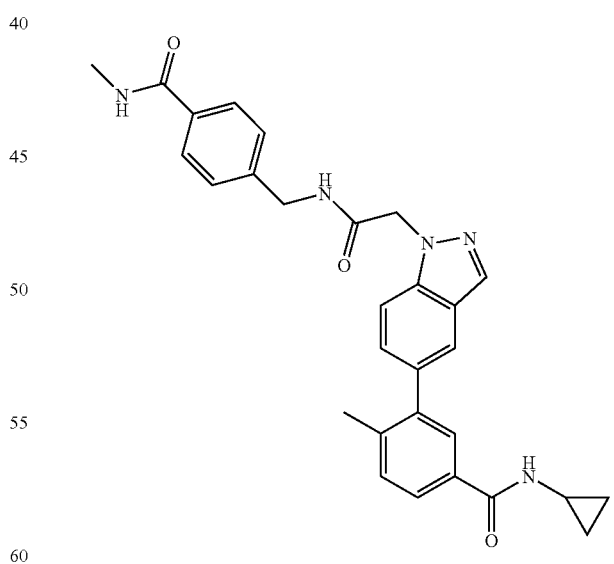

Example 127 was prepared by General Method D using methyl (5-{5-[(cyclopropylamino)carbonyl]-2-methylphenyl}-1H-indazol-1-yl)acetate (Example 117) and 4-(aminomethyl)-N-methylbenzamide to give the title compound (0.005 g).

LCMS: Rt 2.68 min, MH+ 496.

Example 128

N-Cyclopropyl-4-methyl-3-{1-[2-oxo-2-(propylamino)ethyl]-1H-indazol-5-yl}benzamide

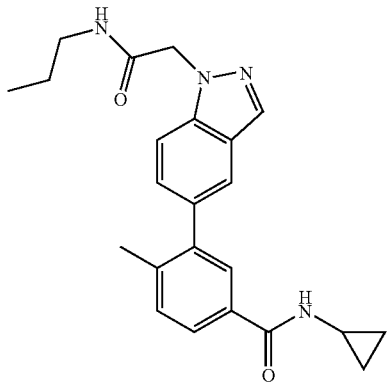

Example 128 was prepared by General Method D using methyl (5-{5-[(cyclopropylamino)carbonyl]-2-methylphenyl}-1H-indazol-1-yl)acetate (Example 117) and 1-propylamine to give the title compound (0.011 g).

LCMS: Rt 2.81 min, MH+ 391.

Example 129

N-Cyclopropyl-3-(1-{2-[(cyclopropylmethyl)amino]-2-oxoethyl}-1H-indazol-5-yl)-4-methylbenzamide

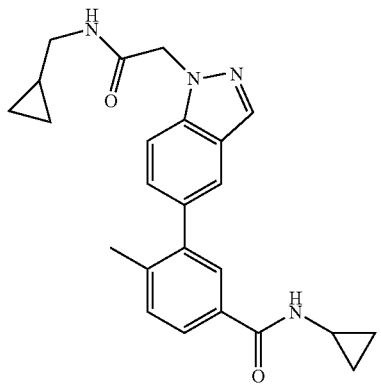

Example 129 was prepared by General Method D using methyl (5-{5-[(cyclopropylamino)carbonyl]-2-methylphenyl}-1H-indazol-1-yl)acetate (Example 117) and 1-cyclopropylmethanamine to give the title compound (0.015 g).

LCMS: Rt 2.86 min, MH+ 403.

Example 130

N-Cyclopropyl-3-(1-{2-[(2,2-dimethylpropyl)amino]-2-oxoethyl}-1H-indazol-5-yl)-4-methylbenzamide

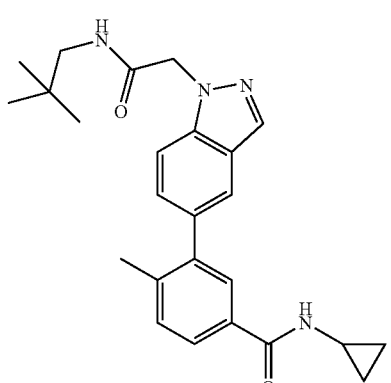

Example 130 was prepared by General Method D using methyl (5-{5-[(cyclopropylamino)carbonyl]-2-methylphenyl}-1H-indazol-1-yl)acetate (Example 117) and 2,2-dimethyl-1-propanamine to give the title compound (0.015 g).

LCMS: Rt 3.06 min, MH+ 419.

Example 131

N-Cyclopropyl-4-methyl-3-{1-[2-(4-morpholinyl)-2-oxoethyl]-1H-indazol-5-yl}benzamide

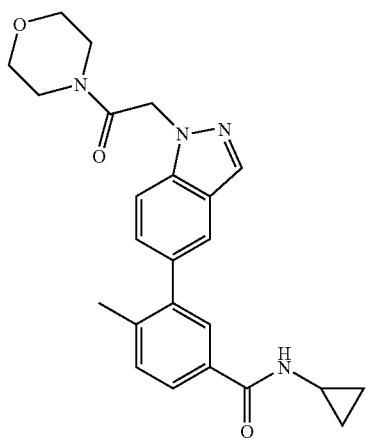

Example 131 was prepared by General Method D using methyl (5-{5-[(cyclopropylamino)carbonyl]-2-methylphenyl}-H-indazol-1-yl)acetate Example 117) and morpholine to give the title compound (0.002 g).

LCMS: Rt 2.66 min, MH+ 419.

Example 132

N-Cyclopropyl-3-fluoro-4-methyl-5-(1-{2-oxo-2-[(phenylmethyl)amino]ethyl}1H-indazol-5-yl)benzamide

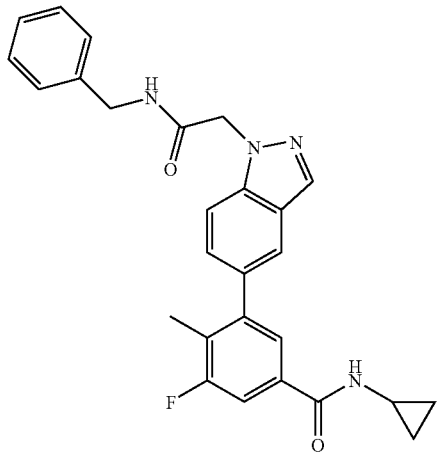

Example 132 was prepared by General Method D using methyl (5-{5-[(cyclopropylamino)carbonyl]-3-fluoro-2-methylphenyl}-1H-indazol-1-yl)acetate (Example 123) and benzylamine to give the title compound (0.008 g).

LCMS: Rt 3.17 min, MH+ 457.

Example 133

N-Cyclopropyl-3-fluoro-4-methyl-5-[1-(2-{[(4-methylphenyl)methyl]amino}-2-oxoethyl)-1H-indazol-5-yl]benzamide

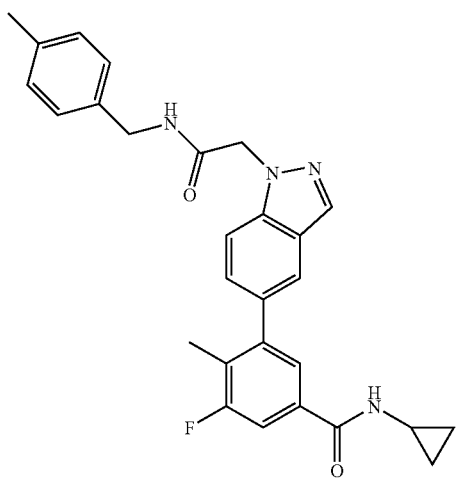

Example 133 was prepared by General Method D using methyl (5-{5-[(cyclopropylamino)carbonyl]-3-fluoro-2-methylphenyl}-1H-indazol-1-yl)acetate (Example 123) and 4-methylbenzylamine to give the title compound (0.011 g).

LCMS: Rt 3.28 min, MH+ 471.

Example 134

N-Cyclopropyl-3-fluoro-4-methyl-5-{1-[2-({[4-(methyloxy)phenyl]methyl}amino)-2-oxoethyl]-1H-indazol-5-yl}benzamide

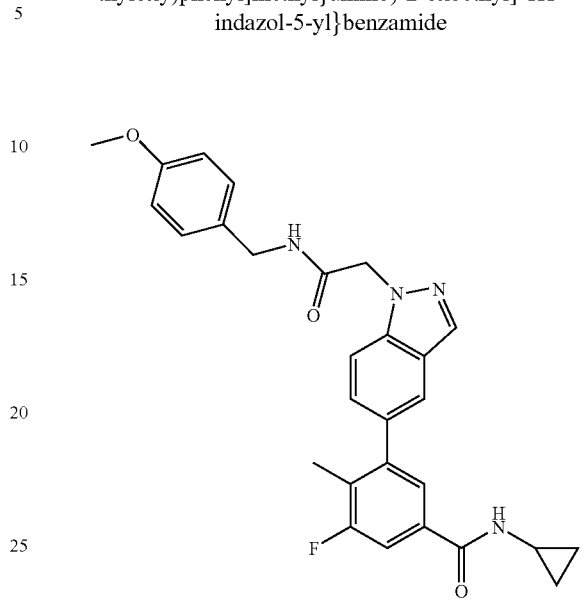

Example 134 was prepared by General Method D using methyl (5-{5-[(cyclopropylamino)carbonyl]-3-fluoro-2-methylphenyl}-1H-indazol-1-yl)acetate (Example 123) and 4-methoxybenzylamine to give the title compound (0.012 g).

LCMS: Rt 3.15 min, MH+ 487.

Example 135

N-Cyclopropyl-3-fluoro-4-methyl-5-(1-{2-[({4-[(methylamino)carbonyl]phenyl}methyl)amino]-2-oxoethyl}-1H-indazol-5-yl)benzamide

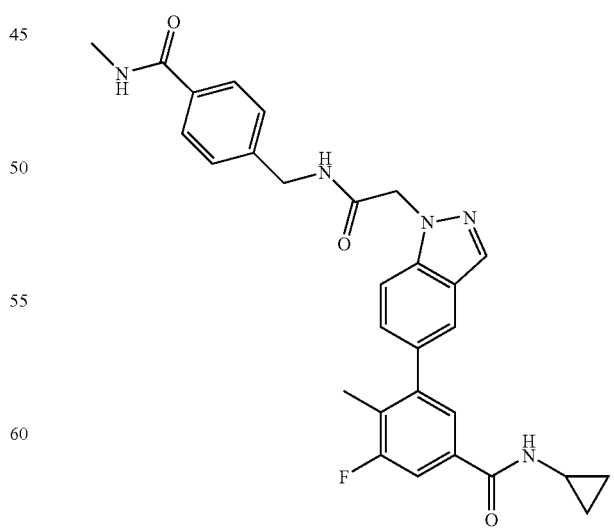

Example 135 was prepared by General Method D using methyl (5-{5-[(cyclopropylamino)carbonyl]-3-fluoro-2-methylphenyl}-H-indazol-1-yl)acetate (Example 123) and 4-(aminomethyl)-N-methylbenzamide to give the title compound (0.005 g).

LCMS: Rt 2.80 min, MH+ 514.

Example 136

N-Cyclopropyl-3-fluoro-4-methyl-5-{1-[2-oxo-2-(propylamino)ethyl]-1H-indazol-5-yl}benzamide

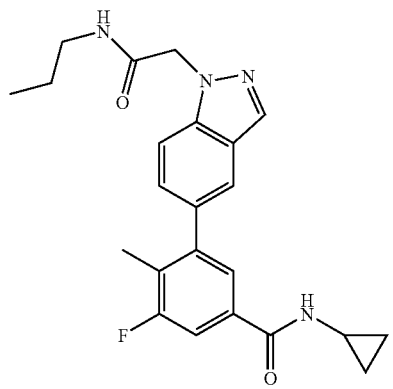

Example 136 was prepared by General Method D using methyl (5-{5-[(cyclopropylamino)carbonyl]-3-fluoro-2-methylphenyl}-1H-indazol-1-yl)acetate (Example 123) and 1-propylamine to give the title compound (0.005 g).

LCMS: Rt 2.92 min, MH+ 409.

Example 137

N-cyclopropyl-3-(1-{2-[(cyclopropylmethyl)amino]-2-oxoethyl}-1H-indazol-5-yl)-5-fluoro-4-methylbenzamide

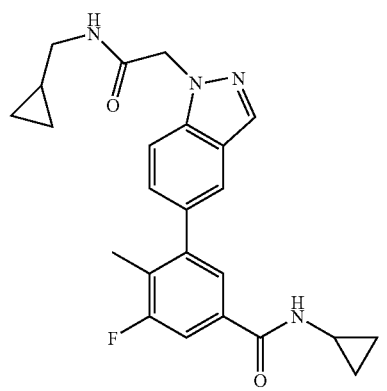

Example 137 was prepared by General Method D using methyl (5-{5-[(cyclopropylamino)carbonyl]-3-fluoro-2-methylphenyl}-1H-indazol-1-yl)acetate (Example 123) and 1-cyclopropylmethanamine to give the title compound (0.008 g).

LCMS: Rt 2.96 min, MH+ 421.

Example 138

N-Cyclopropyl-3-fluoro-4-methyl-5-{1-[2-(4-morpholinyl)-2-oxoethyl]-1H-indazol-5-yl}benzamide

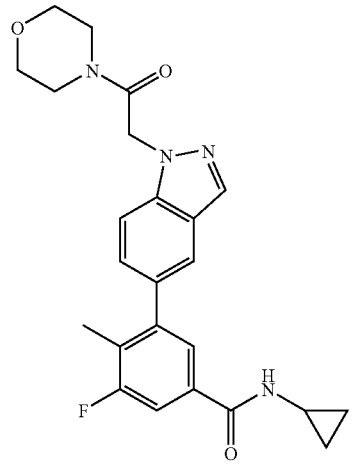

Example 138 was prepared by General Method D using methyl (5-{5-[(cyclopropylamino)carbonyl]-3-fluoro-2-methylphenyl}-1H-indazol-1-yl)acetate (Example 123) and morpholine to give the title compound (0.001 g).

LCMS: Rt 2.76 min, MH+ 437.

Example 139

N-Cyclopropyl-4-methyl-3-(1-{2-[1-methylethyl)amino]-2-oxoethyl}-1H-indazol-5-yl)benzamide

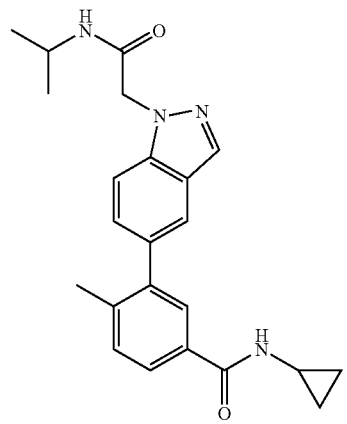

Example 139 was prepared by General Method D using methyl (5-{5-[(cyclopropylamino)carbonyl]-2-methylphenyl}-1H-indazol-1-yl)acetate (Example 117) and 2-propylamine to give the title compound (0.002 g).

LCMS: Rt 2.82 min, MH+ 391.

Example 140

N-Cyclopropyl-3-(1-{2-[(2,2-dimethylpropyl)amino]-2-oxoethyl}-1H-indazol-5-yl)-5-fluoro-4-methylbenzamide

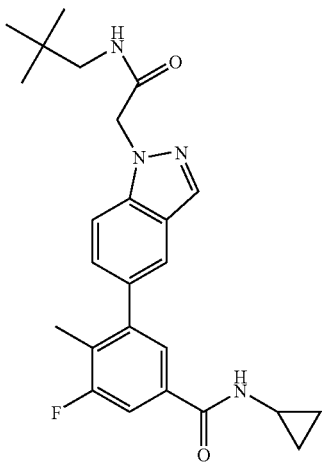

Example 140 was prepared by General Method D using methyl (5-{5-[(cyclopropylamino)carbonyl]-3-fluoro-2-methylphenyl}-1H-indazol-1-yl)acetate (Example 123) and 2,2-dimethyl-1-propanamine to give the title compound (0.008 g).

LCMS: Rt 3.21 min, MH+ 437.

Example 141

N-Cyclopropyl-3-{2-[(cyclopropylcarbonyl)amino]-1,3-benzothiazol-6-yl}-4-methylbenzamide

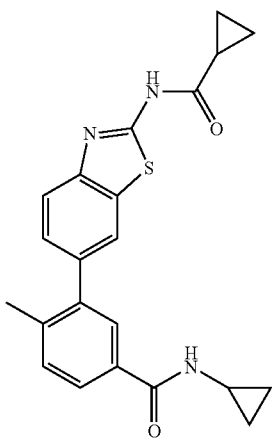

Example 141 was made by General Method A using N-(6-bromo-1,3-benzothiazol-2-yl)cyclopropanecarboxamide and N-cyclopropyl-4-methyl-3-(4,4,5,5-tetramethyl-1,3,2-dioxaborolan-2-yl)benzamide (Intermediate 5) to give the title compound (0.4 mg).

LCMS: Rt 2.67 min, MH+ 392.

| Abbreviations | |
|---|---|
| $Ac_2O$ | Acetic anhydride |
| $^tBuONO$ | t-Butyl nitrite |
| CDI | Carbonyldiimidazole |
| DBU | 1,8-Diazabicyclo[5.4.0]undec-7-ene |
| DIPEA | N,N-Diisopropylethylamine |
| DME | 1,2-Dimethoxyethane |
| DMF | Dimethylformamide |
| DMSO | Dimethylsulphoxide |
| $Et_2O$ | Ether |
| EtOH | Ethanol |
| Hal | Halogen |
| HATU | O-(7-Azabenzotriazol-1-yl)-N,N,N',N'-tetramethyluronium hexafluorophosphate |
| HOBT | 1-Hydroxybenzotriazole |
| KOAc | Potassium Acetate |
| MeCN | Acetonitrile |
| MeOH | Methanol |
| Ms | Mesyl |
| $NaO^tBu$ | Sodium tert-butoxide |
| NaOEt | Sodium Ethoxide |
| NCS | N-Chlorosuccinimide |
| $PdCl_2dppf$ | [1,1'-bis(diphenylphosphino)ferrocene]dichloropalladium (II) complex with dichloromethane (1:1) |
| Rt | Retention Time |
| SPE | Solid phase extraction |
| THF | Tetrahydrofuran |

BIOLOGICAL EXAMPLES

The activity of compounds of formula (I) as p38 inhibitors may be determined by the following in vitro assays:

Fluorescence Anisotropy Kinase Binding Assay

The kinase enzyme, fluorescent ligand and a variable concentration of test compound are incubated together to reach thermodynamic equilibrium under conditions such that in the absence of test compound the fluorescent ligand is significantly (>50%) enzyme bound and in the presence of a sufficient concentration (>10× $K_i$) of a potent inhibitor the anisotropy of the unbound fluorescent ligand is measurably different from the bound value.

The concentration of kinase enzyme should preferably be $\geq 1\times K_f$. The concentration of fluorescent ligand required will depend on the instrumentation used, and the fluorescent and physicochemical properties. The concentration used must be lower than the concentration of kinase enzyme, and preferably less than half the kinase enzyme concentration. A typical protocol is:

All components dissolved in Buffer of final composition 62.5 mM HEPES, pH 7.5, 1.25 mM CHAPS, 1.25 mM DTT, 12.5 mM $MgCl_2$ 3.3% DMSO.

p38 Enzyme concentration: 12 nM
Fluorescent ligand concentration: 5 nM
Test compound concentration: 0.1 nM-100 uM Components incubated in 30 ul final volume in NUNC 384 well black microtitre plate until equilibrium reached (5-30 mins)

Fluorescence anisotropy read in LJL Acquest.

Definitions:

$K_i$=dissociation constant for inhibitor binding
$K_f$=dissociation constant for fluorescent ligand binding
The fluorescent ligand is the following compound:

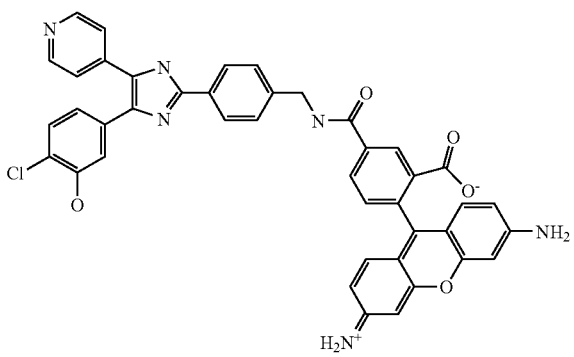

which is derived from 5-[2-(4-aminomethylphenyl)-5-pyridinyl-4-yl-1H-imidazol-4-yl]-2-chlorophenol and rhodamine green.

Results

The compounds described in the Examples were tested as described above and had $IC_{50}$ values of <10 µM.

The invention claimed is:
1. A compound of formula (I):

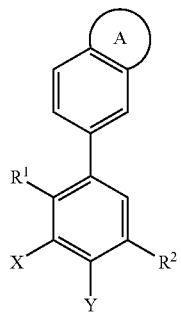

(I)

wherein
A is a fused 5-membered heteroaryl ring selected from

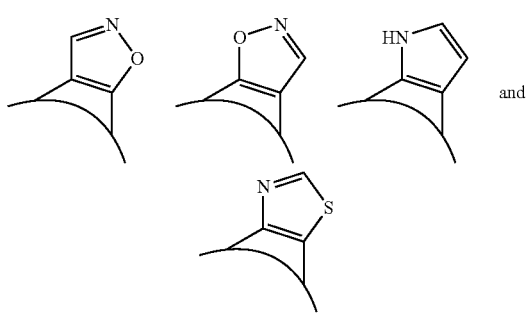

and which ring is optionally substituted by up to two substituents independently selected from $C_{1-6}$alkyl, —$(CH_2)_m$—$C_{3-7}$cycloalkyl, halogen, cyano, trifluoromethyl, —$(CH_2)_m OR^3$, —$(CH_2)_m CO_2 R^3$, —$(CH_2)_m NR^3 R^4$, —$(CH_2)_m CONR^3 R^4$, —$(CH_2)_m NHCOR^3$, —$(CH_2)_m SO_2 NR^3 R^4$, —$(CH_2)_m NHSO_2 R^3$, —$(CH_2)_m SO_2 (CH_2)_n R^5$, a 5- or 6-membered heterocyclyl ring containing nitrogen optionally substituted by $C_{1-2}$alkyl or —$(CH_2)_m CO_2 R^3$, and a 5-membered heteroaryl ring optionally substituted by $C_{1-2}$alkyl;

$R^1$ is selected from methyl and chloro;

$R^2$ is selected from —NH—CO—$R^6$ and —CO—NH—$(CH_2)_q$—$R^7$;

$R^3$ is selected from hydrogen, $C_{1-6}$alkyl optionally substituted by up to two OH groups, —$(CH_2)_m$—$C_{3-7}$cycloalkyl, —$(CH_2)_m$phenyl optionally substituted by $R^8$ and/or $R^9$ and —$(CH_2)_m$heteroaryl optionally substituted by $R^8$ and/or $R^9$;

$R^4$ is selected from hydrogen and $C_{1-6}$alkyl, or $R^3$ and $R^4$, together with the nitrogen atom to which they are bound, form a 5- or 6-membered heterocyclic ring optionally containing one additional heteroatom selected from oxygen, sulfur and N—$R^{10}$;

$R^5$ is selected from $C_{1-6}$alkyl optionally substituted by up to three halogen atoms, $C_{2-6}$alkenyl optionally substituted by phenyl, $C_{3-7}$cycloalkyl, heteroaryl optionally substituted by up to three $R^8$ and/or $R^9$ groups, and phenyl optionally substituted by $R^8$ and/or $R^9$;

$R^6$ is selected from hydrogen, $C_{1-6}$alkyl, —$(CH_2)_q$—$C_{3-7}$cycloalkyl, trifluoromethyl, —$(CH_2)_r$heteroaryl optionally substituted by $R^{11}$ and/or $R^{12}$, and —$(CH_2)_r$phenyl optionally substituted by $R^{11}$ and/or $R^{12}$;

$R^7$ is selected from hydrogen, $C_{1-6}$alkyl, $C_{3-7}$cycloalkyl, —$CONHR^{13}$, phenyl optionally substituted by $R^{11}$ and/or $R^{12}$, and heteroaryl optionally substituted by $R^{11}$ and/or $R^{12}$;

$R^8$ and $R^9$ are each independently selected from halogen, cyano, trifluoromethyl, nitro, $C_{1-6}$alkyl, $C_{1-6}$alkoxy, —$CONR^{13}R^{14}$, —$COR^{15}$, —$CO_2 R^{15}$, and heteroaryl, or $R^8$ and $R^9$ are linked to form a fused 5-membered heterocyclyl ring containing one heteroatom selected from oxygen, sulphur and N—$R^{10}$, or a fused heteroaryl ring;

$R^{10}$ is selected from hydrogen and methyl;

$R^{11}$ is selected from $C_{1-6}$alkyl, $C_{1-6}$alkoxy, —$(CH_2)_q$—$C_{3-7}$cycloalkyl, —$CONR^{13}R^{14}$, —$NHCOR^{14}$, halogen, CN, —$(CH_2)_s NR^{16}R^{17}$, trifluoromethyl, phenyl optionally substituted by one or more $R^{12}$ groups, and heteroaryl optionally substituted by one or more $R^{12}$ groups;

$R^{12}$ is selected from $C_{1-6}$alkyl, $C_{1-6}$alkoxy, halogen, trifluoromethyl, and —$(CH_2)_s NR^{16}R^{17}$;

$R^{13}$ and $R^{14}$ are each independently selected from hydrogen and $C_{1-6}$alkyl, or $R^{13}$ and $R^{14}$, together with the nitrogen atom to which they are bound, form a 5- or 6-membered heterocyclic ring optionally containing one additional heteroatom selected from oxygen, sulfur and N—$R^{10}$, wherein the ring may be substituted by up to two $C_{1-6}$alkyl groups;

$R^{15}$ is $C_{1-6}$alkyl;

$R^{16}$ is selected from hydrogen, $C_{1-6}$alkyl and —$(CH_2)_q$—$C_{3-7}$cycloalkyl optionally substituted by $C_1$-6alkyl, $R^{17}$ is selected from hydrogen and $C_{1-6}$alkyl, or $R^{16}$ and $R^{17}$, together with the nitrogen atom to which they are bound, form a 5- or 6-membered heterocyclic ring optionally containing one additional heteroatom selected from oxygen, sulfur and N—$R^{10}$;

X and Y are each independently selected from hydrogen, methyl and halogen;

m is selected from 0, 1, 2 and 3;

n is selected from 0, 1, 2 and 3;

q is selected from 0, 1 and 2;

r is selected from 0 and 1; and s is selected from 0, 1, 2 and 3.

2. A compound according to claim 1 wherein the A ring is optionally substituted by up to two substituents independently selected from $C_1$-4alkyl, —$(CH_2)_m$—$C_{3-7}$cycloalkyl, —$(CH_2)_mCO_2R^3$, —$(CH_2)_mNR^3R^4$, —$(CH_2)_mCONR^3R^4$, —$(CH_2)_mNHCOR^3$, —$(CH_2)_mSO_2$ $(CH_2)_nR^5$, and a 5- or 6-membered heterocyclyl ring containing nitrogen optionally substituted by $C_{1-2}$alkyl or —$(CH_2)_mCO_2R^3$.

3. A compound according to claim 1 wherein $R^1$ is methyl.

4. A compound according to claim 1 wherein $R^2$ is —CO—NH—$(CH_2)_q$—$R^7$.

5. A compound according to claim 1 wherein X is hydrogen or fluorine.

6. A compound according to claim 1 which is:
N-Cyclopropyl-4-methyl-3-(3-piperidin-4-yl-1,2-benzisoxazol-6-yl)benzamide;
4-Methyl-N-(3-morpholin-4-ylphenyl)-3-(3-piperidin-4-yl-1,2-benzisoxazol-6-yl)benzamide;
N-[4-Methyl-3-(3-piperidin-4-yl-1,2-benzisoxazol-6-yl)phenyl]-2-pyrrolidin-1-ylisonicotinamide;
N-[4-Methyl-3-(3-methyl-1,2-benzisoxazol-6-yl)phenyl]-2-pyrrolidin-1-ylisonicotinamide:
N-[4-Methyl-3-(3-methyl-1,2-benzisoxazol-6-yl)phenyl]thiophene-3-carboxamide;
N-[4-Methyl-3-(3-methyl-1,2-benzisoxazol-6-yl)phenyl]-3-furamide;
4-Methyl-3-(3-methyl-1,2-benzisoxazol-6-yl)-N-(3-morpholin-4-ylphenyl)benzamide;
4-Methyl-3-(3-methyl-1,2-benzisoxazol-6-yl)-N-(1,3-thiazol-2-yl)benzamide;
N-Cyclopropyl-4-methyl-3-(3-methyl-1,2-benzisoxazol-6-yl)benzamide; or a pharmaceutically acceptable salt thereof.

7. A pharmaceutical composition comprising a compound according to claim 1 in admixture with one or more pharmaceutically acceptable carriers, diluents or excipients.

8. A process for preparing a compound of formula (I) as according to claim 1 which comprises
(a) reacting a compound of formula (II)

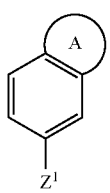

(II)

in which A is defined in claim 1 and $Z^1$ is halogen, with a compound of formula (IIIA) or (IIIB)

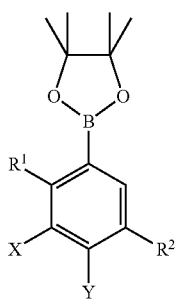

(IIIA)

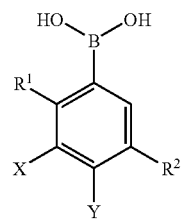

(IIIB)

in which $R^1$, $R^2$, X and Y are as defined in claim 1, in the presence of a catalyst, or
(b) final stage modification of one compound of formula (I) as defined in claim 1 to give another compound of formula (I) as defined in claim 1.

9. A compound of formula (IA);

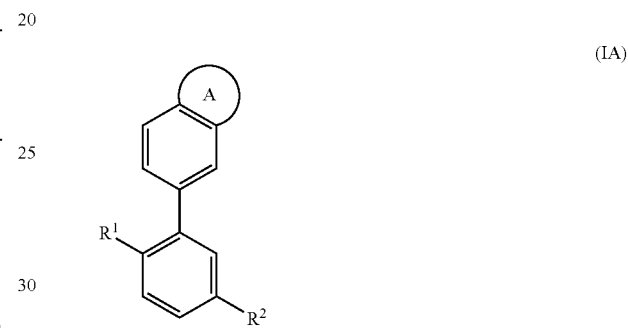

(IA)

wherein
A is a fused 5-membered heteroaryl ring selected from

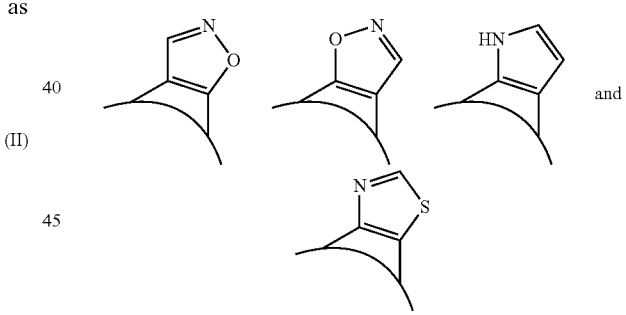

and which ring is optionally substituted by up to two substituents independently selected from $C_{1-6}$alkyl, —$(CH_2)_m$—$C_{3-7}$cycloalkyl, halogen, cyano, trifluoromethyl, —$(CH_2)_mOR^3$, —$(CH_2)_mNR^3R^4$, —$(CH_2)_mCONR^3R^4$, —$(CH_2)_mNHCOR^3$, —$(CH_2)_mSO_2NR^3R^4$, —$(CH_2)_mNHSO_2R^3$, —$(CH_2)_mSO_2$ $(CH_2)_nR^5$, a 5- or 6-membered heterocyclyl ring containing nitrogen optionally substituted by $C_{1-2}$alkyl and a 5-membered heteroaryl ring optionally substituted by $C_{1-2}$alkyl;

$R^1$ is selected from methyl and chloro;

$R^2$ is selected from —NH—CO—$R^6$ and —CO—NH—$(CH_2)_q$—$R^7$;

$R^3$ is selected from hydrogen, $C_{1-6}$alkyl optionally substituted by up to two OH groups, —$(CH_2)_m$—$C_{3-7}$cycloalkyl, —$(CH_2)_m$phenyl optionally substituted by $R^8$ and/or $R^9$ and —$(CH_2)_m$heteroaryl optionally substituted by $R^8$ and/or $R^9$ $R^4$ is selected from hydrogen and $C_{1-6}$alkyl, or $R^3$ and $R^4$, together with the nitrogen atom to which they are bound, form a 5- or 6-membered heterocyclic ring optionally containing one additional heteroatom selected from oxygen, sulfur and N—$R^{10}$;

$R^5$ is selected from $C_{1-6}$alkyl, $C_{3-7}$cycloalkyl, heteroaryl optionally substituted by $R^8$ and/or $R^9$, and phenyl optionally substituted by $R^8$ and/or $R^9$;

$R^6$ is selected from hydrogen, $C_{1-6}$alkyl, —$(CH_2)_q$—$C_{3-7}$cycloalkyl, trifluoromethyl, —$(CH_2)_r$heteroaryl optionally substituted by $R^{11}$ and/or $R^{12}$, and —$(CH_2)_r$phenyl optionally substituted by $R^{11}$ and/or $R^{12}$;

$R^7$ is selected from hydrogen, $C_{1-6}$alkyl, $C_{3-7}$cycloalkyl, CONH$R^{13}$, phenyl optionally substituted by $R^{11}$ and/or $R^{12}$, and heteroaryl optionally substituted by $R^{11}$ and/or $R^{12}$;

$R^8$ and $R^9$ are each independently selected from halogen, cyano, trifluoromethyl, $C_{1-6}$alkyl, $C_{1-6}$alkoxy, COR$^{15}$, CO$_2$R$^{15}$, and heteroaryl, or $R^8$ and $R^9$ are linked to form a fused 5-membered heterocyclyl ring containing one heteroatom selected from oxygen, sulphur and N—$R^{10}$;

$R^{10}$ is selected from hydrogen and methyl;

$R^{11}$ is selected from $C_{1-6}$alkyl, $C_{1-6}$alkoxy, —$(CH_2)_q$—$C_{3-7}$cycloalkyl, —CONR$^{13}$R$^{14}$, —NHCOR$^{14}$, halogen, CN, —$(CH_2)_s$NR$^{16}$R$^{17}$, trifluoromethyl, phenyl optionally substituted by one or more $R^{12}$ groups, and heteroaryl optionally substituted by one or more $R^{12}$ groups;

$R^{12}$ is selected from $C_{1-6}$alkyl, $C_{1-6}$alkoxy, halogen, trifluoromethyl, and —$(CH_2)_s$NR$^{16}$R$^{17}$;

$R^{13}$ and $R^{14}$ are each independently selected from hydrogen and $C_{1-6}$alkyl, or $R^{13}$ and $R^{14}$, together with the nitrogen atom to which they are bound, form a 5- or 6-membered heterocyclic ring optionally containing one additional heteroatom selected from oxygen, sulfur and N—$R^{10}$, wherein the ring may be substituted by up to two $C_{1-6}$alkyl groups;

$R^{15}$ is $C_{1-6}$alkyl;

$R^{16}$ is selected from hydrogen, $C_{1-6}$alkyl and —$(CH_2)_q$—$C_{3-7}$cycloalkyl optionally substituted by $C_{1-6}$alkyl;

$R^{17}$ is selected from hydrogen and $C_{1-6}$alkyl, or $R^{16}$ and $R^{17}$, together with the nitrogen atom to which they are bound, form a 5- or 6-membered heterocyclic ring optionally containing one additional heteroatom selected from oxygen, sulfur and N—$R^{10}$;

m is selected from 0, 1, 2 and 3;

n is selected from 0, 1, 2 and 3;

q is selected from 0, 1 and 2;

r is selected from 0 and 1; and s is selected from 0, 1, 2 and 3.

10. A compound according to claim 1 which is:

N-[4-methyl-3-(3-piperidin-4-yl-1,2-benzisoxazol-6-yl)phenyl]-2-pyrrolidin-1-ylisonicotinamide;

N-cyclopropyl-4-methyl-3-[3-(4-morpholinyl)-1,2-benzisoxazol-6-yl]benzamide;

N-cyclopropyl-4-methyl-3-{3- [2-oxo-2-(1,3-thiazol-2-ylamino)ethyl]-1,2-benzisoxazol-6-yl}benzamide;

N-cyclopropyl-4-methyl-3-[3 -(4-morpholinylmethyl)-1,2-benzisoxazol-6-yl]benzamide;

N-cyclopropyl-4-methyl-3-[3-(1-pyrrolidinylmethyl)-1,2-benzisoxazol-6-yl]benzamide;

or a pharmaceutically acceptable salt thereof.

11. A compound according to claim 1 which is:

N-[4-Methyl-3 -(3-methyl-1,2-benzisoxazol-5-yl)phenyl]-2-pyrrolidin- 1-ylisonicotinamide;

N-Cyclopropyl-3-[3-({[2-hydroxy-1-(hydroxymethyl)ethyl]amino }methyl)- 1,2-benzisoxazol-6-yl]-4-methylbenzamide;

N-(3 -Methoxyphenyl)-4-methyl-3-(3-piperidin-4-yl-1,2-benzisoxazol-6-yl)benzamide;

4-Methyl-3-(3-piperidin-4-yl-1,2-benzisoxazol-6-yl)-N-(1,3,4-thiadiazol-2-yl)benzamide;

N-[4-Methyl-3-(3-piperidin-4-yl-1 ,2-benzisoxazol-6-yl)phenyl]thiophene-3-carboxamide;

N-[4-Methyl-3-(3-piperidin-4-yl-1,2-benzisoxazol-6-yl)phenyl]-3-furamide;

N-(Cyclopropylmethyl)-4-methyl-3-(3-piperidin-4-yl-1,2-benzisoxazol-6-yl)benzamide;

or a pharmaceutically acceptable salt thereof.

12. A compound according to claim 1 which is

4-Methyl-3-(3-piperidin-4-yl-1,2-benzisoxazol-6-yl)-N-(1,3-thiazol-2-yl)benzamide;

N-Cyclopropyl-4-methyl-3-[3-(1-piperazinyl)-1,2-benzisoxazol-6-yl]benzamide;

N-Cyclopropyl-4-methyl-3-[3-(4-morpholinyl)-1,2-benzisoxazol-6-yl]benzamide;

N-Cyclopropyl-4-methyl-3-{3-[2-oxo-2-(1-piperazinyl)ethyl]-1,2-benzisoxazol-6- yl}benzamide;

Methyl(6-{5-[(cyclopropylamino)carbonyl]-2-methylphenyl}-1,2-benzisoxazol-3- yl)acetate;

N-Cyclopropyl-3-(3-{2[(2-hydroxyethyl)amino]-2-oxoethyl}-1,2-benzisoxazol-6-yl)-4- methylbenzamide;

N-Cyclopropyl-4-methyl-3-{3-[2-oxo-2-(1-piperidinyl)ethyl]- 1,2-benzisoxazol-6- yl}benzamide;

N-Cyclopropyl-4-methyl-3-{3-[2-(methylamino)-2-oxoethyl]-1,2-benzisoxazol-6- yl}benzamide;

N-Cyclopropyl-3-(3-{2-[(3-hydroxypropyl)amino]-2-oxoethyl}-1,2-benzisoxazol-6-yl) -4-methylbenzamide;

N-Cyclopropyl-3-(3-{2-[(cyclopropylmethyl)amino]-2-oxoethyl}-1,2-benzisoxazol-6- yl)-4-methylbenzamide;

N-Cyclopropyl-4-methyl-3-{3-[2-oxo-2-(1-pyrrolidinyl)ethyl]-1,2-benzisoxazol-6- yl}benzamide;

N-Cyclopropyl-3-{3-[2-(ethylamino)-2-oxoethyl]-1,2-benzisoxazol-6-yl}-4-methylbenzamide;

N-Cyclopropyl-3- {3-[2-(cyclopropylamino)-2-oxoethyl]-1,2-benzisoxazol-6-yl}-4- methylbenzamide;

N-Cyclopropyl-4-methyl-3-{3-[2-(4-morpholinyl)-2-oxoethyl]-1,2-benzisoxazol-6- yl}benzamide;

N-Cyclopropyl-4-methyl-3-{3-[2-( {[3-(methyloxy)phenyl]methyl}amino)-2-oxoethyl]- 1,2-benzisoxazol-6-yl}benzamide;

N-Cyclopropyl-4-methyl-3-{3-[2-oxo-2-(1,3-thiazol-2-ylamino)ethyl]-1,2-benzisoxazol- 6-yl}benzamide;

N-Cyclopropyl-4-methyl-3-{3-[(4-methyl-1-piperazinyl)methyl]-1,2-benzisoxazol-6- yl}benzamide;

N-Cyclopropyl-4-methyl-3-[3-(1-piperidinylmethyl)-1,2-benzisoxazol-6-yl]benzamide;

N-Cyclopropyl-4-methyl-3-[3-(4-morpholinylmethyl)-1,2-benzisoxazol-6-yl]benzamide;

N-Cyclopropyl-4-methyl-3-[3-(1-pyrrolidinylmethyl)-1,2-benzisoxazol-6-yl]benzamide; 3-(3-Amino-1,2-benzisoxazol-6-yl)-N-cyclopropyl-4-methylbenzamide;

N-Cyclopropyl-3-[3-(cyclopropylamino)-1,2-benzisoxazol-6-yl]-5-fluoro-4-methylbenzamide;

6-{5-[(Cyclopropylamino)carbonyl]-3-fluoro-2-methylphenyl}-N-(cyclopropylmethyl) -1,2-benzisoxazole-3-carboxamide;

6-{5-[(Cyclopropylamino)carbonyl]-3-fluoro-2-methylphenyl}-N-propyl-1,2-benzisoxazole-3-carboxamide;

6-{5-[(Cyclopropylamino)carbonyl]-3-fluoro-2-methylphenyl}-N-methyl-1,2-benzisoxazole-3-carboxamide;

6-{5-[(Cyclopropylamino)carbonyl]-3-fluoro-2-methylphenyl}-N,N-dimethyl-1,2-benzisoxazole-3-carboxamide;

N-Cyclopropyl-6-{5-[(cyclopropylamino)carbonyl]-3-fluoro-2-methylphenyl}-1,2-benzisoxazole-3-carboxamide;

N-Cyclopropyl-3-fluoro-4-methyl-5-{1-[(4-methylphenyl)sulfonyl]-1H-indol-5-yl}benzamide;

N-Cyclopropyl-3-fluoro-4-methyl-5-[1-(phenylsulfonyl)-1H-indol-5-yl]benzamide;

N-Cyclopropyl-3-{2-[(cyclopropylcarbonyl)amino]-1,3-benzothiazol-6-yl}-4-methylbenzamide; or a pharmaceutically acceptable salt thereof.

13. A pharmaceutical composition comprising a compound according to claim 6 in admixture with one or more pharmaceutically acceptable carriers, diluents or excipients.

14. A pharmaceutical composition comprising a compound according to claim 12 in admixture with one or more pharmaceutically acceptable carriers, diluents or excipients.

15. A pharmaceutical composition comprising a compound according to claim 11 in admixture with one or more pharmaceutically acceptable carriers, diluents or excipients.

16. A pharmaceutical composition comprising a compound according to claim 12 in admixture with one or more pharmaceutically acceptable carriers, diluents or excipients.

* * * * *